(12) United States Patent  
Thukral et al.

(10) Patent No.: US 8,818,782 B2  
(45) Date of Patent: Aug. 26, 2014

(54) SYSTEM FOR DEVELOPING PATIENT SPECIFIC THERAPIES BASED ON DYNAMIC MODELING OF PATIENT PHYSIOLOGY AND METHOD THEREOF

(75) Inventors: Ajay Thukral, Indianapolis, IN (US); Paul Galley, Cumberland, IN (US); Siva Chittajallu, Indianapolis, IN (US); Stefan Weinert, Pendleton, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1474 days.

(21) Appl. No.: 12/119,143

(22) Filed: May 12, 2008

(65) Prior Publication Data

US 2009/0006061 A1 Jan. 1, 2009

Related U.S. Application Data

(60) Provisional application No. 60/946,615, filed on Jun. 27, 2007.

(51) Int. Cl.  
*G06F 19/00* (2011.01)

(52) U.S. Cl.  
CPC ............ *G06F 19/3437* (2013.01); *G06F 19/36* (2013.01); *G06F 19/345* (2013.01); *G06F 19/3468* (2013.01)  
USPC .............................................. 703/11; 702/19

(58) Field of Classification Search  
None  
See application file for complete search history.

(56) References Cited

U.S. PATENT DOCUMENTS

| | | | |
|---|---|---|---|
| 4,151,845 | A | 5/1979 | Clemens |
| 5,193,855 | A | 3/1993 | Shamos |
| 5,307,263 | A | 4/1994 | Brown |
| 5,596,994 | A | 1/1997 | Bro |

(Continued)

FOREIGN PATENT DOCUMENTS

| | | |
|---|---|---|
| EP | 0996075 A2 | 4/2000 |
| EP | 1281351 A2 | 5/2003 |

(Continued)

OTHER PUBLICATIONS

Kathryn A. Phillips et al., Measuring Preferences for Health Care Interventions Using Analysis: An Application to HIV Testing, Health Services Research, Dec. 2002, vol. 37, No. 6, pp. 1-19.

(Continued)

*Primary Examiner* — Soren Harward  
(74) *Attorney, Agent, or Firm* — Roche Diagnostics Operations, Inc.

(57) ABSTRACT

A system for developing patient-specific therapies based on dynamic modeling of patient-specific physiology and method thereof are disclosed. The system includes software modules configured to provide access via a computer to one or more data collection protocols defining at least a type of patient-specific data to be collected and a manner in which the patient-specific data is to be collected, and to information from which one or more patient-specific models, configured to simulate one or more aspects of the patient's physiology, is developed. Another software module of the system is configured to provide access via the computer to one or more software tools that apply patient-specific data, collected according to the one or more data collection protocols, to the one or more patient specific models to determine therefrom one or more patient-specific therapies.

10 Claims, 33 Drawing Sheets

(56) References Cited

U.S. PATENT DOCUMENTS

| | | |
|---|---|---|
| 5,722,418 A | 3/1998 | Bro |
| 5,772,585 A | 6/1998 | Lavin et al. |
| 5,822,715 A | 10/1998 | Worthington et al. |
| 5,899,855 A | 5/1999 | Brown |
| 6,024,699 A | 2/2000 | Surwit et al. |
| 6,149,585 A | 11/2000 | Gray |
| 6,277,071 B1 | 8/2001 | Hennessy et al. |
| 6,544,212 B2 | 4/2003 | Galley et al. |
| 6,558,351 B1 | 5/2003 | Steil et al. |
| 6,688,891 B1 | 2/2004 | Sanford |
| 6,691,043 B2 | 2/2004 | Ribeiro, Jr. |
| 6,744,350 B2 | 6/2004 | Blomquist |
| 6,882,940 B2 | 4/2005 | Potts et al. |
| 6,923,763 B1 | 8/2005 | Kovatchev et al. |
| 2001/0012913 A1 | 8/2001 | Iliff |
| 2002/0042725 A1 | 4/2002 | Mayaud |
| 2002/0042726 A1 | 4/2002 | Mayaud |
| 2002/0072934 A1 | 6/2002 | Ross et al. |
| 2003/0011646 A1 | 1/2003 | Levine et al. |
| 2003/0028482 A1 | 2/2003 | Burak et al. |
| 2003/0036683 A1 | 2/2003 | Kehr et al. |
| 2003/0036686 A1 | 2/2003 | Iliff |
| 2003/0046114 A1 | 3/2003 | Davies et al. |
| 2003/0065669 A1 | 4/2003 | Kahn et al. |
| 2003/0074248 A1 | 4/2003 | Braud et al. |
| 2003/0093294 A1 | 5/2003 | Passantino |
| 2003/0104982 A1 | 6/2003 | Wittmann et al. |
| 2003/0115214 A1 | 6/2003 | Essar et al. |
| 2003/0125612 A1 | 7/2003 | Fox et al. |
| 2003/0212579 A1 | 11/2003 | Brown et al. |
| 2004/0025030 A1 | 2/2004 | Corbett-Clark et al. |
| 2004/0028720 A1 | 2/2004 | McAdams et al. |
| 2004/0122530 A1 | 6/2004 | Hansen et al. |
| 2004/0152622 A1 | 8/2004 | Keith et al. |
| 2005/0021369 A1 | 1/2005 | Cohen et al. |
| 2005/0031094 A1 | 2/2005 | Gilbert |
| 2005/0036619 A1 | 2/2005 | Funnell et al. |
| 2005/0038326 A1 | 2/2005 | Mathur |
| 2005/0049179 A1 | 3/2005 | Davidson et al. |
| 2005/0107318 A1 | 5/2005 | Wadsworth et al. |
| 2005/0113650 A1 | 5/2005 | Pacione et al. |
| 2005/0124874 A1 | 6/2005 | Ackerman |
| 2005/0131663 A1 | 6/2005 | Bangs et al. |
| 2005/0137481 A1 | 6/2005 | Sheard et al. |
| 2005/0137910 A1 | 6/2005 | Rao et al. |
| 2005/0154616 A1 | 7/2005 | Iliff |
| 2005/0171503 A1 | 8/2005 | Van Den Berghe et al. |
| 2005/0177400 A1 | 8/2005 | Rosenfeld et al. |
| 2005/0203001 A1 | 9/2005 | Arbit et al. |
| 2005/0214892 A1 | 9/2005 | Kovatchev et al. |
| 2005/0238581 A1 | 10/2005 | Kurland et al. |
| 2005/0272640 A1 | 12/2005 | Doyle et al. |
| 2006/0272652 A1 | 12/2006 | Stocker et al. |
| 2006/0276771 A1 | 12/2006 | Galley et al. |
| 2007/0118347 A1 | 5/2007 | Kouchi et al. |

FOREIGN PATENT DOCUMENTS

| | | |
|---|---|---|
| EP | 1382363 A1 | 1/2004 |
| GB | 2153081 A2 | 8/1985 |
| WO | 9532480 A1 | 11/1995 |
| WO | 9923597 A2 | 5/1999 |
| WO | 0029983 A1 | 5/2000 |
| WO | 0032088 | 6/2000 |
| WO | 0032097 A1 | 6/2000 |
| WO | 0033358 | 6/2000 |
| WO | 0040145 A1 | 7/2000 |
| WO | 0057774 A1 | 10/2000 |
| WO | 0060522 A2 | 10/2000 |
| WO | 0069331 | 11/2000 |
| WO | 0073927 A3 | 12/2000 |
| WO | 0100086 A1 | 1/2001 |
| WO | 0188810 | 11/2001 |
| WO | 02087506 A2 | 11/2002 |
| WO | 02088901 A3 | 11/2002 |
| WO | 02097571 A3 | 12/2002 |
| WO | 03/022327 A2 | 3/2003 |
| WO | 03030062 A1 | 4/2003 |
| WO | 03057027 | 7/2003 |
| WO | 2004084820 A2 | 10/2004 |
| WO | 2004112883 A2 | 12/2004 |
| WO | 2005082233 A1 | 9/2005 |
| WO | 2005098429 A2 | 10/2005 |
| WO | 2005102155 A1 | 11/2005 |
| WO | 2006/132899 A2 | 12/2006 |
| WO | 2007/065285 A2 | 6/2007 |
| WO | 2007143083 A2 | 12/2007 |

OTHER PUBLICATIONS

International Search Report and Written Opinion pertaining to International application No. PCT/US2008/063394 dated Sep. 17, 2008.

D.J. Spiegelhalter et al., Bayesian Methods in Health Technology Assessment: A Review; Health Technology Assessment 2000, vol. 4; No. 38, pp. 1-136, USA.

Dudde, et al., Computer-Aided Continuous Drug Infusion: Setup and Test of a Mobile Closed-Loop System for the Continuous Automated Infusion of Insulin, IEEE Transactions on Information Technology in Biomedicine, vol. 10, No. 2, Apr. 2006, pp. 395-402, United Kingdom.

Hovorka, et al., Nonlinear Model Predictive Control of Glucose Concentration in Subjects With Type 1 Diabetes, Institute of Physics Publication, Physiological Measurement, Physiol. Meas. 25 (2004), pp. 905-918, United Kingdom.

| Lapse Time | Event Meal | Amount | Meal | MEAL RELATED BOLUS | INTERNAL BOLUS EVENT | Meal Remain Amount | Meal Amount | Insulin Distribute computed for 60 gm | Compute for 60 gms | Meal Amount | Insulin Distribute computed for 100 gm | Compute for 100 gms | MEAL RELATED BOLUS – insu for 100 gms + insu for 60 gms | INTERNAL BOLUS EVENT- Insulin for 100 gms + Insulin for 60 gms |
|---|---|---|---|---|---|---|---|---|---|---|---|---|---|---|
| 480 | | | | | | | | | | | | | | |
| 490 | | | | | | | | | | | | | | |
| 500 | meal-1 Dist | 100 | 2 | 3 | | | | | 1.5 | | | 2 | 3-2+1.5 | |
| 510 | | | 0 | 1 | | | | | 0 | | | 0 | 1-0+0 | |
| 520 | | | 5 | 5 | | | | | 3 | | | 5 | 5-5+3 | |
| 530 | meal-1 Remain | 40 | 0 | 0 | 40 | 60 | 1.5 | 0 | 100 | 2 | 0 | | 0-0+0 | |
| 540 | | | 0 | 0 | | | 0 | 0 | | 0 | 0 | | 0-0+0 | |
| 550 | | | 3 | 3 | | | 3 | 2 | | 5 | 3 | | 3-3+2 | |
| 560 | | | 0 | 0 | | | 0 | 0 | | 0 | 0 | | 0-0+0 | |
| 570 | | | 0 | 0 | | | 0 | 0 | | 0 | 0 | | 0-0+0 | |
| 580 | | | 2 | 2 | | | 2 | 0 | | 3 | 2 | | 2-2+0 | |
| 590 | | | | | | | 0 | 1.5 | | 0 | | | 0-0+1.5 | |
| 600 | | | | | | | 0 | | | 0 | | | | |
| 610 | | | | | | | 0 | | | 0 | | | | |
| 620 | | | | | | | 1.5 | | | 2 | | | | |
| 630 | | | | | | | | | | | | | | |
| 640 | | | | | | | | | | | | | | |
| 650 | | | | | | | | | | | | | | |
| 660 | | | | | | | | | | | | | | |
| 670 | | | | | | | | | | | | | | |
| 680 | | | | | | | | | | | | | | |
| 690 | | | | | | | | | | | | | | |
| 700 | | | | | | | | | | | | | | |

|  |  | This may include Insulin from other meals as well as from self bolus | This may include Insulin from other meals as well as from self bolus | STEP1 | STEP2 (Last Meal - Meal Remain) | STEP3 | STEP4 Aligned with last Meal Event | STEP 5 | STEP 6 | STEP 7 Aligned with last Meal Event | STEP 8 | STEP 9 |

TEST STAND EMULATOR MENU – APCATS VER 3.1

EVENT TYPE FOR TRIGGERED EVENTS (SET BY DISTURBANCE MENU)

990:

| | [DT-] Start: BEFORE Trigger | [SMS] Span: Small Meal | [AMS] Amt: Small Meal |
|---|---|---|---|
| [E01] BLOOD_DRAW ID# | | | |
| [E02] BG_METER mg/dl | [DT0] Start: @ Trigger | [SMM] Span: Medium Meal | [AMM] Amt: Medium Meal |
| [E03] SNACK[CHO] g | [DT+] Start: AFTER Trigger | [SML] Span: Large Meal | [AML] Amt: Large Meal |
| [E04] BREAKFAST[CHO] g | | [SEW] Span: Warm Up Exercise | [AEW] Amt: Warm Up Exercise |
| [E05] LUNCH[CHO] g | | [SEE] Span: Endurance Exercise | [AEE] Amt: Endurance Exercise |
| [E06] SUPPER[CHO] g | | [SES] Span: Strenuous Exercise | [AES] Amt: Strenuous Exercise |
| [E07] HI_BG_INTERVENTION U | | | |
| [E08] LO_BG_INTERVENTION g | | | |
| [E09] ADVERSE_EVENT ID# | | | |
| [E10] EQUIPMENT_FAILURE ID# | | | |
| [E11] PRIME_PUMP U | | | |

992:

| Nos. | EVENT LIST (DISTURBANCES) | Event Start Time day : hr : mt | EVENT TYPE | ALGO Action Time [Relative] [mt] | Action Span Time day : hr : mt | Amount |
|---|---|---|---|---|---|---|
| 1 | Breakfast [Norm] | 0 Day : 0 hr : 0 mt | | | | |
| 2 | Rab [Endo] | 0 Day : 0 hr : 0 mt | | | | |
| 3 | Insulin Step[Pulse] [mU per min] | 0 Day : 0 hr : 1 mt | | | | |
| 4 | Insulin Step[Pulse] [mU per min] | 0 Day : 0 hr : 1 mt | | | | |
| 5 | Glucose Step[Pulse] | 0 Day : 1 hr : 0 mt | | | | |
| 6 | Breakfast [Norm] | 0 Day : 2 hr : 0 mt | [E04] | -10 | 0 Day : 2 hr : 0 mt | 100 |
| 7 | Glucose Step[Pulse] | 0 Day : 3 hr : 0 mt | | | | |
| 8 | Glucose Step[Pulse] | 0 Day : 5 hr : 0 mt | | | | |

994:

PatientIN: C:\APCATS\APSV2.5\PATIENTS\HMVNI69060801.mat    Experiment DIR

Save    Cancel    Help    Close

986

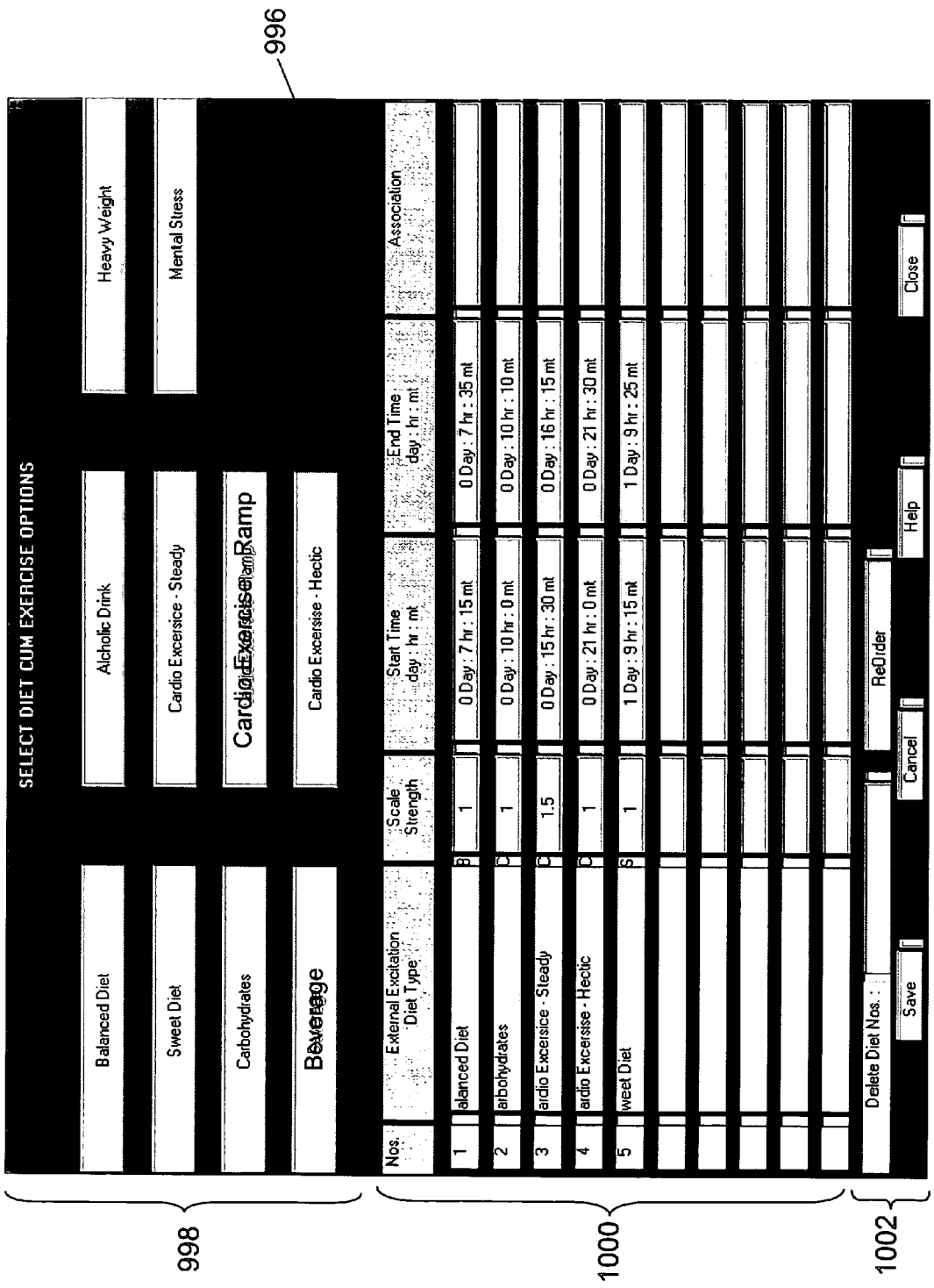

FIG. 28

Connect Ports [Actuator --> Model]

1004

1006 — Get Ports:
- AP. Flow Rate [mU/min] — 1
- AP. Amt Dispensed [mU] — 2
- AP. TimeStamp [min] — 3
- Actuator[1] Flag — 4

1008 — In Ports:
- Insulin Rate [microU/min]
- Insulin Basal Rate [microU/min]
- Glucose Exogenous Rate [mg/dl/min]
- Glucose Endogenous Rate [mg/dl/min]

- User Name: Joe Doe
- Experiment: PRHIOS
- PARADIGM: SUB q

1012 / 1014:
- ENTER EXPERIMENT BRIEF
- VIEW STATUS
- START SIMULATION — 1022

1016 / 1018 / 1020:
- SAVE DUM DOCUMENT RUN
- STARTUP FORM
- EXIT APCATS

Start-up Entry Form 1010

- User Name: Joe Doe
- Experiment: PRHIOS
- PARADIGM: SUB q
- Details

NEW — 1060

Old — 1015

Save

FIG. 32

SYSTEM FOR DEVELOPING PATIENT SPECIFIC THERAPIES BASED ON DYNAMIC MODELING OF PATIENT PHYSIOLOGY AND METHOD THEREOF

CROSS REFERENCE TO RELATED APPLICATIONS

This invention relates to U.S. application Ser. No. 12/119,201, entitled "MEDICAL DIAGNOSIS, THERAPY, AND PROGNOSIS SYSTEM FOR INVOKED EVENTS AND METHOD THEREOF," now U.S. Pat. No. 8,712,748, and which the disclosure is herein fully incorporated by reference.

FIELD OF THE INVENTION

The present invention relates generally to chronic disease management, and in particular to a computerized system for developing patient specific therapies for chronic disease management based on dynamic modeling of patient physiology and method thereof.

BACKGROUND OF THE INVENTION

Traditionally, therapies/treatments are based on single clinical tests and measurement devices to diagnose disease or ailment. For the most part, the intent in using such tests and devices is to obtain a single, quality measurement. Such a measurement provides a snap-shot. However, a series of measurements is required in order to understand the system dynamics and the underlying system characteristics of the disease.

A series of measurements clearly results in more data. However, it is not always easy to translate such data into actionable information. In fact, it is a far from trivial task to identify what problems can be tackled and what prerequisites are needed so as to make the more abundant data provided by continuous or frequent measurement useful in the practice of medicine. In addition, pharmaceutical companies perform the task of characterizing the metabolic activity of the drug and determining drug dosage schema. In general, pharmaceutical companies perform elaborate clinical trials to determine drug potency and drug efficacy for a target population. But strictly speaking, both pharmacokinetics and pharmacodynamics for a drug is patient specific. A population based approach is not ideally suited for determining medication for ailments such as diabetic patients where insulin drug is used on daily basis due to the variability of such a chronic disease. In such cases, the dosing schema is normally fine-tuned by practicing healthcare professionals starting from given guidelines. Typically, a healthcare provider, with the help of the patient, follows a controlled monitoring and insulin dosage adjustment scheme.

The most prevalent forms of diabetes are due to decreased production of insulin (Type 1 Diabetes Mellitus, the first recognized form), or decreased sensitivity of body tissues to insulin (Type 2 Diabetes Mellitus, the more common form). Treatment of the former requires insulin injections, while the latter is generally managed with oral medication and only requires insulin if the oral medications are ineffective. Other health problems that accelerate the damaging effects of diabetes are smoking, elevated cholesterol levels, obesity, high blood pressure, and lack of regular exercise. Accordingly, patient understanding and participation in treatment is vital since blood glucose levels change continuously.

Controlling glucose is the best method for slowing the damaging effect of glucose on organs. Conventional therapy (CT), intensive conventional therapy (ICT), and intensive conventional therapy for pump users (CSII) are common approaches used to control glucose. A limitation of such therapy approaches is that they do not make use of tools that account for patient-specific factors such as physiological variability, metabolic differences, and the effects of stress, exercise, sickness, and meals.

Glucose concentration is the primary parameter that is normally measured for euglycemic control (e.g., in order to provide a normal level of glucose in the blood). Other available information for determining better treatment concerns the metabolic loads resulting from various activities such as ingesting meals, performing physical activity, work-related stress, and so forth. Insulin delivery, other medications, and so forth are further regulating mechanisms for the targeted physiological parameter. The therapy rules are defined in terms of glucose measurements, insulin sensitivity, insulin-to-carbohydrate ratio, basal insulin rate, and other factors such as stress level and the effect of exercise. Except for the glucose measurements, current approaches determine the parameters based on rules of thumb, empirical rules, and iterative assessments based on glucose measurements.

In view of the above, there is a serious shortcoming in the current clinical approaches to addressing the needs of a diabetic patient in day-to-day life. No single solution has integrated the varied approaches available. The methods offered to date do not directly assess patient-specific needs; rather, specifics are addressed over a period of time through trial and error. In addition, simply integrating the various approaches available in the art would not accomplish the desired effect. There are specific elements for each of the methods that have to developed and tuned for the overall process to work with the desired level of safety, accuracy, and robustness. In addition, it is desirable to provide health care practitioners with tools for collecting patient-specific information over time and applying the collected information to dynamic, patient-specific models when designing therapies for such chronic illnesses and/or diseases.

SUMMARY OF THE INVENTION

The present invention may comprise one or more of the features recited in the attached claims, and/or one or more of the following features and combinations thereof.

In one embodiment, a computerized system used by a user to developing patient specific therapies for chronic disease management of a patient is disclosed. The system comprises: a data collection module which enables the system to collect patient specific data according to a data collection protocol and performs integrity and quality checks on the patient specific data; a user interface which enables the user to select a patient model from a plurality of patient models provided by the system; a module validation module which enables the system to validate the selected patient model; an analyses module which enables the system to apply the patient specific data to the selected patient model to extract useful patient specific physiological information, and to use the extracted patient specific physiological information to develop one or more patient specific therapies for treating the chronic disease of the patient; a result validation and presentation module which enables the system to validate the one or more patient specific therapies and to present validated ones of the one or more patient specific therapies on the user interface for approval.

In another embodiment, a computerized system for developing patient-specific therapies based on dynamic modeling of patient-specific physiology is disclosed. The system comprises a computer configured to provide access to a number of software modules stored in at least one database or other memory unit. The number of software modules include: a first software module configured to provide access via the computer to one or more data collection protocols defining at least a type of patient-specific data to be collected and a manner in which the patient-specific data is to be collected, a second software module configured to provide access via the computer to information which develop one or more patient-specific models configured to simulate one or more aspects of physiology of the patient, a third software module configured to provide access via the computer to one or more software tools that apply patient-specific data, collected according to the one or more data collection protocols, to the one or more developed patient specific models to determine therefrom one or more patient-specific therapies, and a fourth software module configured to provide access via the computer to one or more software validation tools that validate the patient-specific therapies and to present the one or more patient-specific therapies on the computer.

In yet another embodiment, a computer implemented method of developing patient specific therapies for chronic disease management of a patient on a computerized system is disclosed. The method comprises: providing a data collection module which enables the system to collect patient specific data according to a data collection protocol and performs integrity and quality checks on the patient specific data; providing a user interface which enables the user to select a patient model from a plurality of patient models provided by the system; providing a module validation module which enables the system to validate the selected patient model; providing an analyses module which enables the system to apply the patient specific data to the selected patient model to extract useful patient specific physiological information, and to use the extracted patient specific physiological information to develop one or more patient specific therapies for treating the chronic disease of the patient; providing a result validation and presentation module which enables the system to validate the one or more patient specific therapies and to present validated ones of the one or more patient specific therapies on the user interface for approval.

In still yet another embodiment, a computer implemented method for developing patient-specific therapies based on dynamic modeling of patient-specific physiology on a computer is disclosed. The method comprises: configuring the computer to provide access to a number of software modules stored in at least one database or other memory unit; configuring a first one of the software modules to provide access via the computer to one or more data collection protocols defining at least a type of patient-specific data to be collected and a manner in which the patient-specific data is to be collected; configuring a second one of the software modules to provide access via the computer to information which develop one or more patient-specific models configured to simulate one or more aspects of physiology of the patient; configuring a third one of the software modules to provide access via the computer to one or more software tools that apply patient-specific data, collected according to the one or more data collection protocols, to the one or more developed patient specific models to determine therefrom one or more patient-specific therapies; and configuring a fourth one of the software modules to provide access via the computer to one or more software validation tools that validate the patient-specific therapies and present the one or more patient-specific therapies on the computer.

These and other features and advantages of the invention will be more fully understood from the following description of various embodiments of the invention taken together with the accompanying drawings.

BRIEF DESCRIPTION OF THE DRAWINGS

The following detailed description of the embodiments of the present invention can be best understood when read in conjunction with the following drawings, where like structure is indicated with like reference numerals, and in which:

FIG. 16 is a depiction of a processing of a carbohydrate rectification module according to the present invention;

FIG. 26 is a depiction of a graphical user interface providing an event entry form for a simulation environment according to the present invention;

FIG. 27 is a depiction of a graphical user interface providing a select diet/cumulative exercise form for a simulation environment according to the present invention;

FIG. 28 is a depiction of a graphical user interface providing a connect ports form for a simulation environment according to the present invention;

FIG. 29 is a depiction of a Run/Store pane portion of the graphical user interface of FIG. 22 which provides the basic functionality for loading data, saving data, and running simulation;

FIG. 32 is a depiction of a graphical user interface providing a Start-up Entry form for a simulation environment according to the present invention;

DETAILED DESCRIPTION

Figure 1:
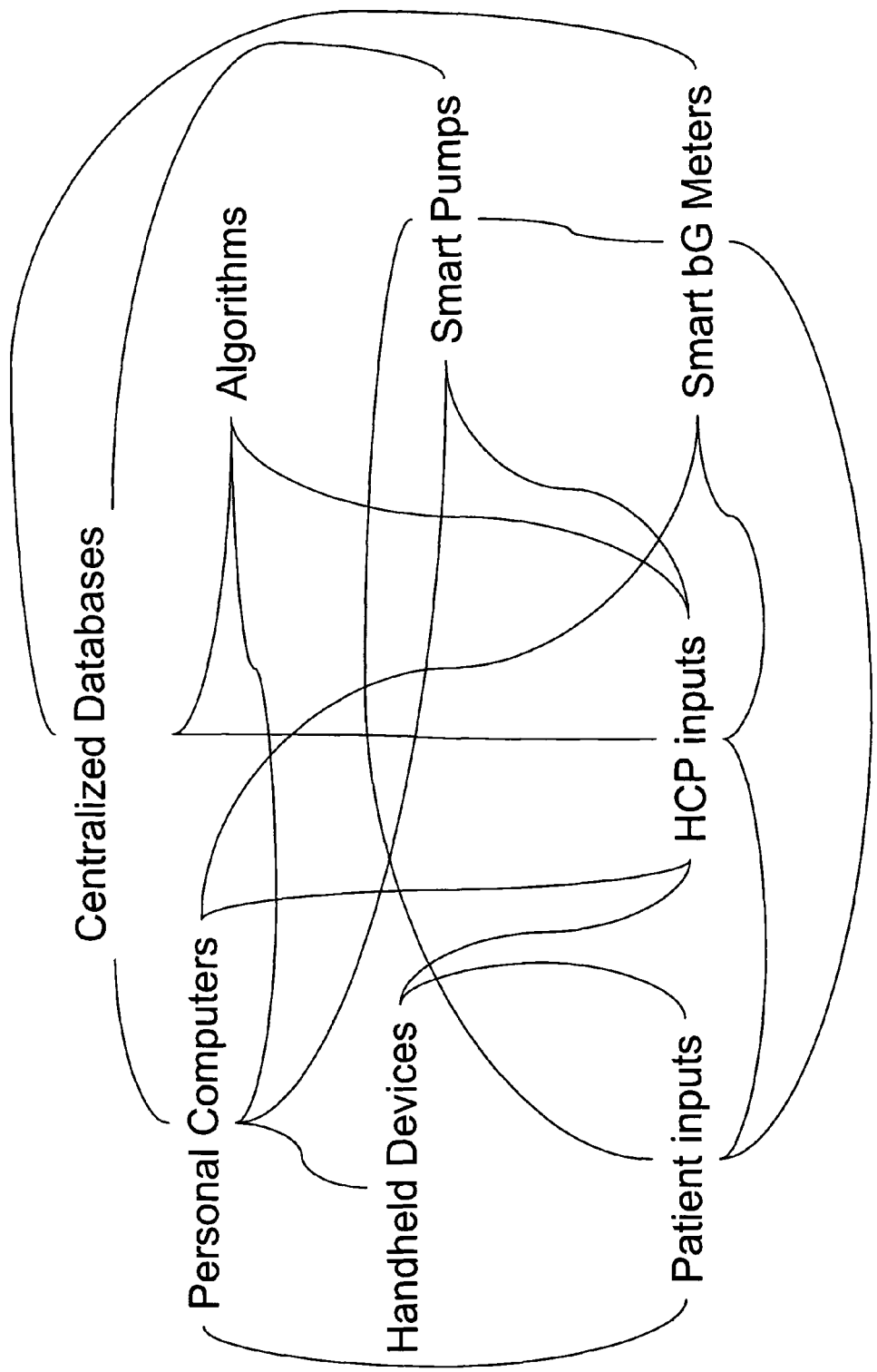
FIG. 1 is a block diagram of various diabetes management utility tools/devices used to capture patient activity and assist in insulin therapy which may communicating information.

Generally, the present invention is computer architecture and processes that helps analyze treatment and managing of diseases such as diabetes, asthma, and heart disease, which are chronic in nature by analyzing human physiology and metabolic activity of an individual in a dynamic system, and enabling a user to define protocol, analyze collected data, fine tune therapy requirements, and provide patient-specific diagnosis, therapy advice, and prognosis. Although the present invention herein is discussed in terms of helping a patient, it is understood that the present invention may be used to help multiple patients.

In one embodiment, the present invention enhances therapy outcome by testing a proposed solution and providing a confidence interval around it. In some instances, the proposed solution is a specialized protocol to specifically address characterization and/or control of an effect, or in some cases multiple effects. Instead of approaching the problem using population-based rules, the method of present invention, from the start, assumes a patient-specific disease state by which to tailor therapy to the patient's metabolic, physiological, and lifestyle considerations.

In one embodiment, the present invention provides a systematic tool that directly addresses the need to determine patient specific insulin therapy. It is to be appreciated that the process of the present invention is applicable to open-loop, closed-loop, and semi-closed loop systems, and can be adapted to various glucose measurement methods and various insulin delivery methods. In others embodiments, the present invention is applicable to other chronic ailments requiring continuous drug therapy.

The present invention uses physiological models, metabolic models, and mathematics for determining a drug dose based on the pharmacokinetics and pharmacodynamics of the drug and relevant parameters. Those skilled in the art understand that pharmacokinetics is the study of the absorption, distribution, metabolism, and excretion of drugs whereas pharmacodynamics is the study of the biochemical and physiologic effects of drugs and their mechanisms of action, and of the correlation of drug concentrations to drug effects. In one embodiment, the present invention computerizes the methodology of pharmacodynamics to operate on inputted data and provides as output the relationship between pharmacokinetics and pharmacologic effect as either adverse or desired.

The present invention helps users to understand the pharmacologic effects of various physiological states and helps diagnose disease, refine therapy, and allows development of not only therapy that is patient specific, but therapy that is more stringent than existing therapies. The system and methods thereof of the present invention are further extended to provide the prognosis for the chronic disease of the individual.

In one embodiment, the invention discloses an apparatus from the perspective of generic input entries and/or generic output entries for receiving/commanding (i) devices, (ii) algorithm and (iii) informing user informational/actionable/warning of outcomes. The event information can be a continuous update or occurring in discrete fashion. An event is thus a transaction. The method further describes the algorithm structure to enable therapy generation.

In another embodiment, the invention disclosed a method that uses the collected glucose data and other available information to synthesize the patient specific model and use it to determine the therapy parameters. This process may involve (1) identifying a patient-specific model and (2) defining the various physiological parameters. The identified model is simulated or specific analysis tools are applied to meet the definition of the physiological parameters so as to deduce their values. The determined parameters are patient-specific since they are derived from a patient-specific model.

In another embodiment, the present invention further enables a user to perform various analyses, including assessing critical scenarios via simulations, to ensure a stable and robust solution which meet requirements such as ADA guidelines and/or maintains key parameters, for example HbA1C, within a desired target range of the subject.

The present invention thus enables a practicing doctor with a tool that helps analyze the patient's characteristic behavior and that, in turn, uses this analysis to determine therapy, examine therapy outcomes, and understand patient characteristics. The present invention is an integrated system that houses the various system components-patient data storage, mathematical analysis tools, data presentation methods, integration with external devices, data compliancy techniques, therapy approaches tested for stability and robustness—which together offer a superior approach to diagnosis, therapy determination, and prognosis for patients with diabetes. Hereafter, and using diabetes as an example, the present invention is elaborated in greater details. In particular, a discussion on the measurements, analysis, and other information used by the present invention is now provided.

Measurements & Analysis

As known, diabetes is a metabolic syndrome wherein the physiology of the body is not functioning normally to regulate blood glucose for various etiological reasons. To manage the disease, there are many diabetes management inputs, utility tools, and devices used to capture patient activity and assist in insulin therapy. For example, FIG. 1 is an illustration of typical disease management components for managing diabetes which need to interact and exchange information for determining and evaluating effectiveness of prescribed insulin therapy. The disease management components include: personal computers, centralized databases for data management, algorithms providing procedures for managing pump infusion based on user inputs, glucose measurements, and insulin-delivered amounts, user inputs via user interface, measurements, tests, etc., healthcare professional (HCP) inputs via user interface, measurements, tests; and smart insulin pumps, smart blood glucose (bG) meters, and other handheld devices which may be either integrated or standalone devices that function independently. In general, these disease management components interact to exchange information with each other which is shown via the arrows in FIG. 1. Such an information (data) exchange is a regular requirement when function calls are made by programs associated with/provided by the components and are in general called along with input/output arguments. The arguments represent structured content, and at least all of the device disease management components ideally should understand such structure and its potential/actual content. However, in such a system, informing various components that an event has occurred is a problem. An event is a unit of information generated by one component which can be used by another component (e.g., a bG measurement, hypoglycemic episode, hyperglycemic episode value, adjustment in a dosage, change in a protocol, change in an algorithm, etc.). In particular, the problem lies in providing an information structure which captures the necessary information from a large set of use cases that use such disease management components. Additional problems lie in the fact that the exchanging of information when managing a chronic disease such as diabetes is time critical as well as content critical. Furthermore, the exchanged information has to be usable by the devices for machine interpretation as well as by human for human interpretation.

Characteristic of the exchange information is also another problem. For example, the characteristics of the information in management of a chronic disease were noted as follows. Time has many variations, for example, when does the event happen, when does one event occur with respect to another event, and how long can the event occur. An event itself has a characteristic nature and the following aspects are needed—what event is triggered, what is the strength, or magnitude of the event. An event could be consisting of an occurrence at the specified time or series of occurrence with corresponding magnitude of specified action. Can an event be turned OFF once it has been initiated or more general question is can the previous event be modified with specific case being deletion. The frequency of the event also needs to be known. How is the event triggered in context of being either a synchronous call or an asynchronous call. The present invention addresses these problems as will become evident in the discussion provided hereafter.

Measurements of physiological parameters form the backbone of the DTPS. For example, there are readily measurable parameters such as body temperature, blood pressure, body weight, and so forth. Other parameters may be provided from elaborate laboratory tests such as blood sample testing used to identify specific constituents, urinalysis, and cultures performed to identify microbes, and so forth. However, there are limitations to measuring any physiological parameters. For example, complex and expensive set-up can limit the availability of information provided, such as from test like HbA1C or insulin assays. Quantitative and/or qualitative information about activities that impact the human physiology such as exercise, meal intake (i.e., ingestion of carbohydrates), and stress can be skewed. Furthermore, such parameters may show up as effects that are designated as ON/OFF rather than being quantified. In addition, it is expected that quantified information may not be rigorously attained for various limiting factors. There also exist technological limitations, for example, measurements not available due to physical or ethical limitations in accessing a physiological parameter, such as amount of gluconeogenesis or gut glucose absorption, for example. Moreover, mathematically-constructed parameters such as bioavailability and drug efficacy are normally population based and may not be specific enough to certain individual patients.

For diabetes care, glucose measurements normally obtained using glucose meters are the primary parameters for conducting therapy management. There are several secondary parameters relevant for managing diabetes, such as HbA1C, ketones, and FFA. However, such measurements are not needed on a regular basis. In addition, there is information about activities (such as the amount and execution rates for meal consumption and exercise) that is important in adjusting and correcting therapy. The present invention, which can help analyze patient-specific needs, employs such data on measurements and analysis to build models that are used to estimate physiological parameters that cannot be directly measured, and to represent the patient's underlying physiology and metabolism. The present also permits visualization of such physiological parameters as they continuously evolve such that the user may understand the underlying dynamic behavior of the chronic disease. Such analysis and visualization of the present invention offers greater insight into the workings of the system (the diabetic person) and can help healthcare providers with diagnosis, therapy determination, and prognosis. Accordingly, the present invention enhances the healthcare provider's ability to analyze data, diagnose the disease, determine therapy, and arrive at a prognosis for the therapy. To help illustrate the utility of the present invention, the following example is provided hereafter.

To test for diabetes in an individual, a commonly used protocol requires the individual to fast for at least 8 hours. A fasting glucose is measured and then the individual undergoes an oral glucose tolerance test, which entails intake of a concentrated glucose drink, followed by several glucose measurements normally over the course of 2 hours. Based on the data collected, a diagnosis for diabetes is determined. The use of frequent or continuous data offers the following advantages over the use of sparse measurements: data can be plotted to visualize patterns and trends; data can be used to predict or anticipate changes in measurements; and data can be used to build models and represent underlying pharmacokinetics and pharmacodynamics. In general, the above mentioned data is collected using well-defined protocols. The method of the present invention encompasses the following aspects. Patient-specific data is collected to support the diagnosis, therapy, and prognosis tools of the present invention. A data analysis is proposed recognizing that protocols are analysis specific and that each protocol is specialized to identify or determine a particular aspect of the disease (a cause-effect relationship). The proposed data analysis is intended to best quantify how the patient's disease system is working and to identify patient-specific parameters. Next, the patient's disease system dynamic behavior is defined by the present invention recognizing that population-based studies represent average effects and do not necessarily address patient-specific needs. The present invention also takes into account that, although the principles needed to understand how a dynamic system behaves may be clear in a specific situation, it is not reasonable to expect a person to perform critical mathematical analysis mentally.

For example, medications, especially those that are used daily and/or needed on a regular basis, interact with activities such as exercise, stress, different foods, and other medications, all of which can have substantial influence on the effect of the medication. A systematic tool of the present invention described hereafter in a later section that plays out the mathematical aspects of determining such effects will help the healthcare provider to evaluate and quantify the effect. The effects can be further translated into medication schema for a given effect corresponding therapy is selected. The effects can be used to predict the impact of the effect and to help generate warnings and alerts. The description hereafter explains the system (apparatus) and methodology of the present invention.

Overall System

Figure 2:
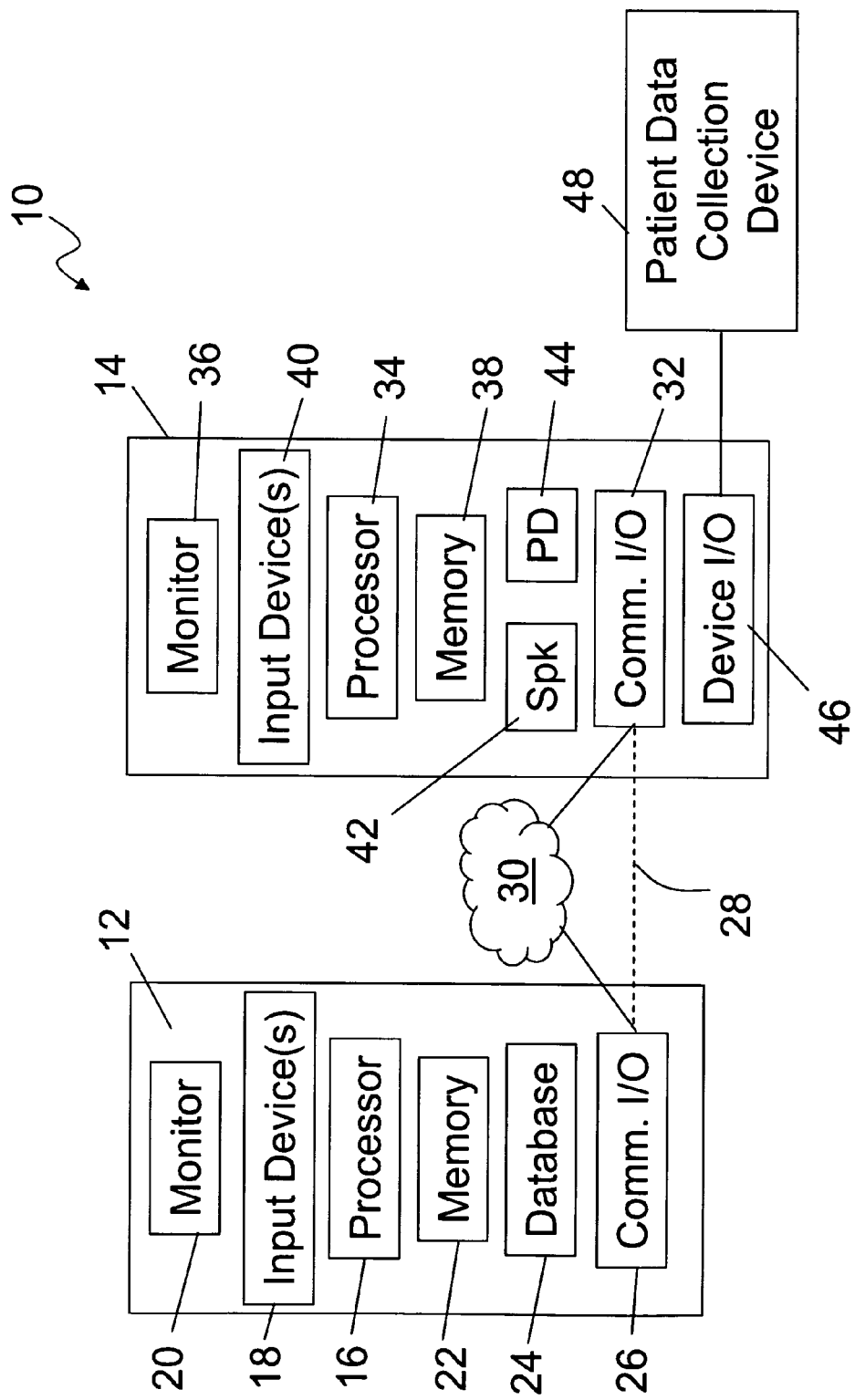
FIG. 2 is a block diagram illustrating an embodiment of a Diagnosis, Therapy and Prognosis System (DTPS) for developing patient-specific therapies based on dynamic modeling of patient physiology according to the present invention.

With the above measurements and analysis in mind, DTPS is a hardware-software system that operates in a typical client-server environment running on a PC platform, and is illustrated in block diagram by FIG. 2. The overall system is envisioned as distributed geographically and accessible via an intranet and/or internet setup. In one illustrated embodiment, the system 10 provides a server computer 12 and a client computer 14. The server computer 12 includes a conventional processor 16 that is operatively connected to an input device 18, a monitor 20, and memory 22 (e.g., RAM, ROM, and hard drive(s)). The input device 18 may be any one or a combination of a conventional keyboard, a conventional point-and-click device, microphone, or the like, and the monitor 20 may be any conventional computer monitor. The processor 16 of the server computer 12 is also operatively connected to a database 24 is internal to the computer 12, or may alternatively be external to the computer 12. The processor 16 of the server computer 12 is further operatively connected to a conventional communication interface 26.

The client computer 14 likewise includes a conventional processor 34 that is operatively connected to a conventional monitor 36, conventional memory 38 (e.g., RAM, ROM, and hard drive(s)), and a conventional input device 40 which may be any one or a combination of a conventional keyboard, a conventional point-and-click device, microphone, or the like. Alternative, input may also be via the monitor 36 in embodiments wherein the monitor 36 includes one or more touch-screen buttons or switches. The client computer 14 may further include one or more conventional speakers 42 operatively connected to the processor 34. The processor 34 of the client computer 14 is further operatively connected to a device interface 46 that is configured to be operatively connected, either wirelessly or via a wired connection, to one or more external devices.

In one embodiment, for example, the device interface 46 may be or include a conventional input/output port configured for wired connection to an external device. Examples of such a conventional input/output port include, but should not be limited to, a conventional universal serial bus (USB) port, a conventional RS-232 port, or the like. Alternatively or additionally, the device interface 46 may be or include a conventional wireless transceiver configured to wirelessly communicate with a similar transceiver of an external device. Examples of such a wireless transceiver include, but should not be limited to, an infra-red (IR) transceiver, a radio frequency (RF) transceiver, an inductive transceiver, an acoustic transceiver or the like.

The processor 34 of the client computer 14 provides information to, or receives information from, an external device 48, such as in the form of a patient data measurement and/or collection device, via the device interface 46. Examples of the patient data measurement and/or collection device 48 may include, but should not be limited to, a blood or tissue glucose sensor or other glucose measurement device, a body temperature sensing or measurement device, a body weight measuring device, a blood pressure monitoring device, an HbA1C monitoring device, an implantable or externally worn drug infusion pump, e.g., for administration of insulin or one or more other blood glucose lowering or raising drugs, a hand-held or other data collection device for monitoring patient meal intake data, patient exercise data, patient illness data, etc., or the like.

The processor 34 of the client computer 14 is further operatively connected to a conventional communication interface 32. The communication interfaces 26 and 32 may be any conventional communication interfaces that provide for electronic communications between the server computer 12 and the client computer 14. In the illustrated embodiment, for example, the communication interfaces 26 and 32 are configured to provide for electronic communications between the server computer 12 and the client computer 32 via the World Wide Web (WWW), internet and/or intranet in a conventional manner. Alternatively or additionally, the communication interfaces 26 and 32 may be or include telephone modems so that the server computer 12 and the client computer 32 may communicate via telephone. This disclosure contemplates that electronic communications between the server computer 12 and the client computer 14 may alternatively be accomplished via other conventional wired or wireless communications links. In any case, it will be understood that the system 10 may include multiple networked server computers 12 that may or may not be distributed geographically, and that each server computer 12 may serve multiple client computers 14 that may be distributed geographically. In addition, the processes (i.e., software portion) of the present may be configured on the client side or the server side, depending on the use case scenario, which is discussed hereafter.

Software Portions

Figure 3:
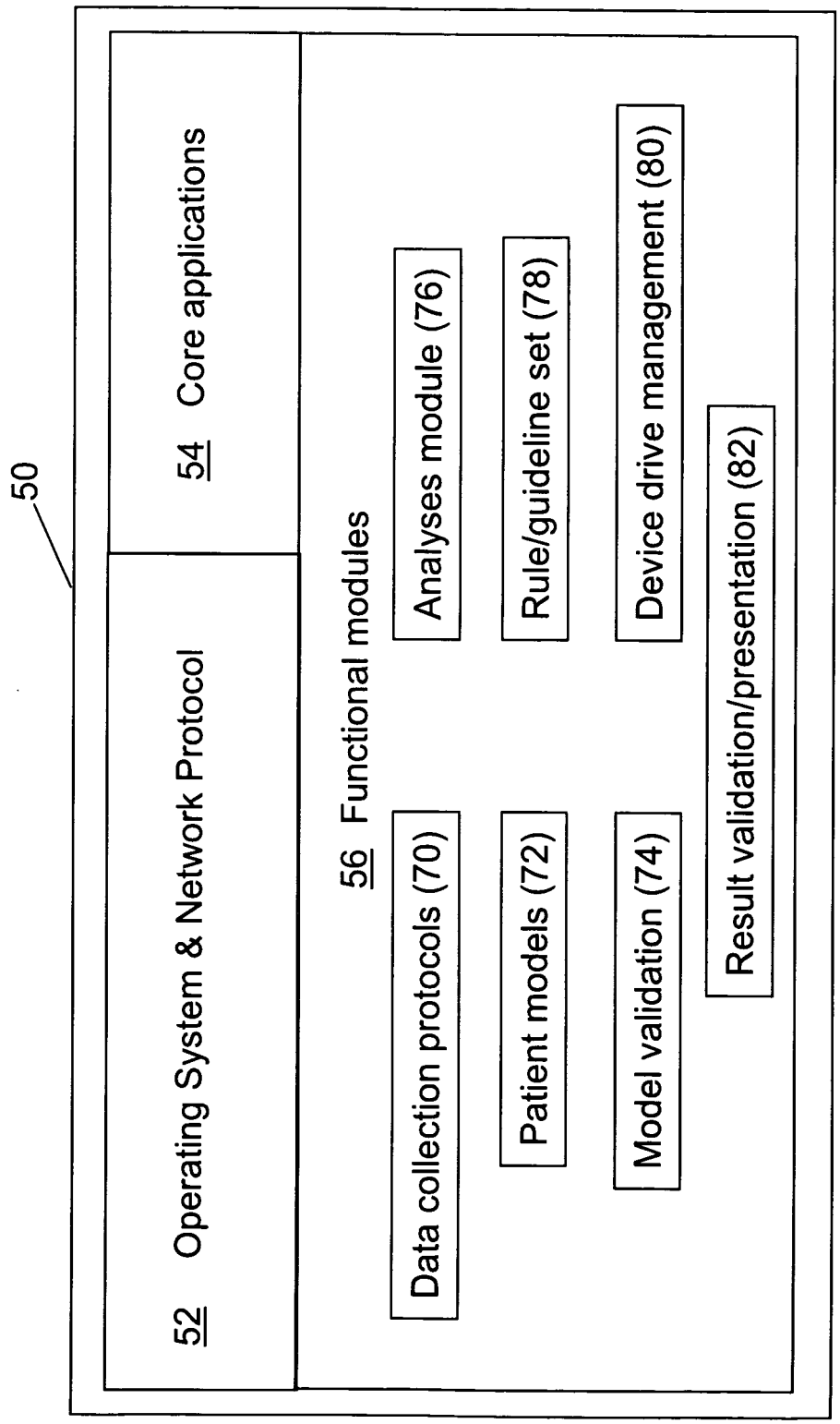
FIG. 3 is a block diagram of a software embodiment used in the system of FIG. 2 and showing a functional modules portion according to the present invention.

With reference to FIG. 3, one illustrative embodiment of software 50 used by the system 10 of FIG. 2 and according to the present invention is shown. The software 50 will be understood to be configured in a conventional manner to allow for appropriate interaction between the client computer 14 and the server computer 12 for performing user authentication, acquiring and/or storing data in a database and conducting ancillary activities such as background processing of data, automation of triggering events, and the like. In the illustrated embodiment, the software 50 includes an operating system and network protocol portion 52, a core applications portion 54, and functional modules portion 56. The operating system and network protocol portion 52 is configured in a conventional manner to allow interaction between the various computers, devices and/or databases. The core application and functional modules portions 54 and 56, respectively, may reside on the server computer 12, the client computer 14, or at least in part on both.

Generally, the core applications portion 54 comprises a number of conventional software algorithms and other conventional data management software, which may be commercially available. As one specific example, the core applications portion 54 may contain conventional mathematical software packages. Generally, such core mathematical tools will include one or more optimization tools, one or more statistical analysis tools, one or more simulation tools, one or more sensitivity tools, one or more visualization tools, and one or more tools for extracting information (such as conventional pattern recognition tools, envelop recognition tools, and the like). Specific examples include, but are not limited to, any one or more of LAPACK, a linear algebra package, IMSL (Independent Media Solutions Limited) software tools and libraries, OPTIMA client/server tools, STATS statistical tools, graphical presentation tools, and the like. Database organization and security software algorithms, particularly for collected patient data, are other specific examples of conventional software algorithms and other conventional data management software that may be contained in the core applications portion 54. Such database organization and security software algorithms will generally ensure, for example, HIPAA compliance, data integrity, security and authentication, and interoperability with other system applications. Conventional drivers for supporting various database activities and/or drivers for interacting with various electronic data measurement/collection devices 48 (see FIG. 2) is another specific example of conventional software algorithms and other conventional data management software that may be contained in the core applications portion 54 as well as one or more conventional web browsers to allow for interaction with various computers, databases and appropriate web sites. Examples of such conventional web browsers may include, but should not be limited to, Internet Explorer, Netscape, Mozilla, Opera, Lynx, and the like. It will be understood that the core applications portion 54 may include more or fewer software algorithms and/or data management software, and that the above examples have been provided only for illustrative purposes and should not be considered to be limiting in any way.

Functional Modules

As shown by FIG. 3, in the illustrated embodiment, the functional modules portion 56 includes a data collection protocols block 70, a patient models module 72, a model validation module 74 and an analyses module 76, all connected to a rule/guideline sets module 78. The functional modules portion 56 further includes a device driver management module and a results validation and presentation module 82. Illustratively, the functional modules portion 56 operates to manage data, query data, store and retrieve data, provide call routines to mathematical packages and libraries located in the core applications portion 54, provide routines for analyzing data and graphical routines for presenting data in the form of text and graphs, and provide drivers for communicating with various external devices 48. Alternatively or additionally, the functional modules portion 56 may be configured to perform more or fewer functions.

To develop a patient-specific therapy for an illness generally, and for a chronic illness specifically, data relating specifically to the patient is collected. Generally, the type of patient-specific data to be collected and the manner in which it is to be collected depends upon many factors, including but not limited to, the particular illness for which the therapy is being developed, the severity of the illness, the types and availability of therapy solutions, the age, weight and sex of the patient, one or more of the personal habits of the patient, such as the propensity of the patient follow a strict dietary schedule and/or to exercise on a regular basis, to follow one or more available therapy schedules, and the like. The data collection protocols module 70 contains multiple different data collection protocols, each designed to provide for the collection of one or more particular types of patient-specific data to be collected in a particular manner. More specifically, each data collection protocol contained in the data collection protocols module 70 specifies the data that is to be collected, the manner in which the data is to be collected, i.e., the manner in which the data collection is to be performed, any restrictions on the data collection protocol, any special tools and/or devices, electronic or otherwise, to be used in collecting the data, and any safeguards and/or data collection techniques that will ensure and/or increase the quality of the collected data. Illustratively, the patient-specific data that is collected according to any of the various data collection protocols is stored in the database 24 (FIG. 2), although some or all of this collected data may alternatively be stored in one or more other databases and/or memory units that is/are accessible by the server computer 12 and/or client computer 14.

Each data collection protocol stored in the data collection protocols module 70 is defined for a specific purpose, and comprises a data collection schema that has been tested and evaluated to achieve at least one particular objective, provided that conventional data compliance and integrity checks have been satisfied. To this end, each data collection protocol may include, or have access to, for example, a data compliancy procedure in the form of a mathematical module that checks for inconsistencies in the collected data, and that checks requirements defined for the particular data that has been collected. Examples of such requirements include, but are not limited to, time stamp consistency, data value range(s), date range(s), and the like. Additionally, each data collection protocol may include, or have access to, for example, a data quality procedure in the form of a mathematical module that examines the quality of the collected data in terms of its performance and/or statistical properties.

The rule/guideline sets module 78 provides rule sets that govern collection of the patient-specific data according to the various data collection protocols available in the data collection protocols module 70. Additionally, the rule/guideline sets module 78 provides guidelines for collecting the patient-specific data according to the various data collection protocols. Such guidelines may provide, for example, but not limited to, computer readable descriptions of the various data collection protocols, guidance as to when, i.e., under what circumstances, to, or when not to, use a particular protocol or protocols, advantages and/or disadvantages of using a protocol, goals that may be achievable or unachievable by using a protocol, limitations of a protocol or of the applicability of a protocol, or the like.

Generally, data that is collected for any of the various data collection protocols in the data collection protocols module 70 may be collected in various ways using various conventional techniques. Examples include, but are not limited to, measurements of a patient-specific state or states using one or more conventional measuring devices, events or conditions that a patient is subject to, and the like. The measurements of patient-specific data may be made available to the client computer 14 using any one or more of the electronic devices 48 described herein. Additionally or alternatively, measurements of patient-specific data may be made using conventional electronic or non-electronic measuring devices and/or systems, and the results may be manually entered or input into the client computer 14 using the input device 40 e.g., keyboard, point-and-click device, microphone or other conventional input device or mechanism. Events or conditions that a patient is subject to may include, for example, but should not be limited to, intake of meals and snacks, exercise, illness, stress, and the like. Such information may be made available to the client computer 14 via one or more electronic devices 48 and/or via manual entry using one of the conventional input devices.

Examples of data collection protocols that may be available in the data collection protocols module 70 include, but are not limited to, one or more data collection protocols that provide for the collection of patient blood or tissue glucose measurements as a function of time, of patient body temperature measurements as a function of time, of ambient temperature measurements (around the body of a patient) as a function of time, of patient heart rate and/or pulse rate as a function of time, of patient blood pressure as a function of time, of one or more other patient physiological condition parameters such as weight, menses, stress, illness, and the like, of meal or snack, i.e., carbohydrate intake, information as a function of time, of patient physical activity as a function of time, of insulin delivery information over time, of intervention information as a function of time, of patient visits to clinics and/or hospitals as a function of time, specific information about one or more of meal intake, exercise performance, and the like, use of specialized instruments and/or devices, use of one or more of paper copies, telephone calls, internet communications for exchanging and/or recording information, and the like.

The system 10 of FIG. 2 is illustratively designed to target the human species, although embodiments of the system 10 that target other animals are contemplated by this disclosure. Generally, some of the behavioral characteristics exhibited by humans are common across the species, while other individual behavioral characteristics depend on other factors such as gender, age, ethnicity, and the like. Models of human physiological behavior can be constructed as mathematical representations of human physiology, and may illustratively be defined in terms of differential equations. Such patient models may further be developed to be generally the same across all patients while also anticipating behavioral variability. In such cases, the model parameters will have patient-specific values.

The patient models module 72 (FIG. 3) makes available a plurality of such patient models that are configured to model mathematically one or more aspect of human physiology, which provides mapping to different physiological states, conditions and/or parameters. For example, the patient models module 72 may model glucose absorption in humans while one or more other models may model one or more effects of administering insulin (or other glucose raising or lowering drug). The patient models module 72 may include competing models that are configured to model the same physiological aspect, and each such model may have certain advantages or disadvantages for defining particular model parameters, for collecting patient-related data, and/or for analyzing particular data. In this regard, the rule/guideline sets module 78 may include rules and/or guidelines relating to the particular applicability or inapplicability of one model over another for a particular physiological aspect, for a particular patient type (e.g., age, gender, race, etc.) and/or use scenario, relating to limitations on the use of any particular model, relating to links to sources where modeling work may be in the process of development, and the like. One or more of the models may further include accompanying use-case information. The plurality of different patient models available via the patient models module 72 allows for the mapping of models and/or model parameters to specific physiologic states, conditions or parameters.

The patient models may be stored and/or accessed directly by the patient model module 72 from a portable memory device 44, computer memory 38, and/or a computer readable medium, such as, for example, compact disc, digital video disc, and the like. The patient models may be accessed and/or stored indirectly by the patent model module 72 from the database 24 or other memory units connected to the server 12, and/or the Internet 30. For example, the database 24 or other memory units may include a databank of model types and/or structures with relevant links to literature and/or other relevant technical documents. Alternatively or additionally, the database 24 or other memory unit may include a databank of clinical trial results, e.g., tracer studies, and/or relevant links to information relating to such clinical trials, from which the underlying model structure may be obtained. In either case, one or more suitable patient models may be accessed directly or indirectly by accessing, via the patient models module 72, information relating to the structure, parameters and/or development of such one or more models. Generally, then, the patient models module 72 may contain one or more developed patient models that is/are specific to one or more particular aspects of human physiology, and/or may contain information from which one or more such models may be located, determined and/or developed. The one or more developed patient models may be or include one or more proprietary patient models, i.e., developed by a particular person and/or entity and restricted in its use by that person and/or entity, and/or one or more commercially or otherwise publicly available patient models, i.e., available from one or more $3^{rd}$ parties.

When a particular model has been selected using the patient models module 72, values of the model parameters must then be determined. To accomplish this, the patient models module 72 may further include one or more sub-modules that provide for the determination of such model parameters. Examples of such one or more parameter determination sub-modules may include, but should not be limited to, one or more sub-modules for identifying model parameters, one or more sub-modules for providing input, output, state and/or parameter descriptions, one or more sub-modules for determining parameter ranges, one or more sub-modules for determining model parameter sensitivities (e.g., model parameter gain values), one or more sub-modules for providing previously developed, derived or defined model parameters, and the like.

One or more of the sub-modules for identifying model parameters may employ data fitting techniques that implicitly or explicitly determine parameter values. General examples of such sub-modules, include, but not limited there to those which provide: Bayesian analysis to provide an initial guess and provide prior distribution for parameter estimations, a cost function to solve for parameter estimates (posterior distribution), statistical analysis, numeric analysis, iterative/non-iterative techniques for range analysis, gain values analysis, test scenarios analysis, modeling, and those which provide pre-known parameters descriptions (input, output, state, etc.), ranges, and sensitivities (e.g., gain values). Alternatively or additionally, one or more of the sub-modules for identifying model parameters may specify a procedure or framework for identifying the model parameters. An example of one such model parameter identification procedure or framework, which should not be considered to be limiting in any way, is one that: i) provides the model parameters and initial guesses for the parameters, ii) if a Bayesian approach is followed, provides a priors for parameter estimation, iii) sets up, selects, or uses a particular cost function, iv) selects or uses a particular cost function solving technique or framework, and v) iteratively or non-iteratively solves for the model parameter estimates.

One or more of the sub-modules for determining parameter ranges may employ any one or more of statistical, numeric, iterative or non-iterative techniques to implicitly or explicitly determine acceptable ranges for one or more of the model parameters and/or to determine model parameter variability. One or more such sub-modules may, for example, use conventional techniques to create test scenarios representing model parameter ranges over which the model can be tested and evaluated. For example, in one embodiment the present invention may be used to define and implement test scenarios on the computer that help in testing the recommended patient-specific therapy and quantifying the quality of therapy potentially achievable using the recommended patient-specific therapy. In other embodiments, when therapy is specified, the present invention may be used to evaluate the scenario and augment the therapy, such as for example, with constraints on lifestyle e.g., limits of meal amount, restrict fast absorbing meals, and the likes.

One or more of the sub-modules for determining model parameter sensitivities may employ one or more statistical, numeric, iterative or non-iterative techniques to implicitly or explicitly determine model parameter gain values. One or more such sub-modules may, for example, use conventional techniques to analyze the model parameter sensitivities to evaluate the stability of the model over one or more model parameter ranges and/or in response to errors in model parameter determination.

For diabetes care in particular, glucose measurements obtained using various known blood and/or tissue glucose measuring techniques provide a primary parameter around which euglycemic control is sought to be achieved via conventional diabetes therapy. This disclosure recognizes that other parameters are also relevant for managing diabetes, and that dynamic or static determination of such parameters may or may not be needed on a regular or periodic basis. Examples of such other parameters include, but are not limited to, HbA1C (glycosylated or glycated hemoglobin—a form of hemoglobin that may be used to identify plasma glucose concentration over time), FFA (free fatty acids), ketone bodies (by-products of the break down of fatty acids), and the like. While some such parameters may be monitored via parameter measurement, others may require estimation via measurements of other parameters and appropriate modeling, i.e., virtual measurements. Additional information relating to patient activities may further be used to modify, adjust or correct diabetes therapy. Examples include, but are not limited to, meal amounts, consumption frequency and/or execution rates, exercise frequency, duration and/or load, illness frequency, duration and/or severity, and the like. It is envisioned that at least some of the patient models available via the patient models module 72 just described will incorporate therein one or more such physiological parameters and/or other information so that such one or more models can be used to estimate one or more physiological parameters that cannot be directly measured or that is/are difficult to directly measure. The resulting patient models will provide for the ability to monitor, either dynamically or statically, the patient's underlying physiology such as the patient's metabolism.

The functional modules portion 56 further includes a model validation module 74 that provides for access to one or more computer-based simulation programs configured to analyze one or more aspects of a patient model. One or more simulation programs may, for example, be stored in the database 24 or other memory unit, and in such cases the model validation module 74 provides an interface for accessing such programs. Alternatively or additionally, the model validation module 74 may contain links to literature or other sources of model validation programs. In any case, the one or more computer-based simulation programs will generally analyze the operation of the selected patient model under one or more specific test scenarios, and compare the results with known standards, with a broader population of data, with results of previously analyzed models, with statistically expected results, or the like. The one or more computer-based simulation programs may additionally flag and/or report inconsistencies with the comparison. Illustratively, the model validation module 74 provides access to one or more computer-based simulation programs that perform any one or more of: i) conducting computer-based simulations relating to selected patient models, ii) validating the selected patient models over one or more specified operating ranges, iii) providing information that facilitates an understanding of the operating space, limitations, and error sources for the selected patient models, iv) applying specific use-case to the selected patient models and analyzing the model results, v) testing the selected patient models with clinical data that has been previously collected, and the like.

The model validation module 74 may include one or more sub-modules that provide particular analytical tools for evaluating the selected patient models. Examples of such one or more analytical tool sub-modules may include, but should not be limited to, one or more sub-modules for testing particular use-case scenarios, one or more sub-modules for testing the patient model over one or more specified operating ranges, one or more sub-modules for statistically analyzing the selected patient models, and the like. The one or more sub-modules for testing particular use-case scenarios may illustratively provide access to one or more software programs that exercises the patient model in a manner that compares one or more identified model characteristics with predetermined standards as described above. The one or more sub-modules for testing the patient model over one or more specified operating ranges may illustratively provide access to one or more software programs that analyzes the patient model over one or more specified operating ranges to determine how well the patient model simulates the underlying illness or disease and/or how well the patient model simulates the reaction of the underlying illness or disease to prescribed therapy, over varying operating ranges and/or conditions. The one or more sub-modules for statistically analyzing the selected patient models may illustratively provide access to one or more software programs that exercise the patient model to generate model one or more solutions in a manner that allows for a determination of whether the solution(s) is/are representative of one or more expected statistical characteristics.

The rule/guideline set module 78 may illustratively provide for rule sets governing the operation of one or more of the sub-modules, and/or provide guidelines relating to the particular applicability or inapplicability of one computer-based simulation program over another for a particular patient model, model type, model operating range and/or use scenario, relating to limitations on the use of any particular simulation program, relating to links to sources where relevant computer-based simulation programs may be found and/or relating to links to sources where relevant computer-based simulation program work may be in the process of development, and the like.

The functional modules portion 56 of the software 50 (FIG. 3) further includes an analyses module 76 that provides for access to one or more analysis tools, at least some of which are resident in the database 24 or other memory unit in the form of one or more conventional mathematical software packages that are accessible via the core applications portion 54 as described hereinabove. General examples, include, but are not limited to, one or more optimization tools, one or more statistical analysis tools, one or more simulation tools, one or more sensitivity tools, one or more visualization tools, and one or more tools for extracting information (such as conventional pattern recognition tools, envelop recognition tools, and the like). Specific examples include, but are not limited to, any one or more of LAPACK, a linear algebra package, IMSL (Independent Media Solutions Limited) software tools and libraries, OPTIMA client/server tools, STATS statistical tools, GRAPHICAL presentation tools, and the like.

The analyses module 76 may further make available other data analysis and/or visualization tools, one or more of which may be specific to the therapy sought to be developed. Any such other analysis and/or visualization tools may be stored in the database 24 or other memory unit, and may be accessed directly via the analyses module 76, or may be available elsewhere and be accessed indirectly via relevant links to such tools via the analyses module 76. Illustratively, the core mathematical tools that may be accessible via the analyses module 76 may include, but are not limited to, i) one or more optimization tools, ii) one or more statistical analysis tools, iii) one or more simulation tools, iv) one or more sensitivity tools, v) one or more visualization tools, and vi) one or more tools for extracting information, e.g., via pattern recognition or the like. In one embodiment, the analyses module 76 provides analysis tools which enables the system to perform at least one of simulations, statistical analysis, sensitivity analysis, visualizations, information extraction, optimizations, and to provide recommendations which include at least one of type, amount, and timing for dosing, exercise, and meals. Each recommendation in one embodiment may include action at a current time, at a future tome or at times determined by the analysis or at times determined by the end-user.

The rule/guideline set module 78 may illustratively provide for rule sets governing the operation of one or more of the analysis and/or other tools available via the analyses module 76, and/or provide guidelines relating to the particular applicability or inapplicability of one such tool over another for a particular tool, of tool type, of any limitations on the use of any particular to, relating to links to sources where relevant analysis, visualization or other tools may be found and/or relating to links to sources where relevant work on such analysis, visualization or other tools may be in the process of development, and the like.

Using the tools available via the analyses module 76, patient-specific data that has been collected according to one or more of the protocols in the data collection protocols module 70 can be applied to one or more selected patient models, selected via the patient models module 72 and validated via the model validation module 74, to extract useful patient-specific physiological information. The useful patient-specific physiological information may then be used to develop one or more therapies for treating the patient-specific illness or disease. In the context of diabetes therapy, for example, the tools available via the analyses module 76 may include, but should not be limited to, software tools that provide for the extraction of information such as model parameter values, software tools that provide for the analysis of diabetes-related data, optimization software tools, trend analysis software tools, software tools that provide for the determination and/or recommendation of basal and bolus dosing, software tools that provide for the determination and application of warnings for conditions such as hypoglycemia and hyperglycemia, software tools that provide for the development of one or more graphical interfaces that allow for patient input of patient-related data, and the like.

On example software tool that provides for the development of one or more graphical interfaces that allow for patient input of patient-related data is described in co-pending U.S. application Ser. No. 12/119,207, entitled PATIENT INFORMATION INPUT INTERFACE FOR A THERAPY SYSTEM, which is assigned to the assignee of this disclosure, and the disclosure of which is incorporated herein by reference. Another is that described in co-pending U.S. application Ser. No. 11/297,733, entitled SYSTEM AND METHOD FOR DETERMINING DRUG ADMINISTRATION INFORMATION, which is assigned to the assignee of this disclosure, and the disclosure of which is incorporated herein by reference. Other software tools that provide for the development of one or more graphical interfaces that allow for patient input of patient-related data will occur to those skilled in the art, and any such other software tools are contemplated by this disclosure.

The functional modules portion 56 of the software 50 (FIG. 2) further includes a device driver management module 80 that provides for access to one or more device drivers as described hereinabove with respect to the core applications portion 54. Also included is a results validation and presentation module 82 that provides for the analysis and validation of the results of applying the patient-specific data to the one or more selected patient models, and that provide one or more tools for visually presenting such results. For example, the module 82 may provide access to one or more simulation tools that may be selected and executed to test critical cases for therapy robustness, assess the stability of the solution, determine and assess the sensitivity of the therapy to parameter variation and/or generate a confidence interval by performing a large number of simulations, and/or give an indication that the therapy outcome lies within a certain range. The module may alternatively or additionally provide access to one or more tools that may be selected and executed to provide one or more fail-safes for ensuring safe and robust usage of the results, an analysis of the effectiveness of the results, e.g., efficacy, potency, affinity, an analysis of the results for therapy convergence and stability, one or more computer-based bio markers, e.g., HbA1C, one or more patient monitoring schedules, one or more therapy suggestions, and the like. The module 82 may further provide access to one or more visual presentation software tools or packages for graphically presenting the results in any conventional format, e.g., text report, charts, plot, etc. A specific example illustrating a process according to the present invention using the system 10 of FIG. 1 and the software 50 of FIGS. 2 and 3 is provided hereafter.

Process Implementation Example

Figure 4:
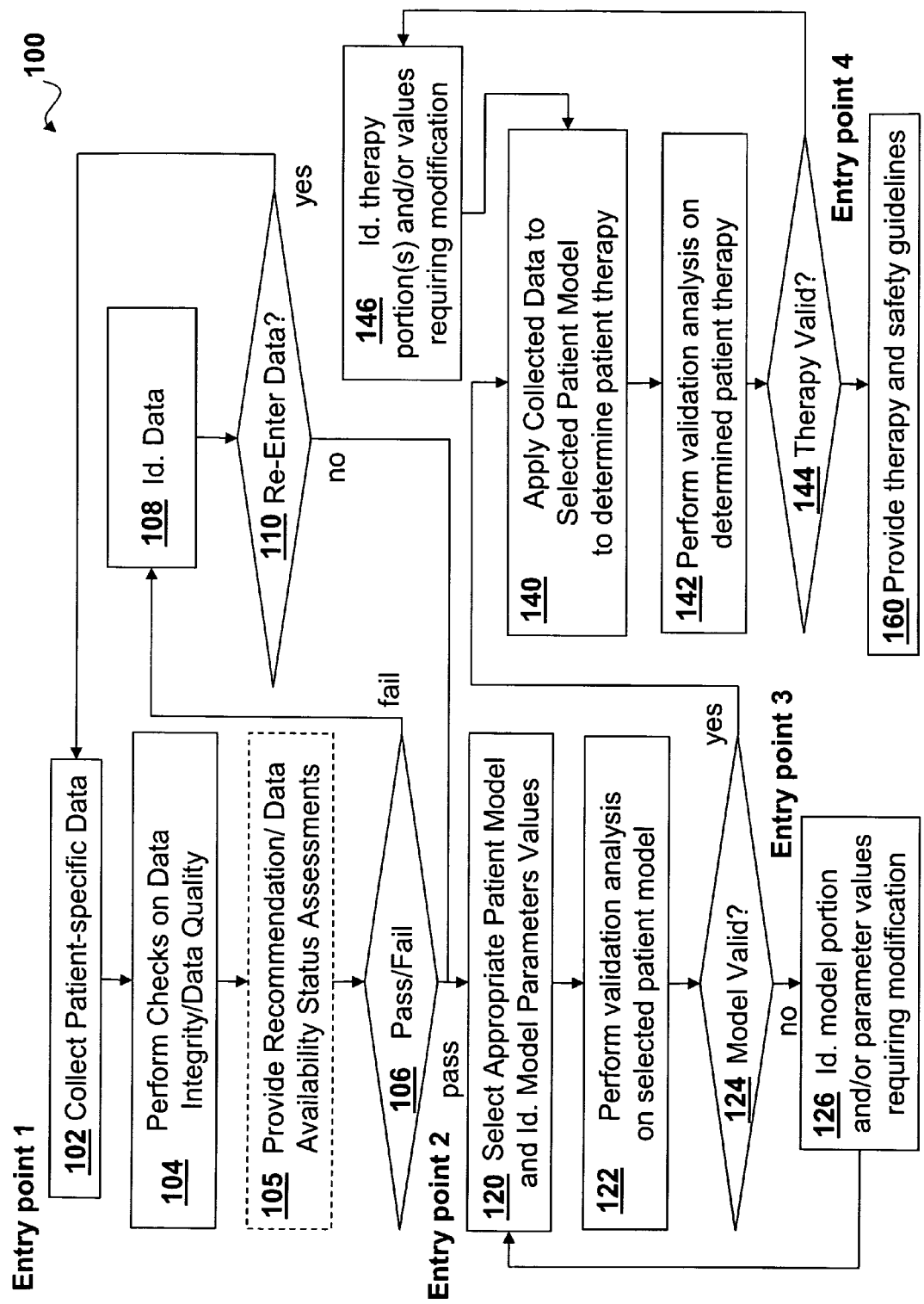
FIG. 4 is a flowchart of one illustrative embodiment of a process for developing patient-specific therapies according to the present invention.

Referring now to FIG. 4, a flowchart is shown of one illustrative embodiment of a process 100 for developing patient-specific therapies. The process 100 helps to ensure that minimum rules for a therapy are met, selection of a choice(s) is relevant of achieving a therapy goal, and that specific problems to improve therapy of the patient are addressed. The process 100 need not be executed in its entirety at one time, and may instead be accessed at any of a number of entry points as will be described in greater detail hereinafter.

A first entry point of the process 100 advances to step 102 where patient-specific data is collected according to one more of the data collection protocols accessible via the data collection protocols module 70. It is to be appreciated that the collection protocols in one embodiment may be those specified by governing medical bodies, such as ADA or similar organizations, and in other embodiments, as established by a healthcare professional, such as a medical practitioner, doctor, and the likes. At step 102, patient-specific data may be collected by entering such data into the client computer 14 using any one or more embodiments of the patient data measurement/collection device 48 described hereinabove with respect to FIG. 1. Alternatively or additionally, the patient-specific data may be collected at step 102 by measuring or otherwise determining the patient-specific data in a conventional manner, and then entering such data into the client computer 14 via one or more of the input device 40 or the monitor 36 in embodiments wherein the monitor 36 includes one or more touch-screen buttons or switches.

Following step 102, the process 100 advances to step 104 where checks are performed on the integrity and quality of the collected patient-specific data. In one embodiment, for example, the data collection protocols module 70 includes, or has access to, a data compliancy procedure in the form of a mathematical module that checks for inconsistencies in the collected data, and that checks requirements defined for the particular data that has been collected. Examples of such requirements include, but are not limited to, time stamp consistency, data value range(s), date range(s), and the like. In one embodiment, the data compliancy procedure is pre-evaluated for best outcome. Additionally, the data collection protocols module 70 may include, or have access to, for example, a data quality procedure in the form of a mathematical module that examines the quality of the collected data in terms of its performance and/or statistical properties. For example, to determine whether the data quality is poor, the system examines several aspects of the collected data. In this embodiment, one aspect is relevancy of the collected data in which a relevancy query called from a database module consisting of queries is employed to extract data content from the collected data. The extracted data content is analyzed statistically, via an appropriate statistical module which receives the extracted data content and outputs results, regarding frequency of measurements per day, meal time, bolus, bolus magnitude with respect to meal size, and so forth to a desired baseline. Another aspect is timing of the collected data, where in step 104, a data time series is examined in terms of comparing a requirements baseline against what the patient has collected to provide a confidence interval for the collected data. In the illustrated embodiment, the client computer 14 or sever computer 12 is operable to perform such checks at step 104 by accessing and executing either or both of the data compliancy and data quality modules.

Following step 104, optionally the process 100 may include presenting to the user on the monitor 36 recommendations for proceeding in selecting an action and a data availability status based on a current assessment of the data quality and availability of certain data in the collected data in step 105. As discussion giving greater details on this step is provided in a later section. The process 100 advances then to step 106 where the client computer 14 or server computer 12 is operable to determine whether the data integrity and/or data quality checks of each data collection protocol have passed or failed (or pass/failed based on the selected recommendation and data availability status in step 105). If one or more data integrity and/or quality checks have failed, algorithm execution advances, in the illustrated embodiment, back to step 102 so that a new set of patient-specific data may be collected according to the one or more failed data collection protocols.

Optionally, as shown in FIG. 4, the process 100 may include an additional step 108 between the "FAIL" branch of step 106 and step 102. In this embodiment, the client computer 14 or server computer 12 is operable at step 108 to identify only the data that needs to be re-collected, i.e., data within any one or more data collection protocol that is corrupt or that otherwise does not pass the data integrity and/or quality checks. Thereafter at step 102, only the data identified at step 108 need be re-collected. In another embodiment, an option step 110 is provided, wherein the user is asked whether the identified data needs to be re-entered at this time. If the answer is yes, then the process 100 proceeds back to step 102, otherwise the process 100 continues with further analysis using the available data collected at a second entry point identified in FIG. 4.

The second entry point into the process 100 exists between the "PASS" branch of step 106 and the subsequent step 120. It will be understood that the second entry point may also function as an exit point from the execution of steps 102-108. In any case, the "PASS" branch of step 106 and/or the entry point 2 advances to step 120 where one or more appropriate patient model(s) is/are selected from the one or more patient-specific models available via the patient models module 72. At step 120, the one or more patient models may be selected using the client computer 12 and/or server computer 12 through a suitable user interface such as the input device 40 (e.g., keyboard, point-and-click device, microphone or other suitable user input device). Alternatively or additionally, step 120 may be carried out using the client computer 12 and/or server computer 12 by accessing one or more patient model via an external memory storage device, such as a compact disc read only memory (CD-ROM), floppy disk, USB-compatible memory device or the like. Alternatively or additionally still, step 120 may be carried out by accessing an appropriate link stored in the database 24 or other memory unit, and then accessing the corresponding website or other source of the link via a conventional web browser forming part of the core applications 54. If, on the other hand, the stored link corresponds to a reference to one or more publications, step 120 may be carried out by accessing the one or more publications, either manually or via the client computer 14 and/or server computer 12. In any case, when the one or more patient-models is/are selected, step 120 further includes identifying the model parameter values using any one or more of the techniques described hereinabove. In one embodiment and with reference made to FIG. 21, an example to illustrate model parameter identification is provided and discussed hereafter.

To illustrate the parameter determination, a simple example is described outlining the processing in step 120 e.g., by patient model 72 (FIG. 3). Consider a clinical study wherein a Type I patient is being treated with a fast acting insulin type such as, for example, Lyspro using an insulin pump, such as device 48 (FIG. 2). The pump is capable of infusing basal insulin profile along with manually commanded bolus. For the clinical study, the pump is provided with infra-red control and can be command in a close loop fashion by a control algorithm such as, for example, ALGO 510 (FIG. 5) which will be discussed in later sections. The clinical trial consisted of series of small and large boluses subcutaneously using the pump. As such an impulse response model was selected, which is described by equation (1) as:

$$h(t) = \frac{K}{\beta^\alpha \Gamma(\alpha)} t^{\alpha-1} e^{-t/\beta} \text{ml}^{-1} \text{min}^{-1}. \tag{1}$$

The impulse response model of equation (1) consists of three main parameters. These parameters are: $\alpha$ representing approximately number of compartments which in directly is acting as a filter, $\beta$ which is the time of peak absorption rate per unit insulin distribution volume, and K is the gain factor. The absorbed insulin is distributed within the body's insulin distribution volume. The insulin is utilized by tissues such as muscles, liver and also cleared from the circulating blood. A differential equation (2) which describes the whole process approximately is:

$$\frac{dC_I}{dt} = -\frac{1}{\tau}C_I + \int_{-\infty}^{\tau} u(\eta)h(t-\eta)d\eta. \qquad (2)$$

Figure 21:
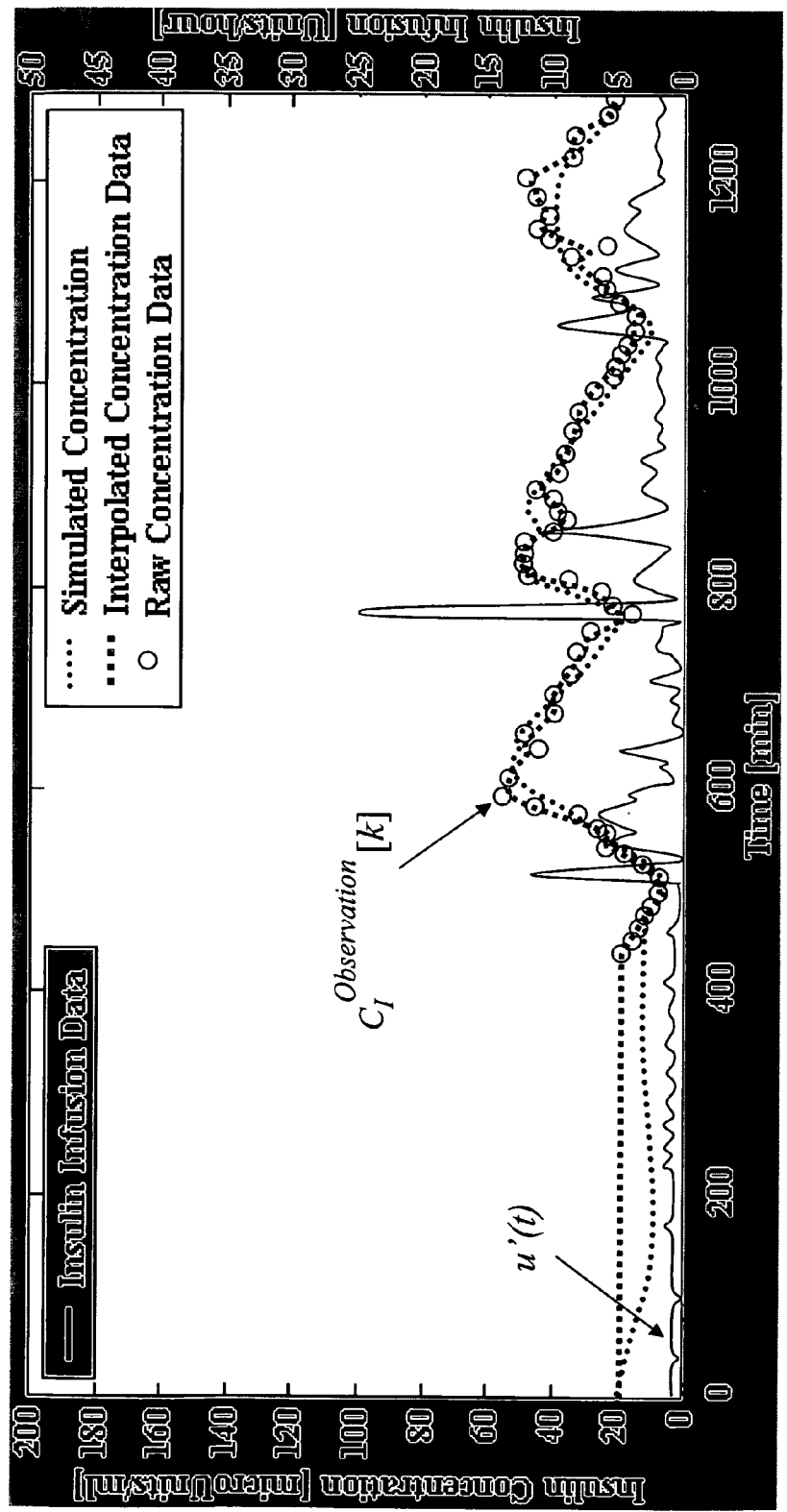
FIG. 21 is a graph provided as an example to illustrate model parameter identification according to the present invention.

The first term $$-\frac{1}{\tau}C_I$$

is the clearance term and is simply assumed to be linearly proportional to insulin concentration (first order exponential decay). However, the time constant $\tau$ (min) is unknown. The second term on the right side of equation (2) is a convolution term between the infused insulin boluses with the insulin absorption function. The term provides the net insulin absorbed per unit volume into the circulation by an arbitrary sequence of insulin boluses. The input insulin boluses u(t) per U/min=0.278 u'(t), where the u'(t) is in U/hr. The problem is then to determine the parameters for patient specific insulin kinetics. As shown in FIG. 21, the input insulin boluses u'(t) per U/hr and the output insulin concentration observations $C_I^{Observation}[k]$ U/mL (circles) is needed.

The problem is solved by selecting the set of parameters that, for example, minimizes the criterion described by equation (3) as:

$$\sqrt{\frac{\sum_{i=1}^{n}(C_I[i] - C_I^{Observation}[i])^2}{n}}, \qquad (3)$$

where $C_I^{Observation}[i]$ the $i^{th}$ is interpolated insulin concentration in the time window and $C_I[i]$ is the corresponding $i^{th}$ simulated concentration. There are other minimization criteria one may use and depends on the problem requirement. The problem at this stage from numerical solution perspective is a standard problem. The problem is solved by using one of the many optimization routines available as indicated by the body of the application. In this example an optimization routine called "fmincon" from software package called MATLAB® can be used, such as call to and provided from one of the core applications 54 (FIG. 3). The "fmincon" function finds a constrained minimum of a function of several variables. The constrained minimization function then solves for the unknown parameters, which results in the following parameter solution: $\alpha=1.28$, $\beta=31.1$ min, $\tau=56.7$ min, and K=1.93.

Following step 120, the process 100 advances to step 122 where a model validation process is performed on the one or more patient-models selected at step 120. In the illustrated embodiment, the client computer 14 and/or server computer 12 is operable to carry out step 122 by accessing one or more model validation software packages from the model validation module 74. The validation module 74 uses the entire parameter solution provided in step 122 along with the protocol used on the selected patient model for this validation.

Following step 122, the process 100 advances to step 124 where the client computer 14 or server computer 12 is operable to determine whether the one or more patient models selected at step 120 have passed the model validation step 122 and is/are therefore valid patient models. If not, algorithm execution advances, in the illustrated embodiment, back to step 120 so that one or more new patient models may be selected. Optionally, as shown in FIG. 4, the process 100 may include an additional step 126 between the "NO" branch of step 124 and step 120. In this embodiment, the client computer 14 or server computer 12 is operable at step 126 to identify only the portion of a model (or models) and/or model parameter values that require modification. Thereafter at step 120, only the identified portion of the patient model need be selected at step 120 and/or only the identified model parameters require modification.

A third entry point into the process 100 exists between the "YES" branch of step 124 and the subsequent step 140. It will be understood that the third entry point may also function as an exit point from the execution of steps 120-126. In any case, the "YES" branch of step 124 and/or the entry point 3 advances to step 140 where the patient-specific data that has been collected over an extended time period pursuant to steps 102-108 is applied to the one or more validated patient models resulting from steps 120-126 to determine one or more patient therapies or therapy actions. Step 140 may be carried out via the client computer 14 and/or the server computer 12 using any one or more of the analysis tools accessible via the analyses module 76 as described hereinabove. The one or more patient therapies or therapy actions may be or include, for example, but not limited to, administration of one or more drugs, a recommendation of exercise, and/or other therapies and/or therapy actions as described hereinabove.

Following step 140, the process 100 advances to step 142 where a validation analysis is carried out with respect to the one or more patient therapies and/or therapy actions resulting from step 140. In the illustrated embodiment, the client computer 14 and/or server computer 12 is operable to carry out step 142 by accessing one or more results validation software packages from the results validation and presentation module 82 as described hereinabove. Following step 142, the process 100 advances to step 144 where the client computer 14 or server computer 12 is operable to determine whether the one or more patient therapies and/or therapy actions determined at step 140 have passed the therapy validation step 142 and is/are therefore valid therapies and/or therapy actions. If not, algorithm execution advances, in the illustrated embodiment, back to step 140 so that one or more new patient therapies and/or therapy actions may be selected. Optionally, as shown in FIG. 4, the process 100 may include an additional step 146 between the "NO" branch of step 144 and step 140. In this embodiment, the client computer 14 or server computer 12 is operable at step 146 to identify one or more portions of the one or more patient therapies and/or therapy actions that require modification. Thereafter at step 140, only the identified portion or portions of the one or more patient therapies and/or therapy actions need be modified at step 140.

A fourth entry point into the process 100 exists between the "YES" branch of step 144 and the subsequent step 160. It will be understood that the fourth entry point may also function as an exit point from the execution of steps 140-146. In any case, the "YES" branch of step 144 and/or the entry point 4 advances to step 160 where the one or more patient therapies and/or therapy actions is/are presented to the user of the system 100 via one or more presentation devices and/or formats as described hereinabove. Step 160 may be carried out via the client computer 14 and/or the server computer 12 using any one or more of the presentation software packages accessible via the results validation and presentation module 82 as described hereinabove.

SPECIFIC USE CASE EXAMPLES

Example A

The following is a use-case example of some of the concepts described herein. The steps of this example generally follow the algorithm 100 of FIG. 4, and may be implemented via a conventional wizard, i.e., a computer user interface via which the user is led through a sequence of dialogs to accomplish a task. The wizard is a mixture of information gathering and classification of the diabetic patient with the goal to navigate the healthcare professional toward (i) the end goal of therapy determination, and/or (ii) intermediate outcomes as shown in the flow chart of FIG. 4. The example below will be presented in the framework of steps executed by such a wizard, although it will be understood that the steps of this example may alternatively be implemented via a conventional recipe or set of instructions.

In this first example, the case history file and current status of the patient is as follows. The subject is a diabetic Type I patient who's last visit to the healthcare professional was 4 months ago. The subject is a 40 year old male, weighing 80 kg (no change since last visit), and is currently using a fast-acting insulin, such as Lispro (no change since last visit). The subject reportedly measures bG on an average 3 times per day (no change since last visit). Mean Meal amount values for previous visit are 35 g, 70 g, 85 g, and 25 g, and current meal amount values are unknown. The subject's carbohydrate-to-insulin ratio is 8 gm/U (no change), and insulin sensitivity is 40 mg/dL/U (no change). The subject's physical activity is normal (no change). At the subject's previous visit, his HbA1C was 7.5, and it is currently 9.5. Under this fact pattern, the healthcare professional is directed to follow a classical data collection protocol for typical Type I diabetics.

In step 102, the user is prompted by the wizard to select the diabetes type of the patient. The choices are either Type I, or Type II. In this example, the selection is Type I. Next, the user is prompted by the wizard to select the reason of the visitation. The choices available are: new patient, clinical trial, regular visit which is normally 2-3 months visit, post hospitalization or intensive monitoring completed. In this example, the selection is regular visitation The wizard then prompts the user for the follow inputs and, if available, takes the following actions through standard message/data retrieval protocols: enter patient height, weight, gender, age; obtain relevant lab reports (A1C, LDL, HDL, BP, Medication); download data from relevant devices: meter data, pump data, PDA, and the likes; capture patient behavior (from data collected, lifestyle capture), such as for example, number of hypoglycemia events, number of hyperglycemia events, meal timing distribution, carbohydrate composition, insulin distribution, physical activity, sleep schedule, and work schedule; exclusion criteria; input physiological state (illness, no illness); input medication; CSII; MDI; current therapy; and current therapy rules. In this example, the collected data reflects that: current HbA1C=9.5; Last HbA1C=7.5; (last mean values 35 g, 70 g, 85 g, 25 g); current meal information unknown due to lack of entered data; bG measurements are few; bG mean and SDs are: (150+/−70); and that overnight fasting is unknown as well as remaining data values.

Based on the above entered/collected data, in step 104 the system then checks the data integrity/data quality. In this example, since being a regular visit, the healthcare professional had previously determined that regular tuning of patient therapy is needed as a therapy goal. Accordingly, during this step various aspects are examined. For example, for some selected therapies goals there are prerequisites data collections needed in order to provide a meaningful result towards accomplishing the selected therapy goal. Accordingly, in this step the system check to see if data is available in the collected data that is also sensible (e.g., in a predetermined range, above/below/is a certain value, etc.) for particular algorithm parameters. In addition, in step 104, the data content is analyzed statistically to determine frequency of measurements per day, meal time range, meal bolus range, average bolus magnitude with respect to meal size, and so on. The data time series in the collected data is also examined. The idea is that patient normally follows a day to day pattern consisting of activities including meal, physical activity, and work schedule. As per the patient's lifestyle physical activity information, meal information, measurement sequence and dosing information collected by the patient, the detail such information will vary on any given day. This varied information when analyzed over a period of time provides an indication of therapy effectiveness. In one embodiment, such information collected by the patient is examined with respect to a desired patient's lifestyle and at least a minimum of information that should be collected.

Logical deductions are inferred after data analysis and data mapping to address: (a) relevance of a next set of analysis, (b) a confidence interval for a result; and a (c) threshold based acceptance/rejection criteria. For example, in one embodiment, if the event medication and its influence on bG is considered, the first step is to determine whether the data has been collected per protocol. It is to be expected that the bG data to have variability both in magnitude as well as in the time of measurements. In one embodiment, the number of measurements, sequence of measurements and the variability in the measurement are checked against empirical rules to determine acceptance of data. In another embodiment a set of empirical rules are applied to determine which of the collected data is below a threshold based acceptance criteria in order to perform certain analysis in achieving a desired goal. For example, for the above given case history example, from the available data and expected quality of control, one output of the empirical rules will show that the bG measurements needed for post-prandial glucose control are highly relevant to the goal of tuning the patient therapy and that the collection of a minimum bG measurements is need in order to provide useful recommendations to achieve that goal. If the collection of bG measurement are below the minimum, then in step 106 the data collection quality will fail in this example.

After performing the checks in step 104, a series of therapy assessments/recommendations for the patient is optionally provided in step 105. A relevance rating is provided next to each therapy assessment/recommendation that is based on the effect selection of such a therapy assessment/recommendation based on the collected data quality will have on generating changes to the patient's therapy. In the given example, such therapy assessment/recommendation and their associated relevancy may include: (a) Patient therapy collection is poor (Relevance 95%), (b) Patient needs regular therapy tuning (Relevance 50%), and (c) Patient lifestyle change (Relevance 15%). For recommendation (a), the output of the empirical rules leads to a conclusion that the from the collected data A1C is poor, patient feels poorly, readings indicate large glucose values, many hyperglycemia and hypoglycemia incidents, and not enough bG measurements to effectively tune the patient therapy. Accordingly, the high relevance rating is based on the considerations that the new collected data is limited and the old data is about 4-5 months old. For recommendation (b), as mentioned above, to tune the patient therapy, A1C needs to be weighted with a sufficient number of pre-prandial glucose measurements and post-prandial measurements. The method also weighs in hyperglycemia and hypoglycemia incidents, and the A1C value. However, since not enough bG measurements are present in the collected data there and A1C is unsatisfactory, the relevancy for this recommendation is low, and thus probably not the best choose given the scope of the collected data. When the patient is able to provide more bG measurements, the relevancy of this recommendation would then increase. For recommendation (c), looking at the changes in a patient's lifestyle (e.g., medication, moving/traveling to a new time zone, changing physical activity, changing stress levels, or changing meal intakes), by mainly comparing historical data by comparing average values and or using moving windows and comparing average values and or determining trends in the data, at this point due to poor data collection would provides little if any value to the healthcare professional in making adjustments to the patient's therapy.

It is to be appreciated that a whole host of therapy assessments/recommendations could be provided based on the various data collected. For example, such therapy assessments/recommendations could include that the patient is a newly diagnosed Type I diabetic and needs therapy, or that the Type I patient is recruited for closed loop clinical trial. In the given example, such recommendations have a 0% relevance since neither the patient is a new type I nor been recruited for closed loop clinical trial. These therapy assessments/recommendations generated are then presented as output in step 105 for selection by the healthcare professional. In the provide example, the healthcare professional selects therapy assessment/recommendation (a) which is that the patient therapy collection is poor. Therapy assessment/recommendation (b) and (c) may be useful to the healthcare professional on some level but the relevancy rating makes clear that the overall data is lacking in the collected data and is not good enough to generate a new therapy.

Next, after selection of one of the listed assessments/recommendation, a data availability status is then provided to the healthcare professional for selection also in step 105. In this step, the system also determines for the selected assessment/recommendation (here in this example, therapy assessment/recommendation (a)), which further types of actions if taken are relevant to addressing/resolving/improving the selected therapy assessment/recommendation. In this example, the following data availability statuses are provided for selection: (i) collect data to improve post-prandial glucose control (Relevance 80%), (ii) collect data to improve target glucose during fasting (Relevance 75%), (iii) collect data to get overall initial therapy parameters (Relevance 70%), (iv) alter therapy timings such as due to time zone change (Relevance 25%), (v) alter therapy to adjust increased physical activity, alternate state (Relevance 15%), (vi) alter therapy to adjust to alternate physiological state (Relevance 5%), and (vii) identify parameters for close loop algorithm (Relevance 0%). In this example, further empirical rules determine from the collected data and selected assessment/recommendation that to best improve post-prandial glucose control and in order to be helpful in changing the therapy that more such data needs to be collected and such data is the most relevant to achieving that goal. However, in this example, the healthcare professional considers and selects option (iii)-collect data to get overall initial therapy parameters deciding that it is better to start from a standard solution.

From the various selections, the collected data is thus non-compliant and fails in step 106. For example, in this particular embodiment, in order to tuning the patient therapy HbA1c needs to be weighed with pre-prandial glucose measurement and post-prandial measurement. However, since to few glucose measurements are available in the collected data for the algorithm to effectively use, this lack of needed data will result in the data quality failing in step 106. The wizard then executes step 108 where the system via another set of empirical rules identifies data which needs to be re-collected in order to provide sufficient data for the initial therapy parameters needed to tune the patient therapy as a recommended therapy plan or prescription. The prescription may address one or more of the following: (a) number of bG measurement, (b) carbohydrate counting, (c) timing of measurement; (d) notification on a device, (e) training recommendation, (f) compliancy satisfaction criteria, (g) next visitation time—the protocol can dictate a date or duration, and (h) potential entry point at next visit. In the given example, the prescription output provide in step 108 is: 3+ bG pre-prandial measurements per day are needed to satisfy compliancy, count of all ingested carbohydrate shall be documented, notification on a device per doctor insistence, recommend carbohydrate counting help guide (or a training/refresher class), next visitation is 3 weeks from the current visit date, and entry point 1 should be when the patient comes for next visit.

After step 108, the wizard optionally checks to see if the data identified is to be re-entered in step 110. If so, then the wizard repeats step 102 for the identified data. If not, then the wizard at this point continues with the algorithm 100 at Entry Point 2. The issue for the healthcare professional is still whether the patient has good therapy parameters that have not been resolved. Although, the previous collection steps has indicated a lack of necessary data and has presented to the patient the needed data collection requirement to improve performance, in step 120 the user in this illustrated example is presented with the options: (a) to continue with the same parameters, (b) to use historical data, or (c) to reinitialize the data for examining the current therapy parameters. It is to be appreciated that optional steps 105 and 110 can be selected (together or individually) for use during set-up of the software, which has occurred in this example.

In step 120, a relevance algorithm provides the relevancy of each option in being useful to resolve the question of whether the patient has good therapy parameters. In this example, the option of using the same parameters (option (a)) is 0% since the previous steps have indicated that the data quality was poor, and that the options of using historical data (option (b)) and reinitializing the data (option (c)) is 60% and 80%, respectively. To provide each option's relevancy, the relevance algorithm at step 120 in one embodiment is considering the following information: patient data not sufficient to redo therapy parameters; patient's historical data is available; and therapy initialization models are available. The relevance algorithm weighs out the patient glycemic control to determine therapy parameters and also how the patient did with the initial estimate of therapy parameters when the patient was first analyzed by the system. The system, however, allows the healthcare professional to use their own judgment at each step since the system at times may be overly conservative or aggressive for the current patient. In this example, the healthcare professional selects option (c) "re-initialize data" in step 120, which results in the analysis and indication of the model being valid in steps 122 and 124. These steps simply stated means that population based parameters were selected by healthcare professional, and this by default represents mean population behavior with which the healthcare professional is in agreement considering the current state of information.

The wizard after step 124 continues with the algorithm 100 at Entry Point 3. In step 140, the process 100 in this embodiment applies the collected data to population based parameters to determine a patient therapy, and which are shown in Table 1.

TABLE 1

Therapy parameters generated from the Model

| | |
|---|---|
| Basal rate | 1.1 U/h |
| Carbohydrate to insulin ratio | 9 gm/U |
| Insulin sensitivity | 30 mg/dL/U |

In step 142, the wizard now performs a validation analysis on the determined patient therapy and provides the healthcare professional the most relevant options by which to review the determined patient therapy and to provide therapy safety guidelines. The healthcare professional in the given example is provided with the option to evaluate life style impact on the patient's management of the chronic disease. In addition, regarding therapy safety guidelines, based on the collected data and lifestyle results, the healthcare professional is notified in step 142 that the patient has a potential for x hypoglycemic episodes and y hyperglycemic episodes, whereby hyperglycemic episodes can be brought down by additional post measurement and corrective insulin. The system also recommends in step 142 a therapy based on the parameters generated from the selected model. In this example, the recommended therapy provides setting the basal rate to a desired U/hr, setting the carbohydrate to insulin ration to a desired gm/U, insulin sensitivity to a desired mg/dl, indicating a needed number of bG measurements, requesting carbohydrate counting an all meals ingested, and indicating that at least x daily pre-prandial measurement and at least y postprandial measurement are needed to improve therapy parameter estimates. Additionally, the user is advised that the patient should complete the data collection for the therapy in the next y weeks and visit the healthcare professional thereafter. In step 144, the healthcare professional is asked by the system whether the recommended therapy is valid. Should the healthcare professional wish to change any of the above aspects of the recommended therapy, then indicating "no" in step 144 results in the healthcare professional being able to modify a portion of the therapy in step 146. After making desired changes in step 146, steps 140-144 are then repeated. Otherwise, the process 100 finalizes the recommendation therapy by outputting it as a prescription in step 160, which is also entry point 4. It is to be appreciated that for this example, when the patient again visits the healthcare professional, the wizard is again employed at entry point 1 and navigates the user through the algorithm 100 of FIG. 4.

Example B

In a second use case example, the case history of the subject is as follows. The subject is the same diabetic Type I patient in Example A above and whose last visit to the healthcare professional was 24 days ago. The subject is a 40 year old male, weighing 80 kg (no change since last visit), and is currently using a fast-acting insulin, such as Lispro (no change since last visit). The subject measures blood glucose (bG) on an average 6 times per day (3 times per day as of last visit). Mean Meal amount values for previous visit are 25 g, 85 g, 85 g, and 25 g, and current meal amount values are unknown. The subject's carbohydrate-to-insulin ratio is 8 gm/U (no change), and insulin sensitivity is 40 mg/dL/U (no change). The subject's physical activity is normal (no change). At the subject's previous visit, his HbA1C was 9.5, and it is currently 9.5. Under this fact pattern, the healthcare professional is directed to follow an intensive monitoring data collection protocol for typical Type I diabetics.

After completion of step 102 in this example, the following data has been collected: patient Type I; visitation reason is intensive monitoring completed; current A1C=9.5; last A1C=9.5; current meal information (mean 35 g±5, 70 g±15, 85 g±20, 25 g±15); last meal information unknown due to lack of data, bG mean and SDs are 135+50; overnight fasting is 130±30 mg/dL; data is processed against the required protocol; and statistically the data collected was done within the bounds of the protocol. After performing checks on integrity and quality of the collected data in step 104, the series of recommendations provided (e.g., displayed) along with their relevancy rating in step 105 are as follows: (a) patient needs regular therapy tuning (Relevance 90%), (b) patient therapy is poor, e.g. A1C is poor, patient feels poorly, readings indicate large glucose values, many hyper incidents (Relevance 95%), (c) patient is newly diagnosed Type I diabetic and needs therapy. (Relevance 0%), (d) Type I patient has been recruited for closed loop clinical trial. (Relevance 0%), and (f) patient lifestyle change, e.g., moving to a new time zone, increase physical activity, etc. (Relevance 65%).

From the above displayed recommendations, the healthcare professional sees that recommendation (a) and (b) are the most relevant, of which a recommendation (b) "patient therapy is poor" has the highest relevance. In this example, the healthcare professional selects recommendation (b) in step 105. Next, the following selectable options on data availability status and associated relevancy is provided (e.g., displayed) in step 105 to the healthcare professional: (i) collect data to improve post-prandial glucose control (relevance 15%), (ii) collect data to improve target glucose during fasting (relevance 10%), (iii) collect data to get overall initial therapy parameters (relevance 10%), (iv) redo patient parameters and determine therapy parameters (relevance 95%), (v) alter therapy timings, e.g., such as due to time zone change (relevance 25%), (vi) alter therapy to adjust increased physical activity (relevance 0%), (vii) alter therapy to adjust to alternate physiological state (relevance 0%), and (viii) identify parameters for close loop algorithm (relevance 0%). At this step, the healthcare professional selects option (iv) redo patient parameters and determine therapy parameters as the relevant course of action. It is clear that the past visit initialization shows glycemic control is poor. The pre-prandial indicates poor meal control and/or fasting control even though patient is doing a diligent task of getting measurements and counting carbohydrates. Patient specific tuning is needed as opposed to the previous visit wherein population based parameters were provided. Since data collection as per baseline is thus compliant and thus passes in step 106, the process 100 continuation at entry point 2 for model selection.

In step 120, the process 100 provides a determination that the collected data is available and it is satisfactory, historical data is also available, and that an empirical initialization model is also available. The healthcare professional is thus provided in this context in step 120 with the following options and their associated relevancy: (a) identify patient parameters (relevance 95%), (b) use historical data (relevance 50%), and (c) reinitialize data (relevance 50%). In this example, the healthcare professional selects the option (a), which is to identify patient parameters. The healthcare professional could have selected the approach of using historical data wherein patterns and trends are analyzed and presented. However, in this example with detailed data available, the healthcare professional opts for a detailed step of examining patient specific physiology characteristics. Next in step 120, the following identified model parameters are displayed along with their assessed relevancy as the options selectable by the healthcare professional: (a) meal related model+CSII+bG meter (Relevancy 99%); meal related model+MDI+bG meter (Relevancy 0%); and meal related model+CSII+Continuous (Relevancy 0%). In step 140, the healthcare professional selects the first option (a), which is meal+CSII+bG meter on the wizard. Here, relevance shows that overall therapy is needed. Meal is the major exogenous disturbance for the patient. Exercise or other stressors are weighed out at this point as secondary, and may become relevant in future tuning of therapy parameters.

Finally, in step 120, the wizard presents for selection the type meal model: (a) Fast (carb dominated); (b) Medium (nominal); (c) Slow (high fat content), and (d) Mixed (data collected accordingly shall have such information). The healthcare professional selects the second meal model option (b), which is the medium or nominal meal model. Here, the data is not rich enough or documented well enough to do mixed case under option (d), and the patient's data has indicated the baseline nominal model. Specific meal habits may be captured with more detailed information. The meal model section may be, or include, a more detailed process, and in any case leads to the selection of underlying mathematical models which may be standard or generalized by allowing healthcare professional to select or define alternate physiological models. The above example illustrates only one way of addressing model selection in step 120.

After model selection, in step 122 the process 100 performs validation and an analysis on the model. For this step, patient specific use case scenarios are simulated in silico on the system 10 via a computer-based simulation. As good as an understanding of the selected patient model may be, each time a mathematical model is determined it should be tested to examine its fidelity. Step 122 ensures that there are checks and balances built into the system 10 since testing special test cases that have been configured to the individual subject, and in which the resulting data is then compared with either known standards or a broader population of data. Step 122 entails at least one of the following as dependent on the specific selected patient model: validating the model in silico over the specified operating range to understand the operating space, and to understand the limitations of the model; providing a reasonable idea of the error underlying the model's given assumptions; applying other testing modules such as test meals, test insulin dose, and so forth; testing the model with clinical data that has been collected, such as insulin input information and event input information; and applying specific model characteristics, such as specified profiles, parameter value ranges, or metrics. Any abnormality or odd aspects are flagged and presented to the healthcare professional for action.

In the given example, a patient model fitting is done which has a quality of fit=85%, i.e., the model and the set of parameters will explain 85% of the model characteristics, which is a weighted result of the observed characteristics (measurements of bG and meal amounts). In other embodiments, confidence intervals for the parameters may be available. Also in this example, a mock patient model response is done to verify physiological characteristics (verification) of the model. This is also referred to as patient model characterization, which includes standard testing of the model to predetermined signals to examine obtained characteristics, which are then compared against one or more expected ranges of observed patient characteristics. One goal at this point is to stay within the specified boundaries of acceptable patient characteristics. The model's capability to replicate results (quality of prediction) may also be done in other embodiments. This is an optional feature, and may be conducted when replicate data sets are available. The measure of this capability may be, for example, a normalized least square fit.

After completion of the analysis on the selected model in step 122, in step 124 a determination as to whether the model is valid is carried out. In step 124, the healthcare professional reviews and contemplates acceptance of the model based on results which includes at least one of the following: confidence interval on the parameters, ability to fit the data, providing estimates of physiology based parameters with confidence interval, and the like. Confidence intervals may be computed for each of the parameters. These confidence intervals basically determine confidences with which these parameters have been computed. Excessively broad confidence intervals are not expected as the model has been chosen for the particular protocol. But if it happens that they are overly broad, it can be concluded that for this particular patient and this particular meal, there is no improvement possibility with this method. Also, the goodness of fits may be checked using classical criteria like squared difference between prediction and measures. If the goodness of fit is poor, the computed parameters should not be used to improve meal control. This step can be redone if the model does not do a good validation job. Additionally one may want to do comparison with another model or models to determine whether there is an alternate model or models that provide for better results. As a result of the validation analysis performed on the selected model (i.e., identify patient parameters) in step 122, the healthcare professional determines in step 124 that the model is valid. The wizard at this point continues with the algorithm 100 at Entry Point 3.

After the healthcare professional has approved the model, the wizard then takes the healthcare professional into the final phases of therapy analysis/determination. In step 140, the process performs in silico simulations to challenge critical cases for therapy robustness and assessing the stability of the solution by taking into account the monitoring schedule and fail safes, determine the sensitivity of the therapy to parameter variation, generate a confidence interval by performing a large number of simulations, and determine effectiveness (efficacy, potency, affinity) of various therapy to determine a recommended therapy suggestions (including safety and tolerance of the therapy).

For example, in step 140, the process 100 in the given example extracts/identifies patient lifestyle data and, based on such data, provides therapy results with confidence interval(s). Patient lifestyle is relevant here for testing and evaluating a therapy. The collected information and identified model are now presented to the healthcare profession via the wizard with lifestyle options to review therapy outcomes. Here, one goal is to provide therapy safety guidelines. The healthcare provider may be provided with the following therapy computation options in step 140: (a) determine therapy parameters for a specified algorithm A (e.g., CSII) and specified lifestyle; (b) determine therapy parameters for a specified algorithm B (e.g., ICT) and observed lifestyle; (c) suggest high performing therapy (CSII+frequent measurement+lifestyle); and (d) evaluate life style impact (95%) with poor compliancy 50% versus 90% compliant. In step 140, the healthcare professional selects the first option (a) since the patient had been non-compliant in the earlier visit. Optionally, an additional exercise that may be conducted by the healthcare professional is to also select the fourth option (d).

Here, using the observed lifestyle but running through a non-compliant scenario (i.e., the patient is not observing the therapy rules and/or is not-compliant to measurements and carbohydrate counting), a stochastic simulation is carried out in step 142, and a comparative report is generated of the potential outcomes. Such a report may include: patient has potential for x hypoglycemic episodes and/or y hyperglycemic episodes; anticipated HbA1C at next visit (e.g., 3 months from now); highs and lows bG measurements; potential time lost and sick days due to mismanaged diabetes treatment. Additionally, recommendations with the therapy may be: patient measurement lifestyle should be at least x measurements; hyperglycemic episodes can be decreased by additional post-measurement and corrective insulin; patient should continue to have pre- and post-meal measurements; and as patient has varied meal eating habits, collect and record data around special meal types so that further therapy can be improved. In addition, compliancy, for purposes of this simulation, in terms of a compliancy ratio, may also be given wherein the compliancy ratio is equal to the number of times an event is actually recorded divided by the number of times an event is to be recorded.

For example a patient has a record of 103 pre-prandial breakfast measurements, and the time period over which the measurements were done is 120 days. The compliancy ratio for breakfast is therefore 103/120, or 0.86. Then, as an example, a required breakfast fasting compliancy of 0.8 or better is met in this case. The healthcare professional reviews this report and therapy in step 144, and if no changes, finds it valid. The process 100 now at entry point 4, outputs the report and therapy recommendation in 160 as a prescription, and updates the patient's record electronically. Specific system implementations according to the represent invention and uses thereof are provided hereafter with reference made to FIGS. 2-9. How the system and process of the present invention response to an event is discussed hereafter.

Invoking Software Responses via an Event

As mentioned previously above an event is a unit of information generated by one component which can be used by another component of the system. Intrinsic to an event unit is the time of the event, an event characterizing descriptor, an event action schema, and an event value. Further details are provided latter. An activation of an event in the system has to do with specifying values for the elements that make the event. An event in one embodiment can be: (i) an information entry, (ii) activity information, (iii) commanding device to do something, (iv) informing a patient to do a task, (v) informing a patient of a potential physiological state, and so on. The structure of the event in one embodiment has the following fields: absolute event time; type of event; duration/action time/activity time of the event; relative to parent the start time of the event; amount, (intensity) of the event; and advisory string. The absolute event time provides when an event should occur, and has the following values: predetermined, determined by an algorithm, or asynchronously triggered. The time of the event is provided as absolute time which in general acts as the absolute reference. In special cases the absolute event time is linked to absolute time of another event. The absolute UTC time is used as the "reference time" to which the event is associated. The reference time is essential in correlating other events. And a unique time determination is not trivial considering the multiple time zones and day light saving. A distinction between Local time and Coordinated Universal Time (UTC) is relevant. Local time is used for display purpose and UTC is mapped to the Local Time.

Type of event describes what event has been excited, and has values such as meal, exercise, medication, insulin measurement, alternate state, corrective event, and cancels an event. Duration defines the length of effect an activity, such as insulin bolus activity, a meal activity, an exercise activity duration, and alternate state. Any activity initiated should be bounded by duration. By default an activity has infinite duration. The other default possibility is that the activity has no duration. It means its impact was is instantaneous. A nonzero value from 0 to infinity captures all the intermediate cases. Relative time is with respect to the absolute reference time the event is initiated at an absolute time adjusted with respect to the relative time. This could be for a meal related bolus activated at time which is equal to an absolute event time plus a relative time, measurement relative to meal event, or measurement relative to last bG measurement. Amount describes the intensity or magnitude of the event, and can be for amount of insulin, a size of a meal, and a speed of meal. Finally, the advisory string is a terse but narrative part of the information. In one embodiment, this field is outputted in XML or RTF or other mark-up language to present a more detailed and descriptive information specifically tuned for the end user and database record. Generally, the advisory string is a commentary of the ongoing activity on past, current and future task. The utilization of using tagged language in this field enhances the overall ability to provide the user with all potential tools to interact such as audio, visual graphics, static and dynamic links. The dynamic links can include progress bar, bar charts and so forth. For example time to activity can be represented by progress bar, insulin dispensed from amount to be dispensed could be shown as progress bar and so on.

Note characterizing the event input in the above manner, the following utilities in the system may be provided: command a medication dispensing unit (insulin pump) to dispense medication (insulin) with given input characteristics; command a measurement unit to perform measurement task with given input characteristics; receive set of instructions from the patient about an imminent event activity input characteristics; and present an event input to the algorithm modules (i.e., software components of the system that contains the Glycemic-Control Algorithm) and/or raise an output event. The Glycemic-Control Algorithm is used to make insulin recommendations based on collected subcutaneous sensor data, the subject's predefined basal profile and user inputs to maintain the subject's glucose levels within a target range. Present protocol specific schedule to (i) device (ii) algorithm and (iii) user to perform tasks/events. Store characteristic input and retrieve characteristic input from the database. Each of the above mentioned utilities is further explained using examples of how the system and software of the present invention functions.

Command a Medication Dispensing Unit to Dispense Medication with Given Input Characteristics In this embodiment, the patient data measurement/collection device 48 (FIG. 2) is a medication delivery unit, e.g. a programmable insulin pump, which operates automatically to the recommended therapy of the system as assigned as a prescription by the healthcare professional at the end of step 160 (FIG. 4) and uploaded via the client computer 14. The event itself is generated in one of many ways: (i) algorithm, (ii) user, (iii) watch-dog (3 party tools), (iv) fail safe, (v) database triggered events, and (vi) protocol based. The characteristics needed to uniquely and shall need to cover a known or an unknown length of time before next communication can occur. Timing of medication is central to diabetes therapy (all events timing is preferably maintained in UTC time with appropriate adjustment for local time). Type of event explains the context of the event and/or describes the event triggered (For example meal bolus, commanded bolus, meal bolus profile). Any activity initiated is in general bounded by finite duration. The duration is understood to cover the actual duration of the event enacted like dispensing a commanded bolus takes physically a finite time to deliver and this duration may be relevant for algorithm to consider when deciding the next bolus command or one can capture duration of the insulin to be the duration of insulin activity in the patients' body. The relative time allows the event to be staggered with respect to a reference point. For example if the reference time is the time of the meal then the relative time is utilized to have pre meal dose for example by specifying negative time in minutes. A sequence of such numbers further extends the single dose schema to a distributed sequence of doses relative to the meal time. Amount which can refer to intensity of an activity or it represents quantity/amount. For example, in this particular case the amount of insulin to be dispensed. Like duration it can also be a sequence of numbers. The number of elements in the sequence will normally match with that for the number of elements in the relative time. Advisory string presents the information in (i) graphical, (ii) audio format. Additionally, the information if stored presents a log of the activity.

Command a Measurement Unit to Perform Measurement Task with Given Input Characteristics Measurements are needed for manual control or for an automated feedback control to achieve good performance. Then from functional viewpoint measurements are generalized as another event unit. Of course measurements have considerations such as associated cost, limitation in how many measurements can be made in a realistic sense, how measurement are used dictates the sequence of measurement, measurements may also be related to protocol to accomplish a task, measurements are needed to improve performance, measurement advisory adds value by assisting the user, the Healthcare Professional (HCP) (e.g., physician, RN, LPN, or paramedic/EMT), the emergency support team with ideal time to measure, best minimal time to measure and maintain safety. The various possibilities are covered by the event characteristics mentioned above and are readdressed for bG measurement. Timing of measurement is central to providing good therapy. Measurement when performed is preferably captured in the UTC and submitted to the algorithm and or database. Additionally, measurement advisory is presented in local time. For example, in one embodiment, the patient data measurement/collection device 48 is programmed as described above to tell the patient in absolute term when the measurement should be done in local time according to the prescription output by the system. For this utility, type of event explains the context of the event and/or describes the event triggered. For example, bG Spot measurement represents a bG meter used for measurement, a blood draw will represent blood sample for analysis such as obtaining bG measurement, insulin plasma concentration or A1C measurement. Any activity initiated is in general bounded by duration. The duration is understood to cover the actual duration of the event enacted like measurement takes physically a finite time to determine glucose concentration and this duration may be relevant for algorithm to consider such as in continuous measurement one can have measurement delays of small to as much as 30 mts delay. There are cases wherein duration may not be meaningful and in such a case the entry is left blank. The relative time for measurement can be made to cover many use case scenarios and may be contextual. The relative time can act as a count down or time remaining to do measurement. It can represent the time lapse since last measure. It can represent time since the desired time of measure. It can represent a sequence of time for measurement for protocol based or event based measurement requirements which may consist of a sequence of measurements at specified time durations. Amount which can refer to intensity of an activity or it represents the quantity. For example, in this particular case the amount represents the measurement value. If the device 48 is provided with a bG measurement unit, the device can display the measurement, and in case where measurements time is specified and measurements have not yet occurred, logic to manage the future entries and/or missing entry can easily be provided. Lastly, the advisory string can present information both a graphically and audio format. Additionally, all information is now stored as a log of the activity.

Receive Set of Instructions From the Patient About an Imminent Event Activity Input Characteristics In general events need to be characterized to get better performance. Currently, meals for example, only carbohydrate counting is utilized. In such a case the amount field of the event captures the net strength of the meal. However the fuller feature such as its speed or its glycemic index is not addressed. The duration field of the event can be used to capture one of the aspects of the meal speed. The meal event maybe further described as fast, medium or slows to again capture the speed of the meal. Another example is exercise where the intensity and duration can help capture the activity level. These and other examples can be used an algorithm of the process 100 to fine tune how background insulin should be adjusted in providing a recommended therapy. The relative time field in case of exercise allows one to preprogram an event which the algorithm of the process 100 can use to fine tune insulin in advance to match up with the upcoming event. This is very helpful in enhancing performance of a therapy since there are system and response delays.

Timing of ingesting a meal, physical activity such as exercise or being in an alternate state such as stress is needed to make a therapy adjustment. The identification of such activity could be manual and in this case the event is triggered by manual entry. All events timing is preferably maintained in UTC time with appropriate adjustment for local time. Type of event explains the context of the event and/or describes the event triggered. For example meal can be described as high or low glycemic index, it can characterized by composition such as fat, protein, carbohydrate, fiber or by descriptors such as fast medium or slow meal. Any activity initiated is in general bounded by finite duration. The duration is understood to cover the actual duration of the event triggered. For example knowing the duration of meal activity is relevant for slow absorbing meals. Knowing the duration helps in determining the insulin distribution. Similarly other event characterizing selection enhances the knowledge of the anticipated physiological load which is used by algorithm to address therapy needs.

The relative time field allows the event to be staggered with respect to a reference point. In clinical studies it is clear that advance knowledge can further enhance the performance of the controller. Insulin therapy based on the anticipated action insulin can be cut back or pre-dosed. Generally for an anticipated exercise basal insulin is cut back and in addition the algorithm will raise a carbohydrate ingestion event so as to maintain glucose within the euglycemic range. In fast absorbing meals pre dosing also helps to curb the fast rising glucose. The amount field can refer to either intensity of an activity or quantity/amount. For example, in case of strenuous exercise will refer to the intensity of the exercise event and in case of meal it can be described by amount of carbohydrates. Like duration it can also be a sequence of numbers. The number of elements in the sequence will normally match with that for the number of elements in the relative time. Advisory string presents the information in (i) graphical, (ii) audio format. An advisory string in the instance of exercise is advice to patient to consume fast acting carbohydrates to compensate for the physical load and thus need for carbohydrates. Additionally, the above information of the event if stored presents a log of the activity.

Present an Event Input to Algorithm Modules and Raise an Output Event

An algorithm is a set of instructions to determine an action or a result. The algorithm is a receiver of events, it is a generator of internal events and it is a creator of external (output) events. The algorithm itself is structured modularly so as to allow the treatment of complex problem in a structured manner. The structure focuses in breaking down the problem into functional units which specialize in the given task. The modularity further allows including or excluding effects depending on the problem need. The final behavior is filtered through additional heuristics. So at a higher level each module can be seen as a superposition of effects. But at the core of how each of the module handles is not restricted. Thus the high-level modular functionality is as follows: management and housekeeping; monitoring and status information; handling major events; core control actions (central to providing glycemic control); and corrective actions.

Management and Housekeeping

The management and housekeeping modules are as follows: initialization/preparation; handling missed cycle; event mapping; insulin buckets; component nullification; database; and implement protocol. Initialization/preparation is a state vector that manages the past, current, and future information. Handling missed cycle handles restart of the process 100 or algorithm calls that were skipped for any reason as a fail safe. Event mapping maps the external event set to the internal event set. Insulin buckets manages the insulin recommendation from various modules as components to fill and empty buckets. Component nullification is explained as follows. In general when a solution as the current one wherein the physiology even though the inputs and outputs are net effects of various components when solving the problem (i) as individual components or (ii) grouped modular effects the nullification step allows removal of an effect not required during the consideration of the individual component or grouped modular effect. Thus for example, insulin nullification is negating any insulin components coming from feed-forward terms of the control action from final insulin delivery. Internal bolus management delivers feed-forward boluses that result from a meal event. Internal bolus management allows (i) creation of internal events and (ii) grouping internal events. The management of therapy elements is thereby generalized and allows flexibility of adding or removing an effect depending on the changing needs and availability of new information. Database provided for the retrieval and storage of data, and logging information. Implement protocol is a protocol format designed as per the generic event structure to allow dynamic creation of a protocol activity as desired by the healthcare provider. One aspect of the protocol is to support compliancy for generating minimum information for analyzing, and generating patient specific information.

Monitoring and Status Information

The modules for monitoring and informing status are as follows: glucose update, outdated glucose, self-bolus, meal advisory, protocol advisory, fail-safe, and major event handlers. Glucose update tracks the availability of new glucose measurement values, related to compliancy and measurement needs and generates information for the user. Outdated glucose informs the user if there is a need for a fresh glucose value, again related to compliancy and measurement needs. Information is also generated for the user. Self-bolus accounts for any insulin discrepancy by means of self-bolus commands (internal activity). Meal advisory informs the user to start eating. Compliancy issue which covers carbohydrate intake, and may extends to other monitoring and informing. Protocol advisory informs the user of upcoming or pending activity by generating internal events. Fail-safe systematically informs a responder (e.g., a parent or watch dog service) that the user is turning off the device or system and sets up alarms create time windows during which if the device and/or system is not up or a call is not made to override the alarms, then an emergency dispatch or alternate forms for reaching out is provided for help. Major event handlers are modules for handling major events such as prep-exercise, exercise, commanded bolus, and meal compensator. Prep-exercise reworks the basal requirement in anticipation of the exercise controller, and informs the controller at the onset of specific exercise. Exercise maintains the elevated glucose set point for the duration of the exercise and then returns to its glucose set point. Commanded bolus is a request for additional insulin bolus (user control), and allows asynchronous command. Meal compensator informs the controller of carbohydrate ingestion. Alternate state/trigger events cover alternate state and trigger events.

Core Control Actions

Core control actions modules form the core control actions central to providing glycemic control and are as follows: process sensor data, insulin set point, glucose prediction, insulin recommendation module, exercise compensator, fast-acting carbohydrate ingestion, meal compensator, model selection, model parameter determination/update, patient characterization, managing discrepancy, final delivered insulin, and final recommended insulin. Process sensor data determines a glucose value from available measured glucose values e.g., interstitial fluid values (isf) values obtained through the sensor unit and/or blood-glucose (bG) values obtained through an external meter. Insulin set point is the insulin infusion rate used to maintain target basal glucose (i.e., glucose value achieved for given basal insulin rate). Glucose prediction predicts the glucose value for control cycles utilizing the past glucose measurement values, past insulin measurements, past events and future scheduled events. A missed cycle is whenever the algorithm is not called during a control cycle. Note, glucose can be measured glucose or predicted glucose, as determined by the context in which it is discussed. Measured glucose is the glucose value obtained from a glucose sensor. Predicted glucose is the future glucose value determined from a known glucose value using a model. Therapy target glucose is the glucose value the user wants to achieve. Target glucose/glucose set point is the glucose value the controller tries to achieve asymptotically through feedback. Basal control action computes the insulin dose to maintain basal glucose. The determination is based on models and or rule sets.

Exercise compensator handles an increased physical activity level. The determination is based on models and or rule sets. Fast-acting carbohydrate ingestion handles the ingestion of fast-acting carbohydrates to compensate for an expected glucose drop. The determination is based on models and or rule sets. Meal compensator computes insulin boli distribution for a meal event. The determination is based on models and or rule sets. Open loop basal implementation implements basal insulin during the open loop controller. The determination is based on rule sets. Model selection is the determination of an appropriate model that best addresses the patients need, such as part of the process 100 described above with regards to FIG. 4. The rules are based on life style selection, past events used, future events, and protocol and/or simply based on healthcare professional's selection. Model parameter determination/update determines parameters for the selected model. The determination uses a prior data, data collected by device, parameter determination settings. Patient characterization is when selection of patient specific parameter or using population based model is evaluated. The determined model and parameter go through a number of checks and if the results meet and maintain certain known expectation then the determined parameters are selected else a sub optimal such population based parameter set is utilized for therapy determination, controlling glucose. Therapy parameter determination/update is also as previously described above with regards the process 100 of FIG. 4. Managing Discrepancy manages the insulin buckets when the discrepancy between the commanded insulin versus the delivered insulin is identified. Final Delivered Insulin is the amount of insulin dispensed for the cycle. Final Recommended Insulin is the dose of insulin that is computed by the algorithm and passed to healthcare professional as a recommendation.

Corrective Actions

Corrective actions are modules which can be used to take corrective actions which are as follows: carbohydrate rectification, hi-glucose intervention, lo-glucose intervention, and meal glucose zone. Carbohydrate rectification reworks the previously entered meal event (carbohydrate value), and the insulin delivery is corrected accordingly. Hi-glucose intervention corrects the high glucose level by means of insulin delivery. Lo-glucose intervention corrects the low glucose level by means of ingesting fast-acting carbohydrates. Meal glucose zone defines the glucose target as a band, rather than as a line. In other embodiments other suitable corrective actions may be used.

Present Protocol Specific Schedule to (i) Device (ii) Algorithm and (iii) User to Perform Tasks/Event Protocol is a planned execution of a sequence of events. The adherence to the plan allows (i) improved treatment (ii) be able to use the collected data for a particular analysis and determine a medical action or (iii) a general use case where a lifestyle is planned such as a diet plan, exercise plan, timing of meals, composition of meal. This is relevant in supporting a healthcare provider with just data but data collected with correct timing and associated events such as meal with specific fat, protein and carbohydrate content. A protocol then is a specific sequence of event units composed of bG measurements, bolus commands, meal ingestion, and exercise. The events can be triggered in many modes such as hand held devices are programmed, a simple paper based description which the patient follows, an automated service such as compliance counselor assisting the patient.

Store Characteristic Input and Retrieve Characteristic Input from the Database

Database is the central information storage unit. The database is used to store and retrieve events and user specific setups. The stored events cover past, present and scheduled future events. The database is used in terms of storing event information as log of the ongoing current and past activity, it is used for retrieving past and future events and it is used for triggering scheduled events. Specific implementations of the above described system, process, and software modules is now provided hereafter to further advance an understanding of the invention.

Specific Implementation Examples

Figure 5:
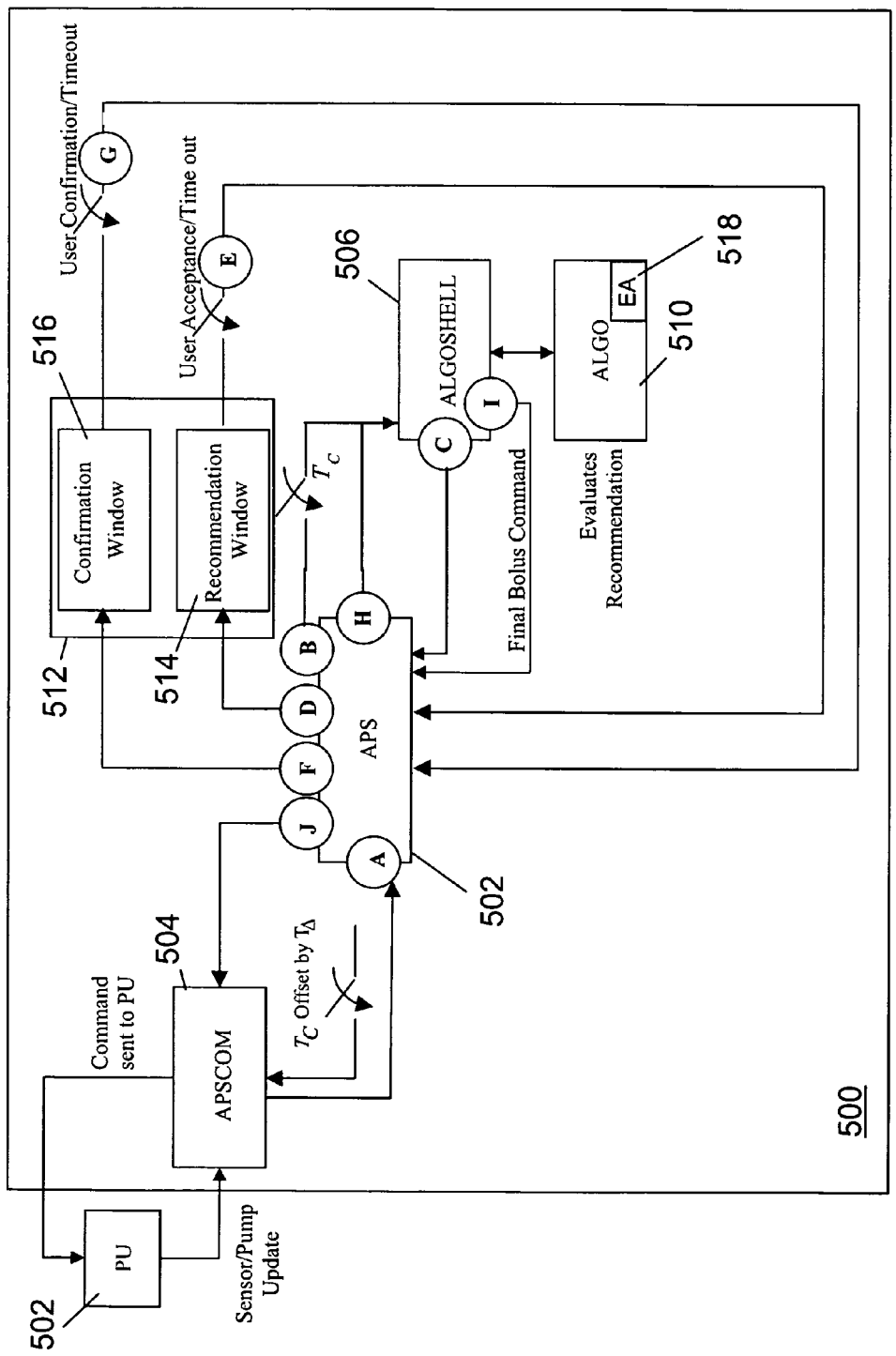
FIG. 5 is a block diagram of software components used in the system of FIG. 2 to provide an Automatic Pancreas System (APS) for developing patient-specific therapies according to an embodiment of the present invention.

The apparatus and methodology described above is unified in the following illustrated embodiments, which enhance the healthcare provider's ability to collect, analyze and determine therapy for addressing a chronic disease such as diabetes. In a first illustrate embodiment employing the DTPS methodology, an Automated Pancreas Test Stand (APTS) program is disclosed. APTS is a software program that is used to control the diabetic subject in a clinical setting. In a second illustrated employing also employing the DTPS methodology, an Automated Pancreas—Control Algorithm Test Suite (APCATS 900) program is disclosed. APCATS 900 is a software program that analyzes a diabetic subject in an emulated environment that is running, for example, on the client computer 14 (FIG. 2). With reference to FIG. 5, the APTS program is discussed first, followed by a discussion on the APCATS 900 program thereafter in later sections.

Automated Pancreas Test Stand (APTS) program

With reference to FIG. 5, the APTS program 500 runs on a conventional computer (e.g., laptop, personal digital assistant (PDA), smart phone, etc.) and provides two independent software components: automated pancreas software (APS) 502 and automated pancreas software communication application (APSCOM) 504. As will be explained in a later section, the APS 502 makes periodic calls to an included algorithm shell (ALGOSHELL) 506 for insulin recommendations, and interacting with APSCOM 504. A discussion on the ALGOSHELL 506 is provided hereafter in a later section. APSCOM 504 is responsible for collecting information from a portable unit (PU) 508, interacting with APS 502 and storing and retrieving information from a database, such database 24 (FIG. 2). In one embodiment, the PU 508 is device 48 (FIG. 2), and in another embodiment is a sensor that measures glucose concentration such as, for example, a Subcutaneous Continuous Glucose Monitor (SCGM), which is a micro dialysis-based device developed by Roche Diagnostics Corporation to make frequent glucose measurements. In still another embodiment, the portable unit 508 is an insulin pump or insulin pump system, such as for example, Roche Diagnostics' Accu-Chek® Spirit insulin pump system. In the insulin pump system embodiment, the APSCOM 504 may communicate with software provided on a PDA that is provided with the insulin pump system, or if running APTS on the same PDA, with the insulin pump control software.

A controller module call ALGO 510 is also provided which determines the insulin delivery schema, and communicates the doses to APS 502 through the ALGOSHELL 506. By schema here, it is meant a time and value pair. The ALGOSHELL 506 performs some of the standard system functionality such as state management, ALGO call screening, unit conversion, and determining the amount to dispense. The APS 502 is responsible for calling ALGOSHELL 506 at periodic interval of time referred herein as a control cycle. The APS 502 also periodically interacts with APSCOM 504. In one embodiment, the APSCOM 504 uses Microsoft© COM technology to communicate with programs such as APS 502 and the database 24 (FIG. 2), which in one embodiment maybe implemented as a Microsoft© Access database. In other embodiments, other communication frameworks and database applications maybe used to implement the present invention, such as the .net framework, Unix, Oracle, SQL, Java, and the like. The APTS program 500 also provides a use interface 512, which the APS 502 uses for displaying data and receiving event information from the HCP and/or the patient.

System Workflow

This section illustrates the workings and workflow of the system, and the various high-level APS-ALGO call sequences that directly pertain to the controller ALGO 510. The sequence of events in the system per a control cycle period $T_C$, corresponds to the circled letters A-J in FIG. 5. APS 502 drives the system in a clockwork fashion, and some of the key time descriptors are detailed in FIG. 5. At event A (time $-T_A$), the APS 502 calls APSCOM 504 and acquires the new sensor data set and the data for net insulin dispensed. Time with respect to a control edge is now set to zero, and at event sequence B, the APS 502 calls the ALGOSHELL 506. The ALGOSHELL 506 then updates the state information, does unit conversion, checks the mode, and calls the ALGO 510 for an insulin recommendation. The ALGO 510 returns the recommendation to the ALGOSHELL 506. The ALGOSHELL 506 makes the conversion, then updates the state and returns to the APS 502. After completion of event sequence B, the ALGOSHELL 506 returns a recommendation to the APS 502 which is event sequence C. This is referred as a SYNC-1 call.

After completion of event sequence C, in event sequence D, the APS 502 opens a recommendation window 514 in the user interface 512 and waits for the user to accept or cancel the recommendation, via use of an input device, such as device 40 (FIG. 2). The APS 502 will await input until recommendation window times out. After completion of event sequence D, the recommendation window returns to the APS 502 for event sequence E. If the user confirmed the recommendation, thus completing event sequence E, then for event sequence F the APS 502 opens a confirmation window 516 in the user interface 512 and waits for user to accept, or cancel the confirmation via the input device (e.g., device 40). The APS 502 will await input until confirmation window times out. After completion of event sequence F, for event sequence G the confirmation window returns to the APS 502. Then for event sequence H, the APS 502 calls the ALGOSHELL 506 with a dosage amount that is either (a) confirmed by the user, (b) zeroed by user (c) or, in the case of timeout, an amount that meets a threshold requirement, else 0. The second ALGO call is called a SYNC-2 call. Note, the threshold requirement is an agreed-upon recommended insulin dose that is delivered to the subject, unless it is rejected by the healthcare professional. After completing event sequence H, the ALGOSHELL 506 returns the final command amount to the APS 502 for event sequence I, and then the APS 502 issues a bolus command to APSCOM 504 for event sequence J. This ends the control cycle period.

ALGO

This section further clarifies the key workings of the ALGO 510. It is critical to the therapy that the doses are provided in a reliable and timely fashion. In the sections following below the following aspects of the ALGO 510 are addressed: timing aspects—how the index based ALGO 510 determines real time elapsed; memory duration—length of past history (system memory) required to determine new recommendation; missed cycles—how the ALGO 510 handle missed calls; modes of operation; and calls to an empirical algorithm module (EA) 518 provided in the ALGO 510. The EA 518 is a collection of rule base intensive therapy strategies for recommending insulin dose which calls on and/or provides a number of the functional modules 56 (FIG. 3). The insulin dosage recommendation is based on the latest glucose information and event information, such as meals, exercise, intervention, and so on. Intensive therapy is a form of treatment for insulin-dependent diabetes in which the main objective is to keep blood glucose levels as close to the normal range as possible. The treatment consists of three or more insulin injections a day or use of an insulin pump; four or more blood glucose tests a day; adjustment of insulin, food intake, and activity levels based on blood glucose test results; dietary counseling; and management by a diabetes team. The EA 518 extends this principle by continuously monitoring glucose and implementing intensive therapy rules at frequent regular intervals. The insulin dose recommendation is evaluated using the latest glucose measurements, past insulin delivery information and event information, such as meals, exercise, interventions, and so on. In one embodiment, such updates to the EA 518 are conveniently made by providing an open architecture which permit replacing/updating an existing EA 518 with a revised empirical algorithm. One such suitable open architecture method which may be implemented within the present invention is described in U.S. application Ser. No. 12/121,199, entitled Therapy Delivery System Having An Open Architecture And A Method Thereof, now U.S. Pat. No. 8,123,717, which is assigned to the assignee of this disclosure, and the disclosure of which is incorporated herein by reference.

As used herein in defining portions of the EA 518 and other modules of the APTS 500 the symbols listed in Table 2 having the following nomenclature.

TABLE 2

Nomenclature

| Symbols | Description |
| --- | --- |
| Δ | Prefix indicating a difference, a change, or an increment. |
| k | Current control cycle |
| K | $K^{th}$ cycle is the measurement data set determined for current cycle k, and also used as a constant factor |
| $K_I$ | Insulin sensitivity |
| $K_\eta^E$ | Recovery phase basal correction factor |
| $K_P^{FC}$ | Gain for fast carbohydrate |
| $t_\eta^E$ | Time of exercise completion |
| $T_\eta^E$ | Duration of exercise recovery phase |
| $K_P^E$ | Expected gain factor for exercise |
| $\Delta G_P^E$ | Change in glucose push due to exercise |
| $\Delta G_P^{LG}$ | Expected glucose push due for low glucose intervention |
| $A^{HG}$ | Amount of insulin [U] for high glucose intervention |
| $A^{LG}$ | Amount of carbohydrates for low glucose intervention |
| $A^{FC}$ | Amount of fast carbohydrates |
| $A^{CB}$ | Amount of insulin [U] for commanded bolus |
| $A_r^M$ | Meal amount remaining |
| $A^M$ | Meal amount |
| $A_c^M$ | Meal correction amount |
| $A_0^M$ | Meal amount threshold defined as snack |

TABLE 2-continued

Nomenclature

| Symbols | Description |
|---|---|
| $g_i^K$ | The $i^{th}$ value in the $K^{th}$ glucose set: $(g_\theta^K, \ldots, g_i^K, \ldots, g_2^K, g_1^K)$ in the window of concern and corresponding measurement time: $(\tau_\theta^K, \ldots, \tau_i^K, \ldots \tau_2^K, \tau_1^K)$. Note the "window of concern" is the segment of time in focus for performing a search, such as a glucose measurement search. |
| θ | Number of glucose points within process glucose value |
| G[K] | The $K^{th}$ glucose value obtained from processing $K^{th}$ sensor data-set |
| $t_G$[K] | Glucose time stamp obtained from processing sensor data |
| $G_T$ | Glucose target |
| $G_T^{Hi}$ | Upper Glucose target |
| $G_T^{Lo}$ | Lower Glucose target |
| $G_1$ | Glucose reference point 1 |
| $\vec{I}$ | Insulin delivered vector |
| $\vec{I}_N$ | Nullified insulin vector |
| $\vec{I}_\eta$ | Meal related, and Hi-glucose intervention boluses |
| $\vec{I}_S$ | Insulin self bolus vector |
| $\vec{I}$ | Insulin remaining vector |
| $I^{Br}$ | Basal insulin |
| $G^B$ | Basal glucose |
| $\vec{I}_r$ | Insulin remain vector, $I_r[i] i^{th}$ term |
| A | Amount |
| n | Insulin duration in number of control cycles |
| $n_H$ | Number of history points |
| $T_D^I$ | Insulin activity duration |
| $\Delta G_P$ | Glucose push matrix with time and glucose columns |
| $\delta G_P$ | Temporary glucose push matrix with time and glucose columns |
| $T_C^M$ | Meal correction time window |
| $t_{MC}$ | Meal correction time |
| $t_M$ | Time of meal consumption |
| $\Delta G_P^{FC}$ | Glucose push increment for fast carbohydrate intake |
| $T_1^{BF}, T_2^{BF}$ | Breakfast |
| $T_1^{LU}, T_2^{LU}$ | Lunch |
| $T_1^{SU}, T_2^{SU}$ | Supper |
| T | Point called Target |
| 1 | Point called 1 |
| 2 | Point called 2 |
| P | Push (use push) |
| r | Remain |
| I | Insulin delivery |
| → | Arrow indicates vector |
| B | Basal |
| N | Nullified |
| LU | Lunch |
| BF | Breakfast |
| SN | Snack |
| SU | Supper |
| FC | Fast-acting carbohydrate |
| M | Meal |
| E | Exercise |
| LG | Low glucose intervention |
| HG | High glucose intervention |

Timing Aspects

As mentioned APTS is a real time system where timing is a key aspect in dosing. The EA 518 uses a digital compensator independent of real time that determines the appropriate control amount. The EA 518 is structured such that it has no real sense of time but uses the timing that exists in the indices of variable arrays. In other words, the actions of the EA 518 are in a sense index-based, and the notion of time is made implicit within by the selection of a control cycle period $T_C$. For example, the insulin pharmacodynamics is defined as a one-dimensional array of insulin remaining $I_r[i]$, where $i^{th}$ element indirectly indicates the insulin remaining at elapsed time $t=(i-1)T_C$. Thus, there exists a correspondence between the $i^{th}$ index and time t.

Figure 20:
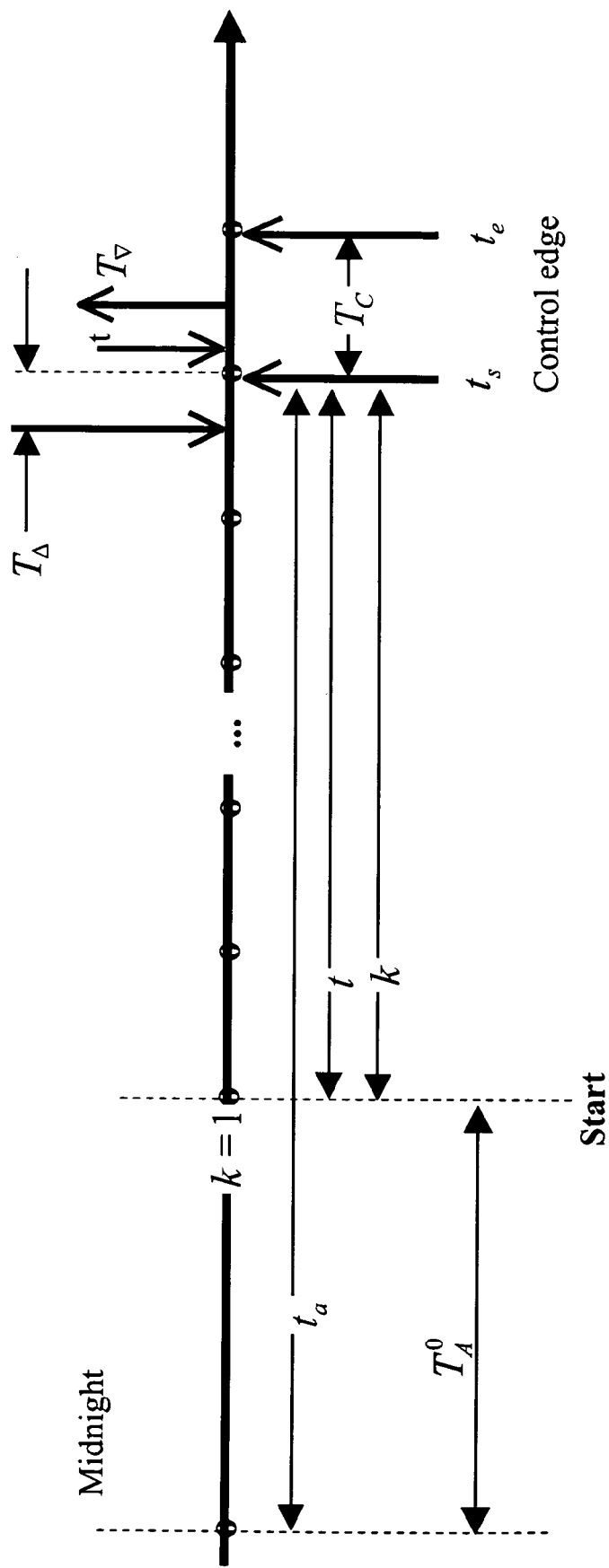
FIG. 20 is a graph showing timing descriptions used by an algorithm according to the present invention.

As shown by FIG. 20, the timing description of the ALGO 510 controller depends not only on time of day but also depends on time lapsed since start of an experiment (e.g., start of an implemented therapy recommendation as a prescription). The term $T_A^0$ represents the time at which the experiment is started and is stored by APS 502. The time is converted to minutes and represents the time in minutes since midnight. The term $t_a$ is the actual time of day in minutes since midnight. The term t is the elapsed time relative to start of the experiment, where relative time t=0 indicates the start of the experiment. The K=1 term refers to the first control cycle. Every subsequent cycle is incremented by 1. The term k denotes the current $k^{th}$ cycle. Each control cycle period $T_C$ has a pair of control edges, a start time $t_s$ and end time $t_e$. At any given relative time t, the ALGO 510 determines to which control cycle period $T_C$ the current call sits in for the current time T. Critical is that the real time control system implemented has soft time control. This means that a call to the ALGO 510 is not exactly at the starting edge of the control cycle period $T_C$, but rather within some time precision about the control edge of start time $t_s$. The term $T_A$ is a time offset from control edge and is the instant at which data request is sent and acquired by APS 502. For example, a value may represent a time at which the PU 508 transfers data collected from various devices to APS 502 via APSCOM 504. The term $T_\nabla$ is the time at which APS 502 transfers commanded insulin to the PU 508. The term $T_\delta$ is the time out-maximum duration for which the window for recommendation and confirmation window is displayed with respect to the edge of start time $t_s$ of control cycle period $T_C$.

Memory Duration

The EA 518 uses past information and current information to compute the insulin recommendation for the ALGO 510. The period of time over which the information is needed depends on how long the system takes to clear the effect of an input. If the insulin activity duration is $T_D^I$ minutes then as given by equation (4):

$$n = \text{ceil}\left(\frac{T_D^I}{T_c}\right), \quad (4)$$

where n is the number of cycles over which the information is maintained. To cover the case of missed cycles, several extra control cycles are also needed as a buffer. In this case, $n_H$ is defined as the sum of n and the maximum number of expected missed cycles. The necessary (and sufficient) range to manage the ALGO 510 is to maintain the history over $n_H$ cycles.

Missed Cycles

The ALGO 510 is responsible for processing all new information inputs and for translating the information into a therapy. A missed cycle is a control cycle period in which the ALGO 510 is not called. If the whole APTS 500 was perfect, the ALGO 510 would be called every control cycle period $T_C$. However, calls can be missed. If cycles are missed, then the ALGO 510 is iteratively executed for each of the missed cycles. This means that when missed cycles happen, therapy is pending until ALGO 510 is called. The ALGO 510 detects the missed calls and steps through each of the missed cycles before executing the current call. This ensures that the events are neither missed nor duplicated and are sequentially addressed. Missed cycles can occur for various reasons. The synchronization is accurate as long as the information passed to the ALGO 510 has no discrepancies. In handling this scenario, the ALGO 510 first determines if a call was missed. If no missed call is found, the ALGO 510 then executes the various EA 518 modules. When the ALGO 510 detects missed calls, the ALGO 510 first executes all of the missed calls before evaluating the current call.

Modes of Operation

Figure 6:
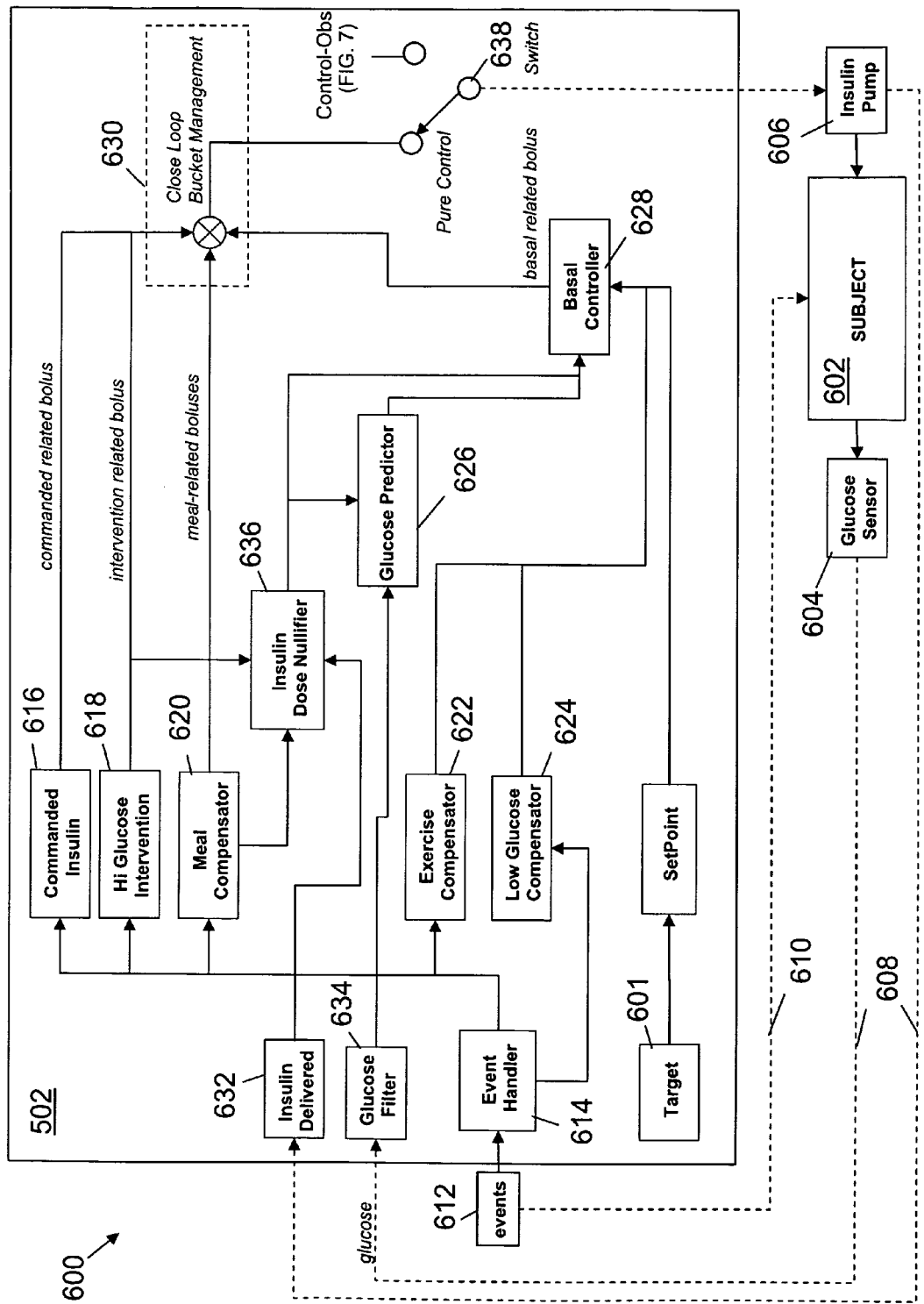
FIG. 6 is a block diagram of a software components, devices, and interactions used in the system of FIG. 2 and to enable the software of FIG. 5 as a closed-loop system that uses glucose measurements to provide an appropriate control action based on a patient-specific therapy according to an embodiment of the present invention.

The modes of operation supported by ALGO 510 are Pure-control and Controlled-Obs. Referring to FIG. 6, the Pure-control mode 600 of operation for the EA 518 is a closed-loop system that uses glucose measurements to provide an appropriate control action. The task of the ALGO 510 is to maintain glucose at a predetermined target glucose level 601. During controller initialization or whenever the subject is disturbed, the glucose is expected to deviate from the target glucose level 601. Pure-control uses glucose measurements and delivered insulin information to "understand" the state of the subject. At the bottom right of FIG. 6, a subject block 602 is connected to a glucose sensor 604 and an insulin pump 606. These devices are indirectly in contact with APS 502 via RF link 608 of the portable unit 502 (FIG. 5) which is shown in dashed lines. A dashed line 610 originating from events block 612 indicates the occurrence of the known events. Information of these events is made available to the ALGO 510. An event handler 614 provides appropriate mapping between external event descriptions to an internal event schema. ALGO 510 triggers the appropriate modules to handle the known disturbances, which includes at least one of a command insulin module 616, high glucose intervention module 618, a meal compensator module 620, an exercise compensator 622, or a low glucose compensator module 624. A glucose predictor 626 and a basal controller 628 handle unknown disturbances and modeling errors. Initialization of the controller is a case of unknown disturbance. The controller has to stabilize initial glucose values when the experiment begins, and when the mode switches from Controlled-Obs mode 700 to pure-control mode 600. In such cases, the Pure-control mode 600 performance relies on the availability of information from past events to bring the subject smoothly from some initial glucose value to target glucose value. A closed-loop bucket management block 630 determines and manages the net insulin recommendation. The modules insulin delivered 632, glucose filter 634, and insulin dose nullifier 636 are discussed in later sections provided below.

Pure control mode 600 is an insulin recommendation that uses glucose measurements and internal/external input events to maintain glycemic control. The healthcare professional actively closes the loop by accepting an insulin recommendation, which changes a switch 638 to this mode. The modes of operation make the distinction between an open-loop HCP-managed insulin recommendation and a semi closed-loop ALGO-determined insulin recommendation. Even though these two modes are set by the healthcare professional, there are situations in which the ALGO 510 puts itself in Controlled-Obs mode 700. This happens when the following conditions are met: no bG condition which occurs on non-availability of glucose measurement due to measurement delays (e.g., at the start of the experiment, if it occurs at all); and outdated bG measurement which indicated that time since last available glucose measurement is older than admissible glucose expiry age. The Controlled-Obs mode 700 is now discussed hereafter with reference made to FIG. 7.

Figure 7:
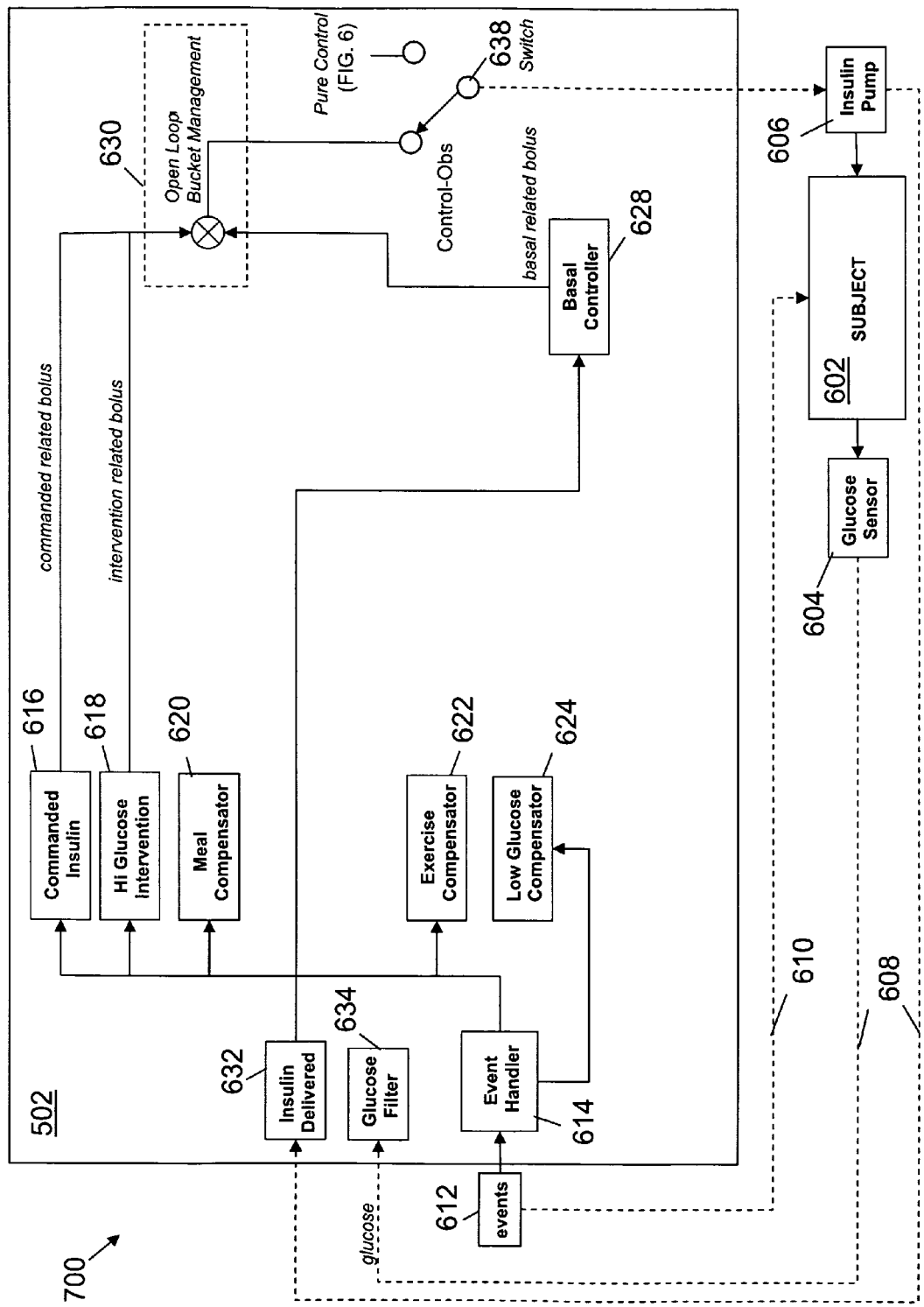
FIG. 7 is a block diagram of a software components, devices, and interactions used in the system of FIG. 2 and to enable the software of FIG. 5 as a open-loop system to provide an appropriate control action based on a patient-specific therapy according to an embodiment of the present invention.

Controlled-obs mode 700 is a special case of Pure-control mode 600 and is shown by block diagram in FIG. 7. The user therapy is implemented through the use of the subject's pre-programmed pump basal rate and augmented by the use of a commanded bolus event. This is open-loop control, and the therapy is manually managed by the healthcare professional or the subject. As the description is similar to that provided for the Pure-control mode 600, like elements are indicated with like symbols. Working wise, glucose measurements, insulin delivery and the events recorded are primarily used by the ALGO 510 to maintain history and update state vector. However, only two event modules are applicable, the commanded bolus module 616 and the high glucose intervention module 618. These modules enable the subject or the healthcare professional to manage the therapy and administer insulin boli. The meal compensator event 620, exercise compensator event 622, and the low glucose intervention event 624 are not executed in the Controlled-Obs mode 700. The basal rate control 628 is a replication of the programmed pump profile.

Empirical Algorithm Call

Figure 8:
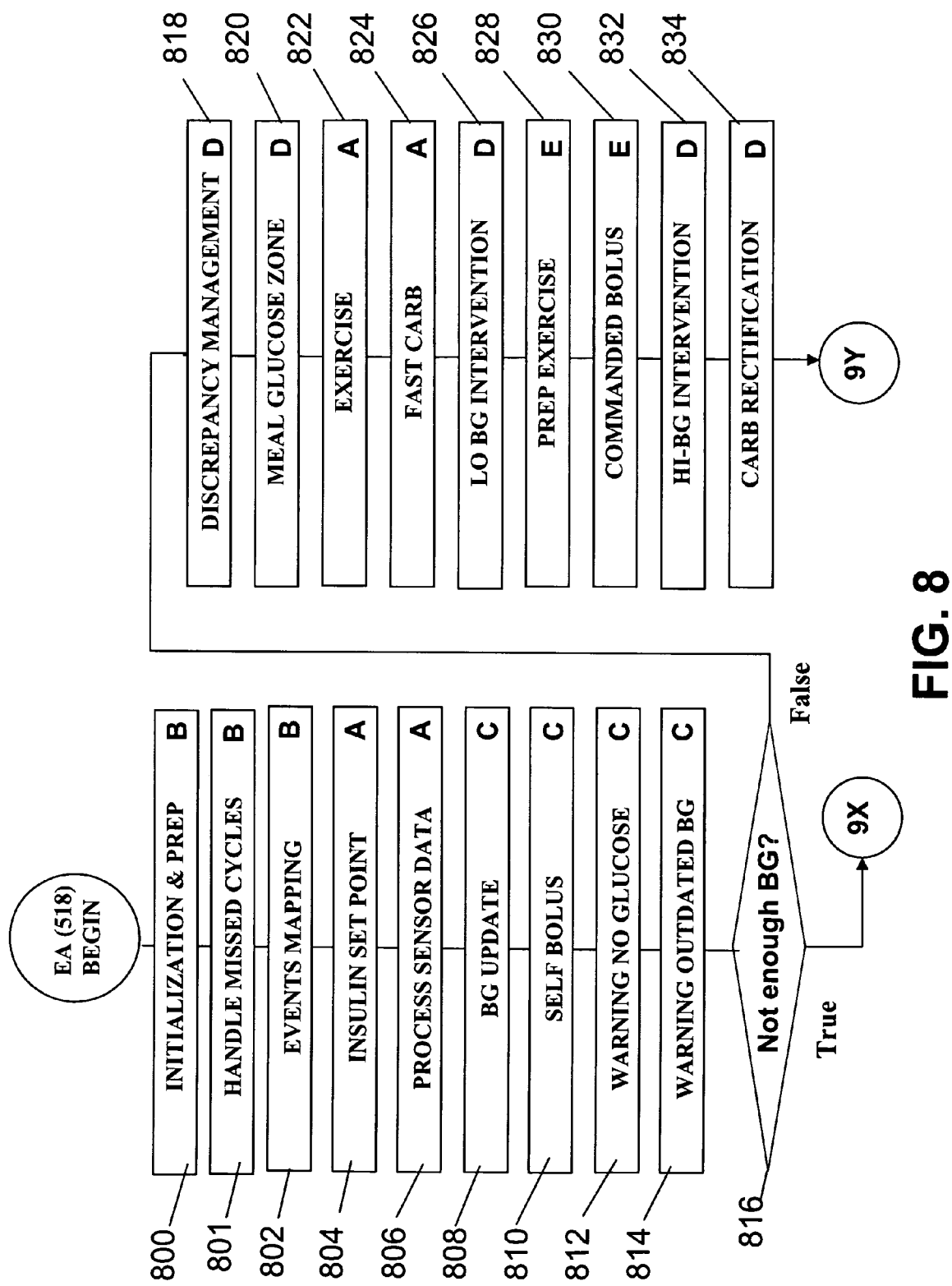
FIGS. 8 and 9 are process flow diagrams showing a sequence of module executions according to an empirical algorithm embodiment of the present invention.
Figure 9:
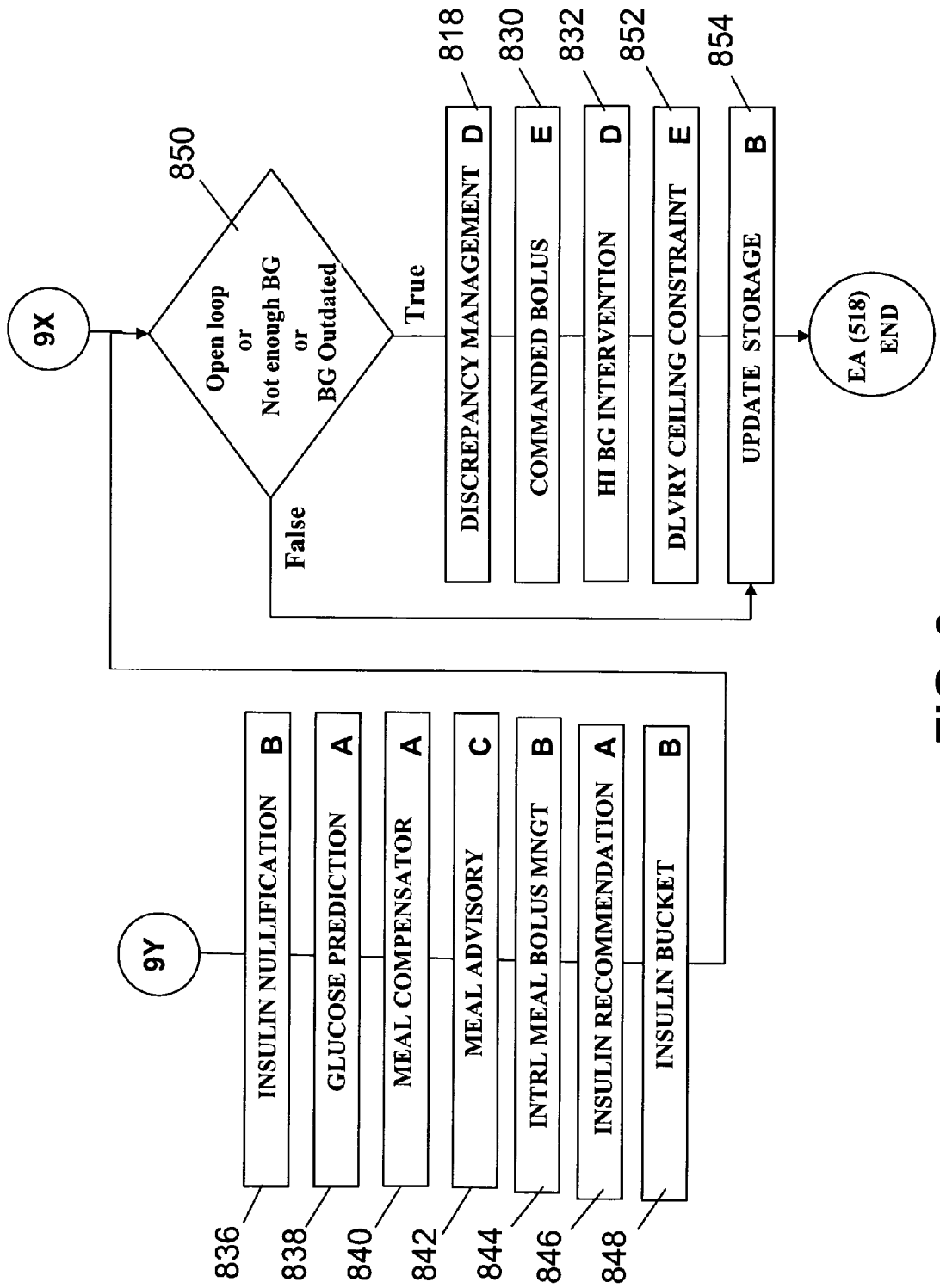

The Empirical Algorithm (EA) 518 is structured as a group of modules. Each module handles an aspect of a therapy recommendation. FIGS. 8 and 9 is a flowchart of the EA 518 showing all the modules and an order of execution according to an embodiment of the present invention. The is presented only for illustration purposes and can be ordered in a number of ways in order embodiments. Points 9X and 9Y shown in circles in FIGS. 8 and 9 are the links between the figures. Each module is structured as an independent behavior that contributes to the final therapy recommendation. So each module can be seen as a superposition of effects. The letters A-E coding each of the modules represent a model group and along with their respective legend provide structuring information. The module groups and their associated letter are: "A"—Core Control Actions (central to providing glycemic control), "B"—Management and Housekeeping (top level); "C"—Monitoring and Status Information; D—"Corrective Actions", and "E"—Handling Major Events. A general discussion on each of these modules group is provided hereafter.

Core Control Actions

The modules for core control actions, central to providing glycemic control are: process sensor data 806, insulin set point 804, glucose prediction 838, insulin recommendation module 846, exercise compensator 822, fast-acting carbohydrate ingestion 824, meal compensator 840, and open loop basal implementation logic 850. The process sensor data 806 contains the strategy to determine a glucose value from available measured glucose values. Insulin set point 804 is the insulin infusion rate used to maintain target basal glucose. The glucose prediction 838 predicts the glucose value for control cycles from the last known glucose measurement values. The insulin recommendation module 846 computes the insulin dose to maintain basal glucose. The exercise compensator 822 handles an increased physical activity level. The fast-acting carbohydrate ingestion 824 handles the ingestion of fast-acting carbohydrates to compensate for an expected glucose drop. The meal compensator 840 computes insulin boli distribution for a meal event. The open loop basal implementation 850 implements basal insulin during the open loop controller control-obs 700 (FIG. 7).

Management and Housekeeping (Top Level)

At the top level of ALGO 510 workings is the management and housekeeping related issues. The management and housekeeping modules are: initialization/preparation 800, handling missed cycle 801, event mapping 802, insulin buckets 848, and insulin nullification 836. The initialization/preparation module 800 is the ALGO state vector that manages the past, current and future information (ALGO memory). The handling missed cycle module 801 which has been discussed above in a previous section handles the restart of APTS or ALGO calls that were skipped for any reason. Event mapping 802 maps the external event set to the internal event set. Insulin buckets 848 manage the insulin recommendation from various modules as components to fill and empty buckets. Insulin nullification 836 negates any insulin components coming from feed-forward terms of the control action from final insulin delivery. Internal bolus management 844 delivers the feed forward boluses that result from a meal event.

Monitoring and Status Information

The modules for monitoring and informing status are: Glucose update 808 which tracks the availability of new glucose measurement values. Outdated glucose 814 informs the user if there is a need for a fresh glucose value. Self-bolus 810 accounts for any insulin discrepancy by means of self-bolus commands. Warning no glucose is a fail safe which advises the system that the PU 502 (FIG. 5) is not responding and that a watch dog circuit should begin the timer count down, such as described above in a previous section. Meal advisory 842 informs the user to start eating.

Corrective Actions

The modules for corrective actions are: carbohydrate rectification 834, hi-glucose intervention 832, lo-glucose intervention 826, meal glucose zone 820, and managing discrepancy 818. Carbohydrate rectification 834 reworks the previously entered meal event (carbohydrate value), and the insulin delivery is corrected accordingly. Hi-glucose intervention 832 corrects the high glucose level by means of insulin delivery. Lo-glucose intervention 826 corrects the low glucose level by means of ingesting fast-acting carbohydrates. Meal glucose zone 820 defines the glucose target as a band, rather than a line. Managing discrepancy 818 manages the insulin buckets when the discrepancy between the commanded insulin versus the delivered insulin is identified.

Major Event Handlers

The modules for handling major events are: Prep-Exercise 828, and Commanded bolus 830. Prep-Exercise 828 reworks the basal requirement in anticipation of the exercise controller, and informs the controller at the onset of specific exercise. Commanded bolus 830 request for additional insulin bolus. Although the above module descriptions of the EA 518 were general in nature for certain modules, a more detailed discussion on such modules is provided hereafter.

Event Mapping

After running the initializing and preparing and handling missed cycle modules 800 and 801, the ALGO 510 then runs the event mapping module 802 to acquire external disturbance information through events received by APS 502. For example, in one embodiment external events are displayed in a drop-down list in the user interface 512 of the APTS 500 for user selection. The ALGO 510 operates on events that are specific to the ALGO itself. These are called internal events. Each external event selected by the user is mapped to at most one internal event. The external events are provided with descriptors for the end-user to relate to, and/or they trigger an ALGO action when selected. These descriptors could be user-specific, and could support multiple languages.

In one embodiment, there could be multiple external event descriptors relating to the same internal event. For example, "self-bolus" and "priming bolus" are separate external event descriptors, but internally both of these events point to the same internal event type (called Self-Bolus). Thus, it is possible to have multiple external events pointing to the same internal event (many-to-one). Table 3 lists the fundamental internal events from which the ALGO 510 works.

TABLE 3

Fundamental internal event list for EA

| Internal Event | Description |
| --- | --- |
| Snack | Carbohydrate ingestion |
| Breakfast | Carbohydrate ingestion |
| Lunch | Carbohydrate ingestion |
| Supper | Carbohydrate ingestion |
| Fast_Carbs | Rapid acting carbohydrate, normally triggered during exercise |
| Self_Bolus | The pump is manually commanded to deliver insulin not seen by ALGO 510 |
| Prep_Exercise | Reduces insulin to allow expected glucose drop at onset of exercise |
| Exercise | Actual start of an exercise activity |

TABLE 3-continued

Fundamental internal event list for EA

| Internal Event | Description |
| --- | --- |
| HI_BG_Intervention | Correction made for hyperglycemia with the feedback part being blind to additional commanded insulin part HCP entered to correct hyperglycemia |
| LO_BG_Intervention | Correction made for hypoglycemia by sculpting the glucose target |
| Infusion_Rate | Defines the basal rate at the start of the experiment |
| Prime_Pump | The pump is manually commanded to deliver insulin for priming purposes |
| Commanded_Bolus | The pump is commanded to deliver insulin |
| CarbRectification | Makes a correction to the last meal entry |

Insulin Set Point

Next the EA 518 runs the insulin set point module 804. For this module 804, basal insulin rate (i.e., the insulin infusion rate used to maintain a glucose value) is the basal profile that is normally defined for a typical day. However, a typical day as seen by the subject's life-style and that is used to drive the ALGO 510 are quite different. For example, and as used herein, there are two kinds of basal insulin profiles: (a) pump-profile and (b) ALGO defined profile. For the pump profile, the basal rate varies over the day. The pre-programmed rates may include insulin to cover parts of meal and other typical events. The defined profile is user-specific and customized to subject's daily schedule and life-style. For the ALGO defined profile, the profile is determined after analyzing and removing boli needed to manage events like meals and exercise. To determine the ALGO defined profile, the EA 518 uses intensive data monitoring for a new subject. For subjects that have gone through an experiment, this clinical data is used to determine the ALGO defined profile. These are determined through experimental protocols and supporting tools, such as ravel and unravel tools. The extracted basal rate thus determined is independent of events related insulin doses. This ALGO defined profile is saved as the basal set.

The basal set is shown as a three-column array matrix, which is defined by a subject initialization file (i.e., Subject-ini file). It contains time, basal rate, and basal glucose. Table 4 is an example of a basal set in the subject's initialization file.

TABLE 4

Basal set example

| Time since midnight [minutes] $t_a$ | Basal Rate [U/h] $I_1^B$ | Glucose [mg/dL] $G_1^B$ |
| --- | --- | --- |
| 0 | 0.6 | 110 |
| 480 | 1.3 | 110 |
| 960 | 1.0 | 110 |
| 1290 | 0.6 | 110 |

Figure 10:
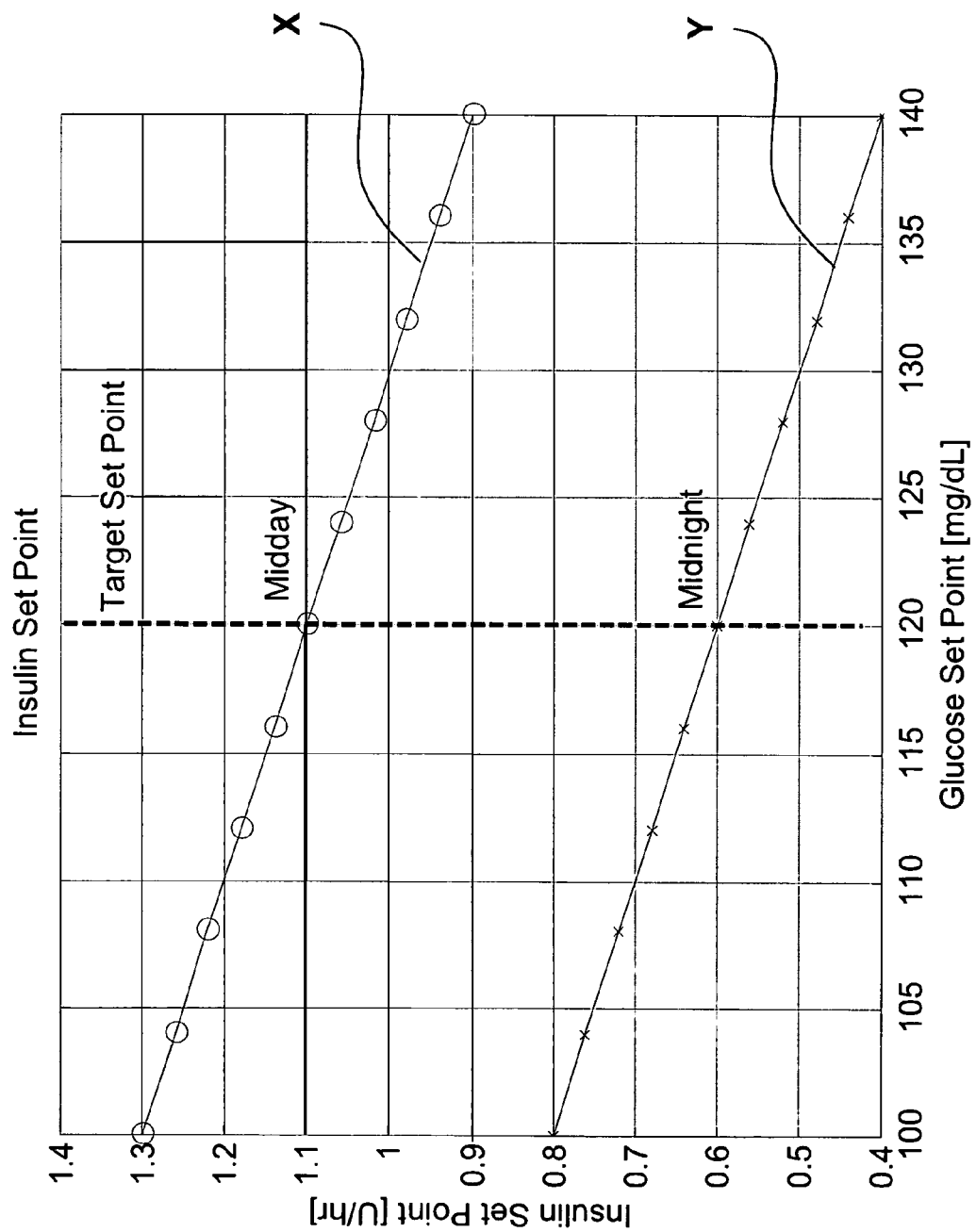
FIG. 10 is a graph showing a set point relationship between insulin and glucose at different times of the day.

The basal rate is a function of both the target glucose value and the time of day. The daily basal rate profile is defined as a fixed flow rate of insulin in U/hr for a time $t_a$. The time $t_a$ is defined in minutes from midnight, and the insulin profile is arranged in ascending order according to time. A fixed flow rate is implemented until the next set of insulin flow rate is reached. The basal rate profile is repeats itself over each 24 hour time period. The basal insulin rate is integral to the maintenance of the target glucose. The insulin rate given and the corresponding glucose value determine the insulin rate needed to maintain a given target glucose value. It is assumed that the insulin rate is a linear function of target glucose, and is given as according to equation (5):

$$I^B = I_1^B + (G^B - G_1^B)\frac{\Delta I}{\Delta G}, \quad (5)$$

where $G^B$ is a target glucose value, $I^B$ is an insulin rate to maintain a glucose value of $G^B$, $G_1^B$ is a glucose value defined in the basal set for given time of day, $I_1^B$ is an insulin rate needed to maintain a glucose value of $G_I B$, and $$\frac{\Delta I}{\Delta G}$$

is an insulin rate per glucose change. For example, FIG. 10 graphically shows the above set point relationship. In particular, line X in FIG. 10 shows the basal insulin rate at midday as a function of the glucose set point when $$\frac{\Delta I}{\Delta G} = \frac{0.1 \text{ U/hr}}{10 \text{ mg/dL}}$$

is defined as a constant. Line Y similar shows the same for the basal insulin rate at midnight but at a lower set point (0.8 versus 1.3). Please note, however, the slope is exaggerated to show this insulin-glucose relationship and is only an illustrative example.

Process Sensor Data

After running through the insulin set point module 804, the EA 518 now proceeds to call the process sensor data module 806. Data is collected from a sensor such as, for example, glucose sensor 604 (FIG. 7) by the process data module 806 and classified as raw data. Along with the sensor status, the raw data is processed and analyzed to determine a glucose value and measurement time. For example, the processes should remove outliers from past and current data sets, and other information such as sensor status and secondary sensors to determine the most reliable and accurate glucose value. One of two processing functions is use depending on the type of sensor that has provided the raw data.

Figure 11:
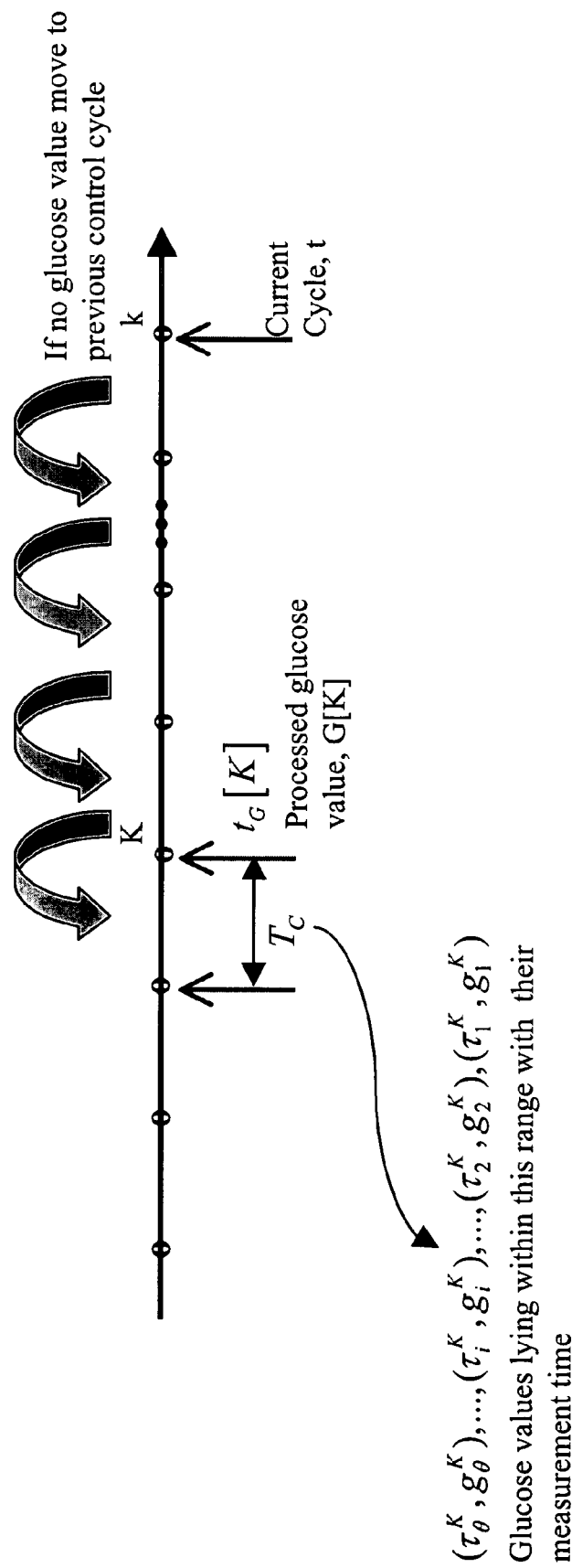
FIGS. 11 and 12 are depictions showing graphically a selection of a time interval for first and second processing functions, respectively, according to the present invention.

The first processing function finds and uses the most recently entered glucose data point. The function searches for any glucose data available for a control cycle by going backwards through each control cycle until it successfully locates the set of glucose value(s) or runs out of glucose data. If the glucose data set is empty, then an empty glucose vector is returned. Upon determining a non-empty glucose set, A time window of length $T_C$ is defined as $(t_G - T_C, t_G]$. The mean of the glucose value(s), $$G[K] = \frac{\sum_{i=1}^{\theta} g_i^K}{\theta}$$

is reported. Glucose value at $K^{th}$ index for $k^{th}$ cycle. The glucose time stamp $t_G[K]$ assigned is end time for the selected control cycle. FIG. 11 shows graphically the selection of the time interval for the first processing function using the above variables.

The second processing function is used when the operational characteristics of the current glucose sensor provide a data range such as, for example, by a subcutaneous continuous glucose monitor. In this example, the data range has a lower limit of 20 mg/dL, and an upper limit of 450 mg/dL. In this example, other possible, glucose rate limits are not specified. In one embodiment, the sensor records invalid glucose data out side the range by assigning the data a value of zero. As such these invalid glucose values ($g_i^K=0$) are then stripped out of the raw data by the process sensor data module 806 and will not to be included in any quantitative analysis. In one embodiment, a pop-up message is displayed to warn the user of the upper and lower limits.

Figure 12:
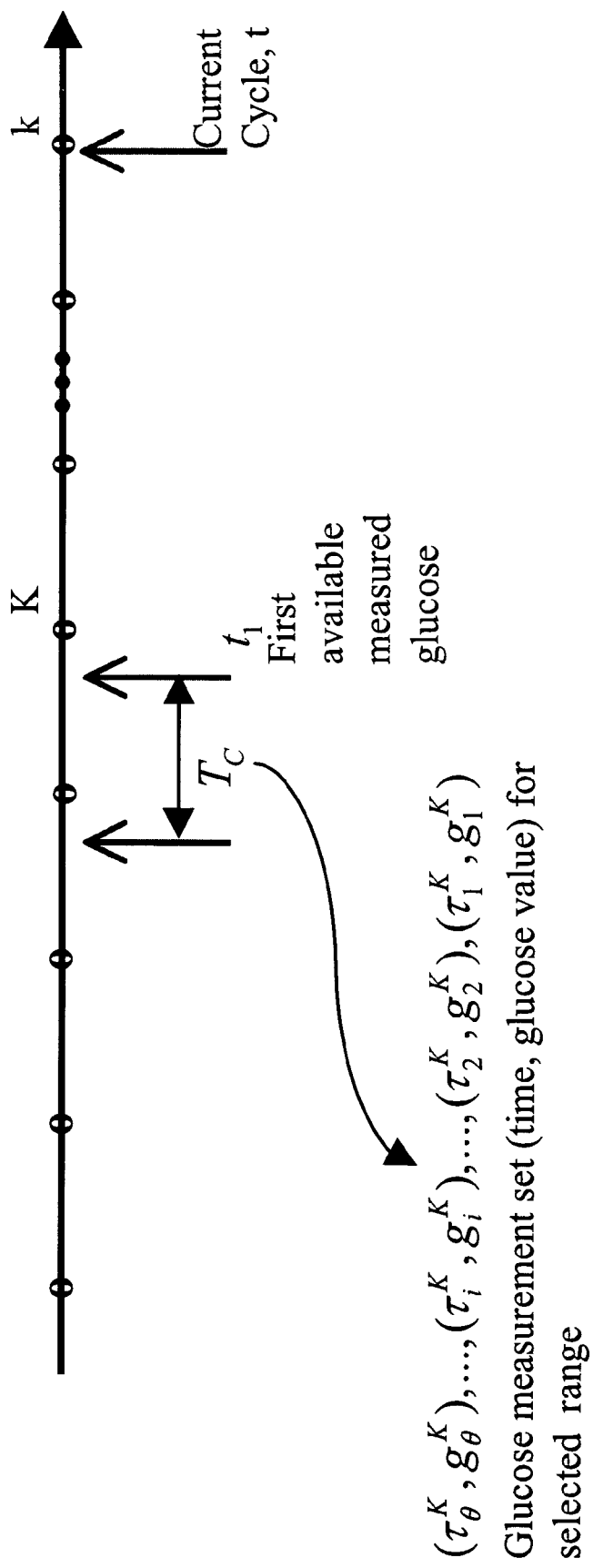

When computing a glucose value for the EA, Only the primary sensor data is considered. The latest available glucose value(s) is selected. A time window of length $T_C$ is defined as: $(t_1-T_C, t_1]$. The available glucose values over the selected window are chosen, and the median is selected: $G[K]=\text{median}(g_\theta^K, \ldots, g_i^K, \ldots, g_2^K, g_1^K)$. Glucose value at $K^{th}$ index for $k^{th}$ cycle. The median for time is computed and returned as $t_G[K]=\text{median}(\tau_\theta^K, \ldots, \tau_i^K, \ldots \tau_2^K, \tau_1^K)$. Note, the median time $t_G[K]$ shall be rounded to the nearest control cycle edge by the EA 518 where needed. FIG. 12 shows the selection of the time interval for the second processing function.

Glucose Update

After collecting and processing the raw data, the EA 518 then proceeds to call the glucose update module 808. Glucose update explains an aspect of glucose availability and its implication to the internal workings of the ALGO 510. It is not directly relevant to end-users outside of the ALGO 510. Getting the latest glucose value is crucial for maintaining glycemic control. Due to sensor delay and/or sensor failure, a glucose predictor is needed to get an estimate of the current glucose. When the sensor provides new glucose values, the insulin recommendation module 846 reworks the glucose prediction using the latest measured glucose. However, in the absence of new glucose information, the predicted glucose determined during the control cycle is instead used to predict glucose for the current cycle. In this case, the state information is efficiently used to step forward from last control cycle to the current new cycle for predicting glucose. The glucose update module 808 thus identifies whether or not a new set of glucose measurements are available, and whether to use last predicted glucose and continue.

Self-Bolus

The EA 518 then calls on the self-bolus module 810 to account for any insulin discrepancy by accessing information from the pump regarding self-bolus commands. There are several reasons why physical access to the insulin pump is needed such as, for example, battery change, changes in insulin tubing, or the user wants to manually command a bolus. One aspect of this is that any manually commanded bolus is seen at the start of each control cycle in the net insulin delivered term. Since the ALGO 510 did not recommend the manually commanded bolus, the EA 518 will consider this bolus as a dose overage. The determined overage of insulin is then accounted for and adjusted by feedback during future control actions. To systematically handle this case a self-bolus event must be triggered prior to the manual bolus action. The ALGO 510 is then expecting an overage amount equal to the entered self-bolus amount. Using this event also ensures that all manual boli are properly accounted for. Unresolved bolus is the remainder from the commanded bolus.

The unresolved bolus has a finite time window within which the self-bolus amount should get resolved. The amount is resolved with a dose overage; otherwise the unresolved bolus (i.e., the balance of the self-bolus amount) is set to zero. Another reason for limiting the event to a finite duration is to clear the memory as a safety precaution in case the user informs the test stand of overage but does not command a bolus from the pump. A no glucose warning message is displayed by a no-glucose advisory module 812 to the user before setting the unresolved self-bolus amount to zero.

Outdated Glucose Measurement

After collecting and processing the raw data and sending a warning if appropriate, the EA 518 then proceeds to call the outdated glucose module 814. The accuracy and reliability of a glucose predictor deteriorates as the length of prediction increases. If the last glucose value received is older than a certain specified time window, the ALGO 510 enforces the open loop Controlled-Obs mode 700 (FIG. 7) as a safety precaution and implements a preprogrammed basal control. By working in Controlled-Obs mode 700, the therapy is constrained to that programmed into the basal profile of the insulin pump, and if needed it will be augmented by a subset of the functionalities exposed. The task of the outdated glucose module 814 is to give information regarding the pending outdated glucose state by means of pop-up messages. When an outdated glucose state is reached, the outdated glucose module 814 switches the appropriate flags to enforce Controlled-Obs mode 700. Providing a new primary glucose measurement will rectify the situation. Accordingly, the outdated glucose indicates that the glucose prediction is no longer valid, and forces the controller into Controlled-Obs mode 700.

The following warnings are provided by the outdated glucose module 814: pre-warning the operator, warning the operator, and glucose measurement outdated. For pre-warning the operator, the user is pre-warned of the pending expiration by means of the log window. In count down warn cycles prior to expiration, the user is iteratively informed that n number of minutes is left before an expiration term. In addition, the following message appears: "WARNING: Glucose will be outdated soon. Please enter current glucose." For warning the operator, a pop-up message is forced on the last expiration term cycle and on every cycle thereafter until a new glucose measurement is received. This message appears: "WARNING: Glucose will be outdated next cycle. Please enter current glucose." For glucose measurement outdated, during an outdated glucose condition, the ALGO 510 shall force itself into the open loop Controlled-Obs mode 700 if the ALGO 510 is in the closed loop Pure-control mode 600, and implement the user's basal insulin profile. Also, this message appears: "WARNING: Glucose Outdated. Running Control Obs! Please enter current glucose." Next the EA 518 checks to see if there are enough bG measurements in the collected and processed data to continue at process flow point 816. If not, the EA proceed to process flow point 850 which is discuss in a later section. If so, then the EA 518 continues to the discrepancy management module 818.

Managing the Discrepancy Between Expected Results and Actual Results

The discrepancy management module 818 checks to see if the commanded insulin determined by EA 518 is different from the insulin dispensed from the pump. If so, then the EA 518 flags this as a commanded insulin discrepancy and presents notification to the user on the user interface 512 (FIG. 5). The discrepancy between commanded and delivered insulin needs then to be resolved by the user and/or healthcare professional as the cause of the discrepancy is likely independent of the APTS 500 (e.g., defeated insulin pump).

Meal Glucose Zone

Figure 13:
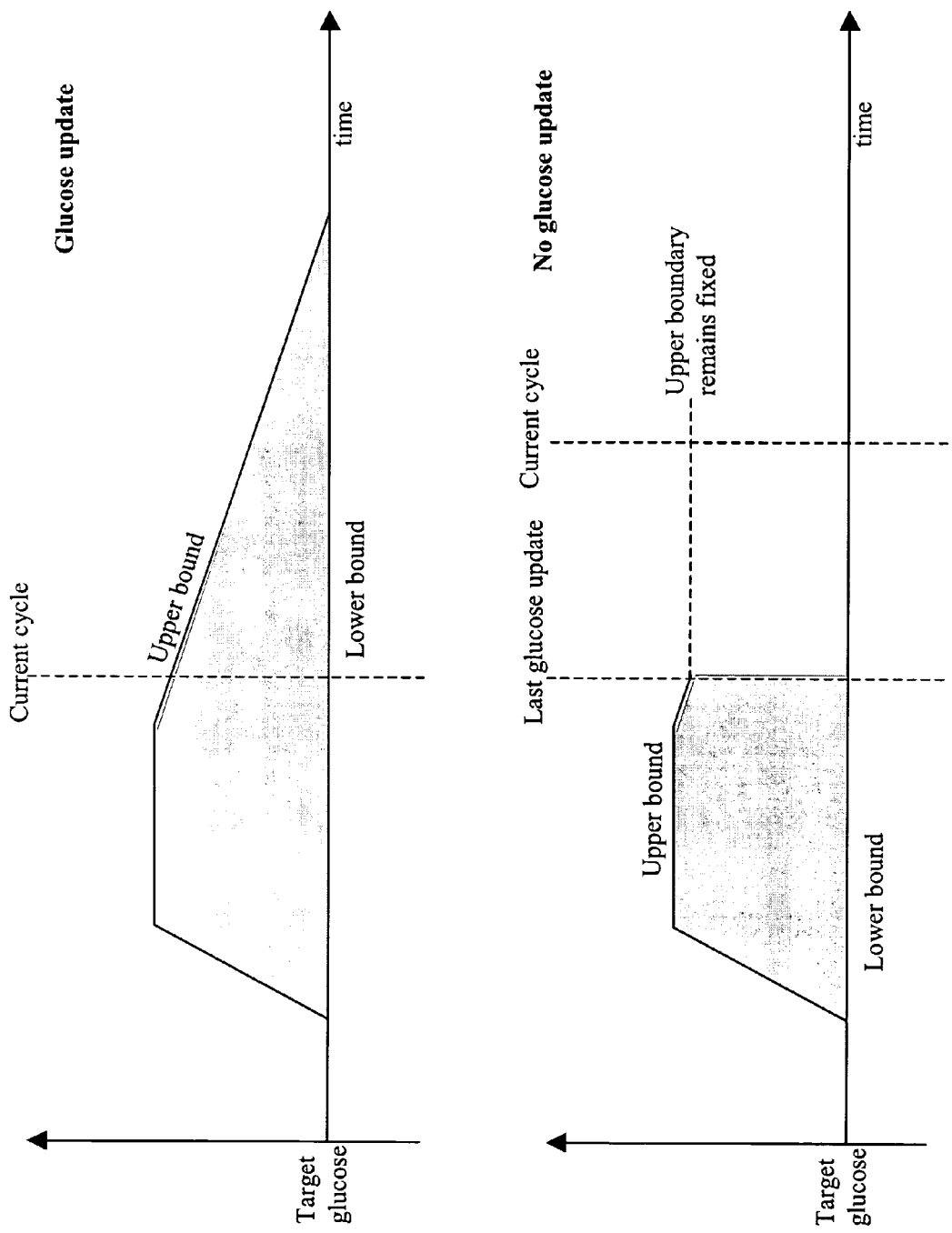
FIG. 13 is a pair of graphs showing different glucose zone scenarios.

The EA 518 then proceeds to the meal glucose zone module 820. At this point, the meal glucose zone module 820 simply sets the glucose target as a band, rather than a line. This band is used by ALGO 510 in the closed loop Pure-control mode 600 as the target 601, which also provides a setpoint 603 that is used by the basal controller 628 (FIG. 6). It is to be appreciated that the glucose predictor 626 used by the basal controller 628 as an action input does not account for glucose changes due to a meal. A meal instead is covered by pre-determined insulin dose distribution. This insulin dose distribution is determined so as to best minimize the glucose rise, and to bring the glucose to the target glucose level as quickly as possible with minimal undershoot. The glucose rise to meal intake cannot be removed completely. This is expected since there is about 30-60 minutes delay in peak insulin action. The insulin dosage obtained is optimized to minimize glucose rise due to the meal. The band of the meal-related target glucose zone is thus defined around the meal event as a region bounded by upper and lower target glucose boundaries. With respect to the defined target zone, FIG. 13 shows four different scenarios: (a) within glucose zone; (b) above the glucose zone; (c) below the glucose zone; and (d) no new glucose value.

(a) Within Glucose Zone

If the predicted glucose value lies within the glucose zone boundaries then the subject's glucose is considered within acceptable limits. The basal controller 628 in this case needs only the basal insulin to maintain glycemic control.

(b) Above the Glucose Zone

If the predicted glucose lies above the upper glucose boundary then the subject is considered as under-delivered in insulin. The basal controller 628 computes the deviation in glucose with respect to the upper glucose boundary. The action of the basal controller 628 accounts for this deviation and will curb for this unaccounted rise.

(c) Below the Glucose Zone

If the predicted glucose lies below the lower glucose boundary then the subject is considered as over-delivered in insulin. The basal controller 628 computes the deviation in glucose with respect to the lower glucose boundary. The action of the basal controller 628 accounts for this deviation and will curb for this unaccounted fall.

(d) No Glucose Update

The target zone covers the rise and fall of anticipated meal related response. A special case arises when glucose is not updated. With no update on glucose measurement the predicted glucose for the current control cycle $T_c$ is a glucose value without accounting for meal related rise or fall in glucose. The target-zone boundaries however are a function of time. This in general means that the predicted glucose is lower when meal is kicking in and higher when meal is dying out. This effect is accentuated with rising and falling meal zone boundaries. The EA 518 handles this case by holding the boundary limits last used with the last received glucose measurement. These upper and lower target values are held fixed for all future control cycles, until a new measurement comes through. This alleviates the problem to some extent.

Prep-Exercise and Exercise

Next the EA 518 evaluates whether the patient is involved in exercise via the exercise module 822. With an increased level of physical activity, the requirement for sustaining energy also increases. Glucose, which is the source of energy, is used at a higher rate to support increased activity. As such three assumptions of physiological behavior are made as follows. The first assumption is that upon the commencement of exercise, there is a drop in glucose levels. The second assumption is that the glucose drop is rapid, starting and ending approximately 10-minutes after the start and end of physical exercise. The final assumption is that once the physical activity level falls back to normal, there is an expected recovery phase as glucose is stored as glycogen in the muscles and liver. Accordingly, exercise is handled in stages by the exercise and pre-exercise modules 822 and 828, receptively.

The prep-exercise module 828, which the EA 518 calls later in the process flow, elevates glucose in anticipation of exercise by increasing the glucose set point so that the glucose level can safely drop during the exercise. As such, a normal therapy predetermined to handle exercise is to reduce the basal insulin in anticipation of exercise. The effect of lowering insulin on glucose depends on the pharmacodynamics of the insulin. The lower basal insulin level is then maintained for the duration of the exercise. In addition, if glucose levels are not elevated enough at the start of the exercise, the subject could manage their glucose level by consuming fast-acting carbohydrates. This causes the glucose level to rise rapidly.

The subject prepares for exercise by triggering a prep-exercise event by selecting an activity and/or activity level from a list provided on the user interface 512 (FIG. 5). The selected activity and/or activity level has a corresponding anticipated glucose drop. Until the exercise event is triggered, the change in target glucose is given by equation (6):

$$\Delta G_T = -\Delta G_P^E \qquad (6),$$

where $\Delta G_T$ is the change in the target glucose value, and $\Delta G_P^E$ is the anticipated push (rise) in glucose concentration which for exercise, the value is negative since exercise causes a drop in glucose. So the target glucose (i.e. target 601) is given by equation (7):

$$G_T = G_T + \Delta G_T \qquad (7).$$

Again, once the exercise activity commences, the body may need less insulin and may maintain a lower basal insulin requirement for the duration of the exercise. Upon the completion of exercise, the reduced basal is brought back to the normal basal setting in some predefined gradual manner.

After exercise has commenced, the exercise period module 822 projects a glucose drop for the duration of exercise. When the exercise event is triggered, the prep-exercise is turned OFF. The basal state is re-evaluated at the beginning of the exercise event. If the prep-exercise did not elevate the glucose level to the desired amount, then the subject is prompted by the ALGO 510 on the user interface 512 (FIG. 5) to consume fast-acting carbohydrates to supplement the rise. The glucose push vector gains a component due to the consumption of fast-acting carbohydrates (as is explained hereafter in the section entitled "Fast-Acting Carbohydrate"). The expected glucose drop caused by physical activity is expressed according to equation (8) as:

$$\Delta \vec{G}_P = \Delta \vec{G}_P + K_P^E \Delta \vec{G}^E \qquad (8),$$

where $\Delta \vec{G}_P$ is then used to compute the basal insulin needed (i.e., glucose push). Note that $K_P^E$ is a negative value for exercise. The effects of the exercise and the fast-acting carbohydrates are modeled as glucose push vectors moving in opposite directions in a normalized glucose-rise response curve.

After exercising, the exercise module 822 provides an exercise recovery period which gradually normalizes the basal rate as per the basal set requirement. In this implementation, the duration of exercise is pre-defined in the vector $\Delta \vec{G}^E$.

Once the exercise is over, the glucose push due to exercise $\Delta \vec{G}^E$ becomes 0. The discontinuity is smoothened by using $K_\eta^E$=recovery factor, and $T_\eta^E$=recovery duration in minutes. If the insulin basal rate from the basal set is given by $I'_B$, then it can be determined using equation (9):

$$I_B = I'_B \left( (1 - K_\eta^E) \frac{t - t_\eta^E}{T_\eta^E} + K_\eta^E \right), \tag{9}$$

where $t_\eta^E$ is the time that the exercise was completed, and t is the current time.

Fast-Acting Carbohydrate

After finishing with the exercise module 822, the EA 815 then calls the fast-acting carbohydrate module 824 to provide an update to a glucose push vector due to an ingestion of fast-acting carbohydrates if so indicated by the patient on the user interface 512 (FIG. 5). The glucose push vector $\Delta \vec{G}_P^{FC}$ is analyzed using an expected glucose push profile and a relative glucose push profile. The expected glucose push profile is a pre-defined glucose push vector, and it is normalized per gram of carbohydrate intake and per mg/dL rise. The relative glucose push vector is the product of the normalized push vector $\Delta \vec{G}_P^{FC}$, the amount of fast-acting carbohydrates consumed in $A^{FC}$[g], and the expected glucose rise per gram of carbohydrate $K_P^{FC}$[mg/dL/g]. Thus, the glucose push vector can be described and determined by equation (10):

$$\Delta \vec{G}_P = \Delta \vec{G}_P + A^{FC} K_P^{FC} \sum_{i=k}^{end} \Delta \vec{G}_P^{FC}[i]. \tag{10}$$

Lo-Glucose Intervention

Next the EA 518 calls the low glucose intervention module 826 that maintains user safety by defining conditions that warrant the rise of the glucose value. In a low glucose situation, such as when the ALGO 510 has failed to keep the glucose level above an acceptable glycemic boundary in a timely fashion, the EA 518 will intervene based on information provided from this module. The purpose of this intervention is to bring the subject back into a normal glycemic range by the ingestion of fast-acting carbohydrates. With the EA still active, the ALGO 510 shall see the increase in the measured glucose and shall potentially counteract this glucose push by recommending additional insulin. However, the low glucose intervention module 826 allows glucose to rise with a more conservative insulin recommendation.

Figure 14:
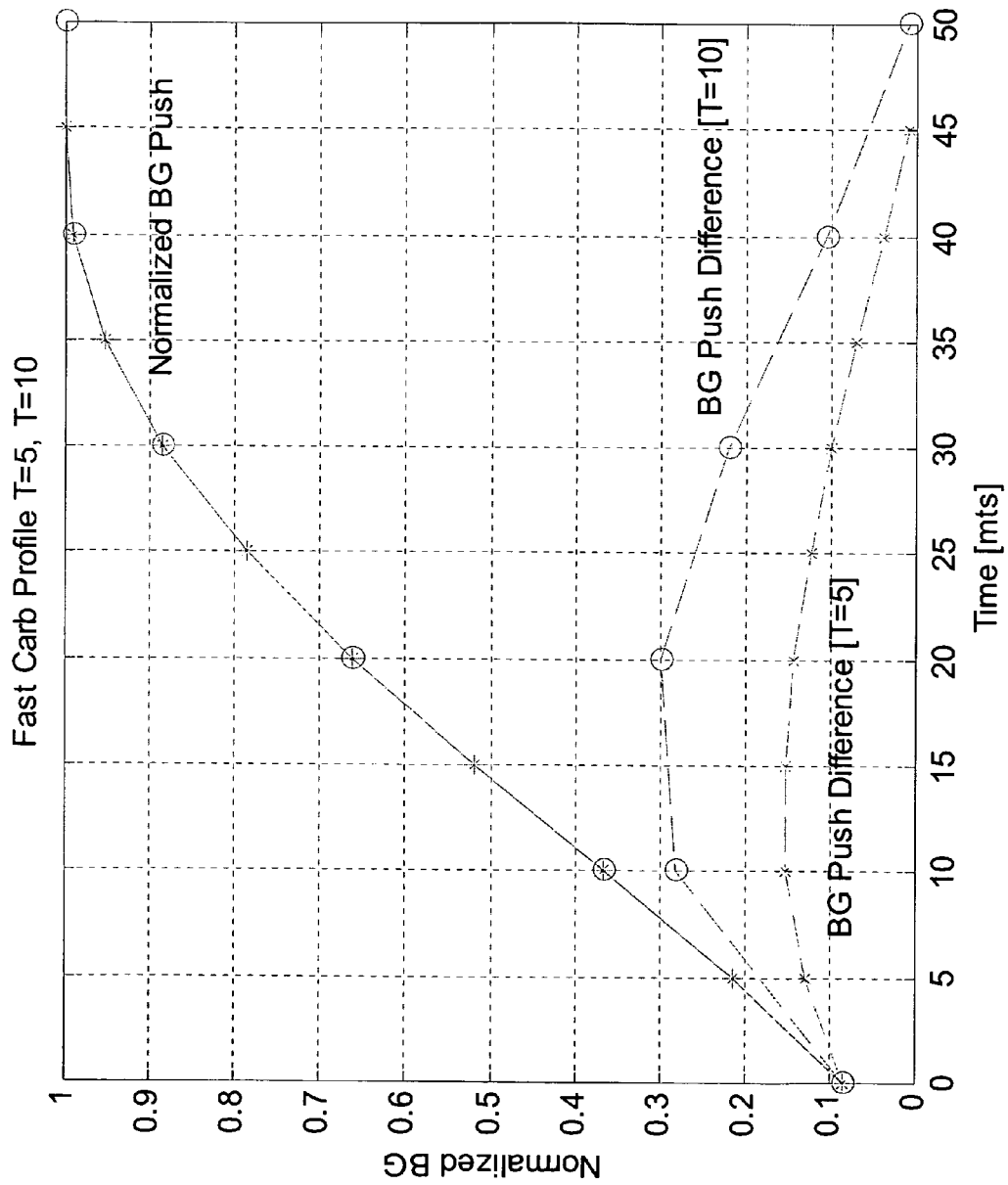
FIG. 14 is a graph showing a glucose push for a fast-acting carbohydrate intake.

In one embodiment, $A^{LG}$ is defined as the amount of fast-acting carbohydrates needed to lower the glucose level. Then the expected glucose push is given by equation (11):

$$\Delta \vec{G}_P^{LG} = \Delta \vec{G}_P^{FC} A^{LG} K_P^{FC} \tag{11},$$

where $\Delta \vec{G}_P^{LG}$ is the glucose push due to the intake of fast-acting carbohydrates, $A^{LG}$ is the amount of fast-acting carbohydrates for low glucose intervention, $K_P^{FC}$ is the glucose rise per gram of carbohydrates. FIG. 14 shows graphically the glucose push for fast-acting carbohydrate intake. By modifying the glucose set point $G_{SP}$ by an amount equal to the expected rise $\Delta \vec{G}_P^{LG}$, the ALGO 510 will not counteract the rise attributed to the intake of fast-acting carbohydrates. Also, $G_{SP}$ should eventually be restored to the original set point. The set point push vector is defined as a product of $\Delta \vec{G}_P^{LG}$ and the linearly decreasing gain term $$\left(1 - \frac{jT_C}{T_D}\right),$$

and is given by equation (12):

$$\Delta \vec{G}_{SP}^{LG}[j] = \left(1 - \frac{jT_C}{T_D}\right) A^{LG} K_R^{FC} \sum_{i=1}^{\min(j+1, len(\Delta \vec{G}^{FC}))} \Delta G_P^{FC}[i]. \tag{12}$$

Thus, the set point is given according to equation (13):

$$\vec{G}_{SP} = \vec{G}_{SP} + \Delta \vec{G}_{SP}^{LG} \tag{13}.$$

Figure 15:
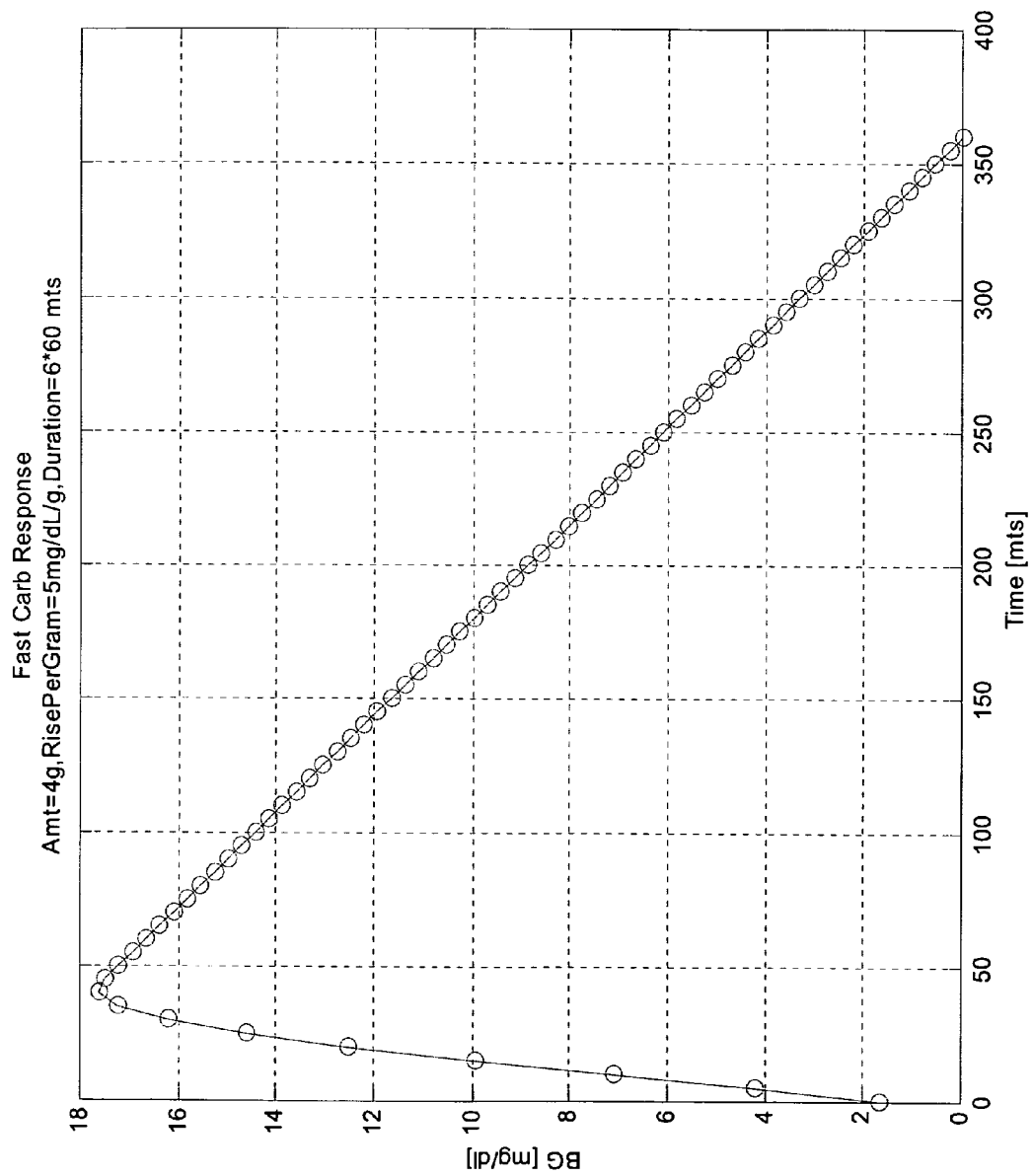
FIG. 15 is a graph showing blood glucose response to a fast-acting carbohydrate push over time.

FIG. 15 shows graphically the relative set point change over time. It is possible that multiple low-glucose interventions can occur when the glucose does not rise quickly enough. This also leads to a buildup of $G_{SP}$ due to the multiple low-glucose intervention events. The low-glucose intervention instead of adding the effects, removes the remaining trailing part of the last low-glucose intervention before adding the $\Delta \vec{G}_P^{LG}$ for the current low-glucose intervention event. After such intervention, the EA 518 calls the prep-exercise module 828, which since being discussed above in the previous section entitled "Prep-Exercise and Exercise," no further discussion is provided.

Commanded Bolus

The EA 518 uses the commanded bolus module 830 when the user commands the pump to deliver an additional bolus of insulin $A^{CB}$, through the APS 500. However, the EA 518 recognizes and implements the commanded bolus event via the ALGO 510 differently for each of the control modes. For closed loop Pure-Control mode 600 (FIG. 6), the commanded bolus event can force an early delivery of insulin, and can thus modify the future distribution of the insulin recommendations. In addition, when in the Pure-Control mode 600, the commanded bolus $A^{CB}$ will be over and above the required insulin amount needed to achieve the target glucose. Accordingly, over future control cycles, the EA 518 takes into consideration $A^{CB}$, and adjusts the recommendation accordingly. For open loop Controlled-Obs mode 700 (FIG. 7), the commanded bolus module 830 enables the subject to manage their individual therapy during Controlled-Obs mode 700 by entering via the user interface 512 (FIG. 5) the bolus to cover events such as, for example, meal intake and elevated glucose level.

Hi-Glucose Intervention

The high glucose intervention module 832 enables the EA 518 to correct a state of hyperglycemia. The user enters via the user interface 512 (FIG. 5) the correction amount $A^{HG}$ as a high glucose intervention event. The two control modes 600 and 700 deliver the intervening amount along with a recommendation, which is generated by the respective mode. Commanded bolus is "seen by ALGO" insulin, whereas insulin delivered to cover a high glucose intervention event is "not seen by ALGO". In closed loop Pure-Control mode 600, the feedback part of the ALGO 510 is blind to the amount of insulin intervention. The insulin nullification module 836 (discussed hereafter in a later section) removes the amount of insulin related to a high glucose intervention. This means that the feedback does not reduce the amount of insulin from future control actions. In open loop Controlled-Obs mode 700, the amount of intervention for high glucose levels is summed with an open-loop recommendation to provide the net insulin recommendation.

Carbohydrate Rectification Rework Last Meal Intake

After the subject has indicated consumption of meal of $A^M$ grams of carbohydrates to the ALGO 510, the possibility exists that the amount entered may have to be revised due to one of several potential reasons. These reasons include: miscalculation/incorrect prior entry; subject could not consume as much as earlier anticipated (or consumed more than anticipated); consumption of food was spread over a longer time period and hence the therapy needs to be redistributed; and in an extreme case, cancellation of the meal. With the above reasons in mind, the EA 518 calls the carbohydrate rectification module 834, which executes upon the following conditions. First, a meal event at time $t_M$ and of amount $A^M$ must exist. Second, a meal correction event at time $t_{MC}$ and amount A has been entered by the user. In an alternative embodiment, the meal event is defined as meal remaining $A_r^M$. If both condition are met, then the correction to the insulin amount and distribution is done provided the following additional condition of equation (14) is met:

$$t_{MC} - t_M \leq T_C^M \quad (14),$$

where $T_C^M$ is time in minutes and is the allowed time window for correcting the last meal entry, and $0 \leq A_r^M \leq A^M$ (only for meal remaining case). If the above last condition is satisfied, then the carbohydrate rectification module 834 is further executed, else the module returns to the EA 518 without taking action.

In the further processing, the module 834 replaces the insulin distribution obtained for $A^M$ at time $t_M$ by new insulin distribution computed for the new meal amount $A_C^M$. The distribution is implemented with respect to time $t_M$ and not with respect to $t_{MC}$. For meal remaining case $A_r^M, A_r^M, A_C^M$ is given by equation (15):

$$A_C^M = A^M - A_r^M \quad (15).$$

The module 834 identifies the last meal event occurring to the (a) time when it occurred and (b) the amount. If the assumptions 1 and 2 are satisfied, the module calculations: For $A_C^M$ find the insulin distribution. Time shift the distribution to the time when last meal occurred. For $A^M$ find the insulin distribution. Time shift the distribution to the time when last meal occurred. From the corresponding time slots do: From MEAL RELATED BOLUS vector, subtract $A_C^M$ related insulin distribution and add $A^M$ distribution. From INTERNAL BOLUS EVENT vector, subtract $A_C^M$ related insulin distribution and add $A^M$ distribution. This further processing of the carbohydrate rectification module 834 is further clarified by an example shown in FIG. 16 and discussed hereafter.

Meal is meal event and meal correction is an event performed by the carbohydrate rectification module 834. In the provided example, at time $t_M$=495 meal event of 100 g is entered which needs [2 0 5 0 0 3 0 0 2] as an insulin distribution. MEAL RELATED BOLUS until t=525 is [3 1 5] and INTERNAL BOLUS EVENT is [0 0 3 0 0 2]. MEAL RELATED BOLUS shows that there are additional insulin contributions coming, for example, from a previous meal. Its existence is important and not from where contribution is coming for the current problem. At $t_{MC}$=525 the correction to meal is entered. The information now is that for the 100 g meal entry at $t_M$=495, only 60 g was actually consumed which completes steps 1 and 2. So in step 3, the module 834 first determines insulin for 60 g which is [1.5 0 3 0 0 2 0 0 0 1.5] in step 4. Because ALGO 510 does not remember what distribution for 100 g was in step 5, it recomputed for 10 g as [2 0 5 0 0 3 0 0 2] in step 6. Both vectors (60 g and 100 g) are shifted to t=500 in step 7 (shown by arrows) and both MEAL RELATED BOLUS and INTERNAL BOLUS EVENT are recomputed in steps 8 and 9.

If carbohydrate rectification is not applicable, the following pop-up message is displayed in the user interface 512 (FIG. 5): "WARNING: Meal correction not applied." If carbohydrate rectification is applicable, then one of the following pop-up messages is displayed (depending on the amounts entered): "WARNING: Meal of (number amount) grams entered at (hh:mm) is now corrected to (number amount) grams. WARNING: Meal remaining must be between (number amount) and (number amount) grams."

Insulin Nullification

After the carbohydrate rectification module 834, the EA 518 calls on the insulin nullification module 836. As mentioned above, the insulin nullification module 836 negates feed-forward insulin components from final delivered insulin i.e., the amount of insulin dispensed for the cycle. Final insulin delivery is all insulin amounts coming from all of the EA's feed-forward modules such as, for example, self-bolus command, meal related bolus, and the feed-back component. Insulin nullification removes any feed-forward insulin amounts from the final insulin delivery. The EA 518 current implementation manages various feed-forward insulin components separately. Insulin nullification actually implies that all of the feed-forward insulin amounts have been removed. To obtain correct insulin feedback recommendations, it is imperative that all feed-forward components are correctly removed. The insulin nullified vector, $\vec{I}_N$ is given by equation (16):

$$\vec{I}_N = \vec{I} - \vec{I}_\eta - \vec{I}_S \quad (16),$$

where $\vec{I}$ is a delivered insulin vector, $\vec{I}_\eta$ is a meal related and Hi-glucose intervention boluses, $\vec{I}_S$ is a boli related to self bolus and priming, feed-forward component. Note, if past values are not available in the pump delivery data, then the past information is filled in with basal insulin doses.

Glucose Prediction and Basal Control Action

Figure 17:
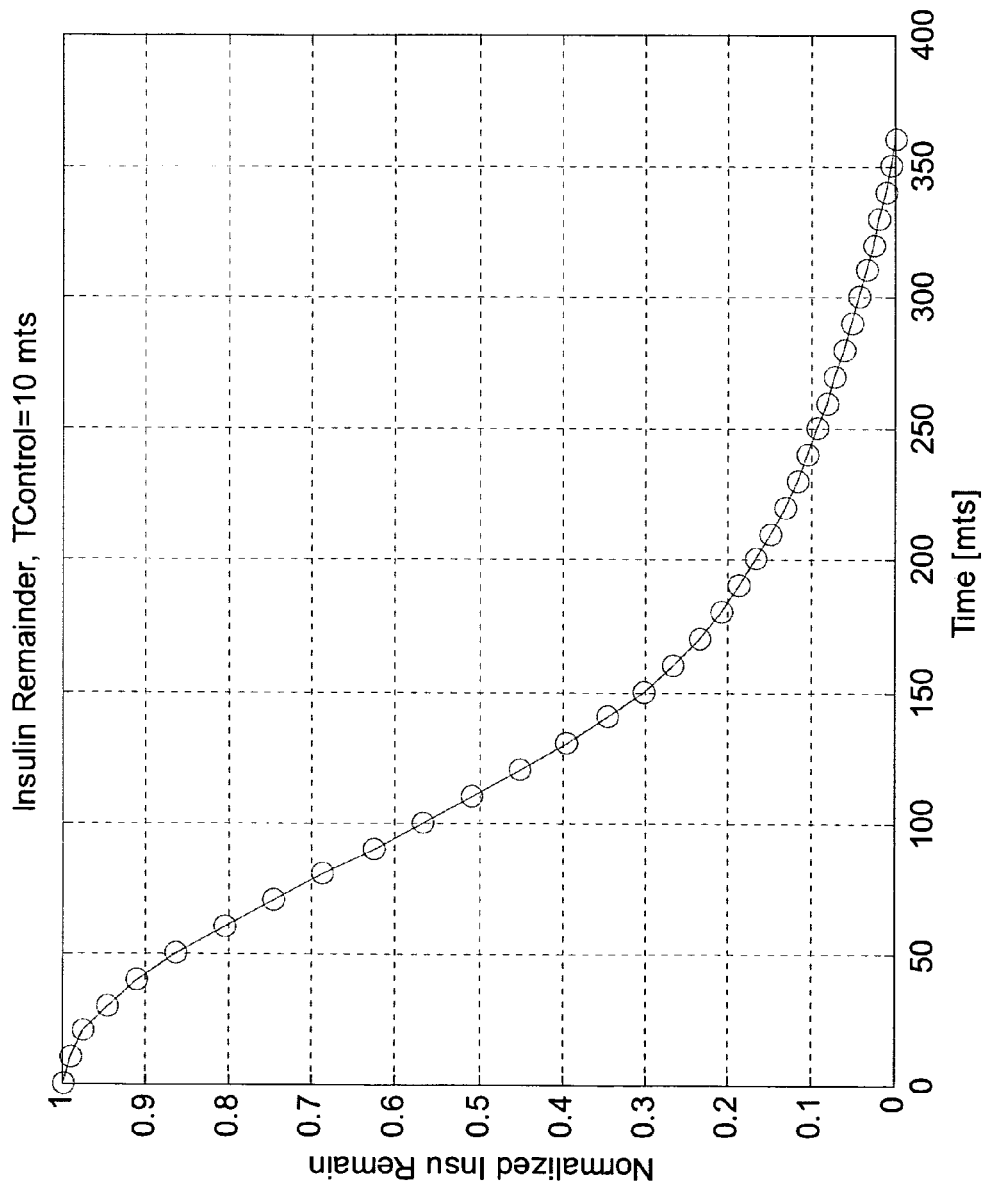
FIG. 17 is a graph showing insulin remaining pharmacodynamics.

Next the EA 518 calls the glucose prediction module 838. Glucose measurements collected by APTS are delayed measurements because the sensor has physical and process lags. Accurate glucose prediction into the future is a key for providing glycemic control. The glucose prediction module 838 makes predictions using past insulin delivery information, the glucose measurements, and using insulin pharmacodynamics. FIG. 17 shows the insulin remaining pharmacodynamics. To implement, the pharmacodynamics of insulin remaining for a unit bolus is defined in the subject.ini file and given here by $\vec{I}_r$. As shown, the pharmacodynamics for unit insulin impulse response is sampled at $T_C$=10 mts.

The basal part of the basal controller 628 is based on principles similar to those used in glucose prediction. The underlying principle is that changes in glucose levels are due to un-modeled plant disturbances that the basal controller 628 (FIG. 6) corrects. Adjustments to insulin boluses take into consideration the predicted glucose. Outputs from the glucose predictor 626 and setpoint 603 providing basal control together forms the feedback part of the basal controller 628. In summary, computation of closed loop feedback recommendation requires (a) recent predicted glucose value and (b) history of delivered insulin.

To predict glucose at a current time, the glucose prediction module 838 uses the following information. Processed glucose value, G[K] and the corresponding processed time, $t_G$[K]. Information of nullified insulin, $\vec{I}_{[-n:-1|j]}$ over last $T_D$ minutes with respect to j, where $T_D$ is the duration of the effect of insulin. If $T_C$ is the control period, then $T_D = nT_C$. Get insulin pharmacodynamics, $\vec{I}_r$. The glucose drop is assumed as directly proportional to insulin utilized, $\Delta G[i] \propto \Delta I_r[i]$ where i=1, 2, ..., n. Insulin utilized $\Delta \vec{I}_r$ for a unit bolus is obtained as forward difference performed on vector $\vec{I}_r$. The vector $\Delta \vec{I}_r$ is given by equation (17):

$$\Delta I_r[i] = I_r[i+1] - I_r[i], i=1, 2, \ldots, n-1 \quad (17).$$

Figure 18:
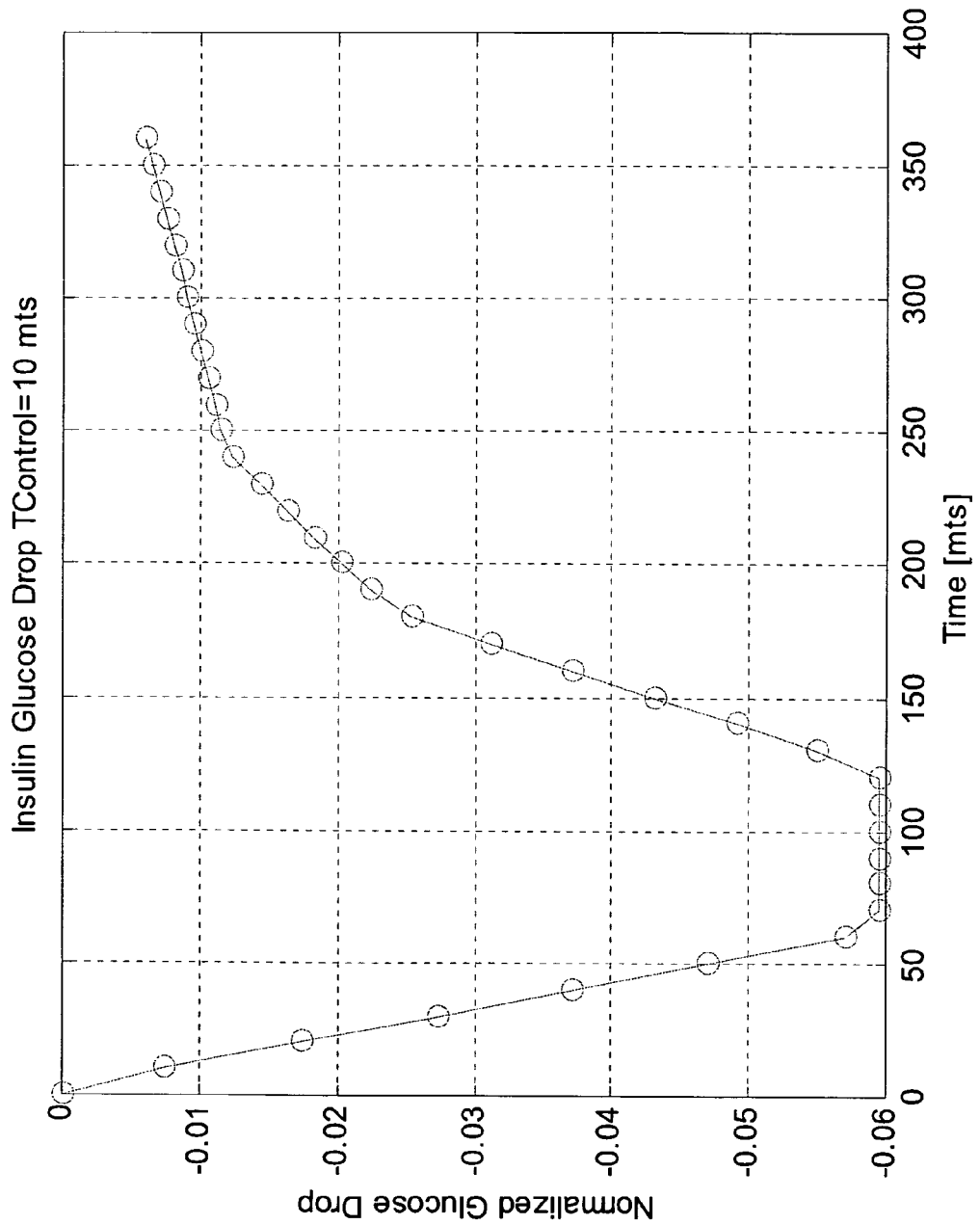
FIG. 18 is a graph showing changes to insulin for a unit bolus over time.

FIG. 18 graphically shows the changes to insulin utilized $\Delta \vec{I}_r$ for a unit bolus over time. If the constant of proportionality is $K_I$, insulin sensitivity [mg/dL/U], then glucose drop due to insulin utilization is defined by equation (18) as:

$$\Delta G[i] = -K_I \Delta I_r[i] \quad (18).$$

The glucose drop vector is defined by equation (19) as:

$$\Delta \vec{G} = K_I \Delta \vec{I}_r \quad (19).$$

Figure 19:
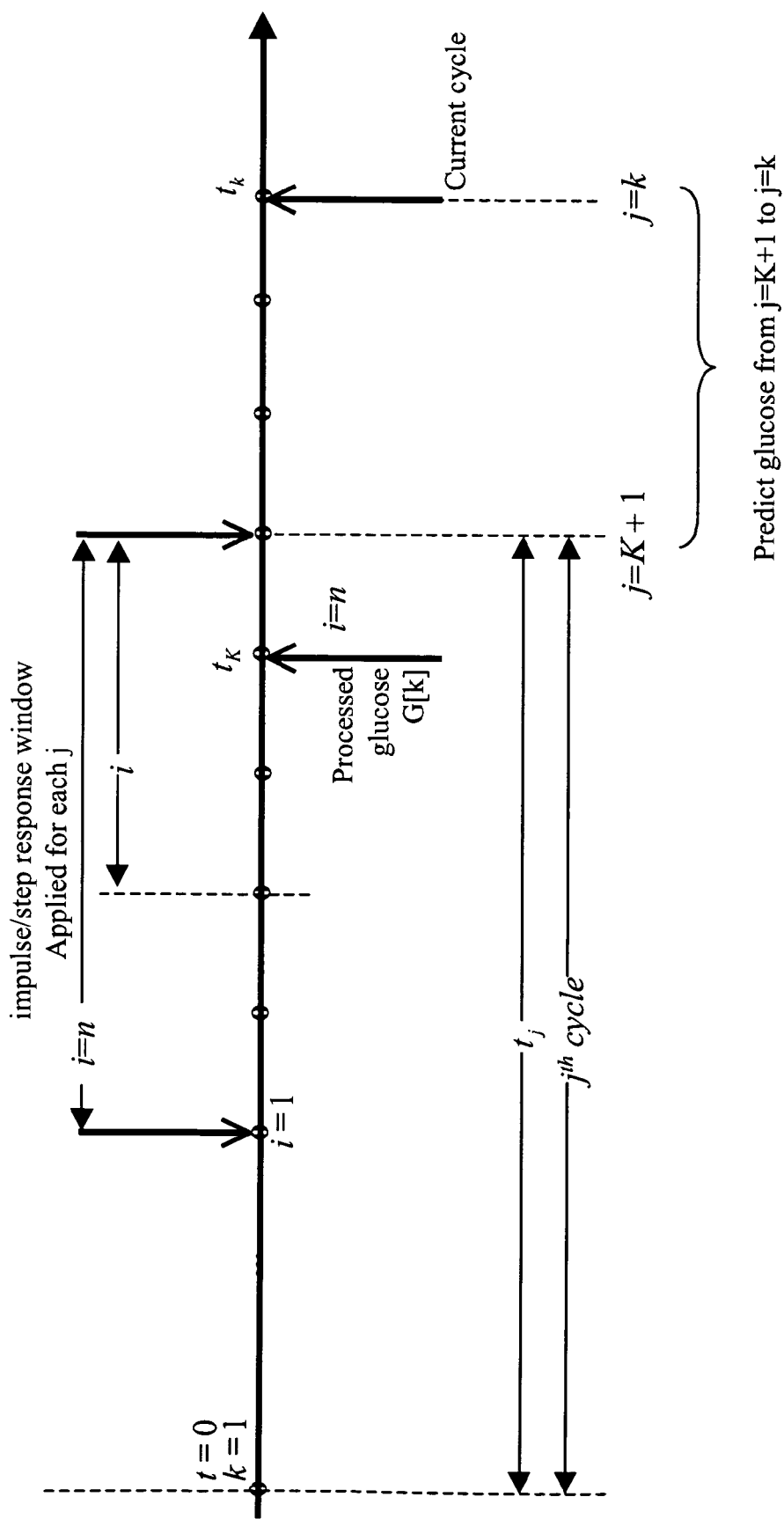
FIG. 19 is a graph showing an insulin impulse prediction.

To predict glucose drop at time j, given that the latest glucose measurement G[K] where K is the time for which glucose value is currently available, is given by convolution of nullified insulin boli vector $\vec{I}_{[-n:-1|j]}$ with AG which is defined by equation (20) as:

$$\Delta G[j] = \vec{I}_{[-n:-1|j]} * \Delta \vec{G} = \sum_{i=1}^{n} (I_{[-n+i|j]} \Delta G[n-i]), \quad (20)$$

where $\vec{I}_{[-n:-1|j]}$ is the vector of last n insulin delivered amounts with respect to point j, the glucose drop, $\Delta G[j]$ at $j^{th}$ instant, where j=K+1, ..., k cycle. FIG. 19 shows graphically the insulin impulse prediction. The glucose prediction module 838 uses equation (20) to predict glucose for some instant j. The prediction for glucose at k is done by stepping j from K+1 to k. Glucose prediction is computed from 3 parts: (a) delivered basal insulin, (b) pre-defined basal insulin, and (c) glucose prediction.

(a) Delivered Basal Insulin

Vector delivered basal insulin $\vec{I}_{[-n:-1|j]}^N$ is the nullified insulin delivery. Expected glucose drop, $\Delta G_N[J]$ is defined by equation (21) as:

$$\Delta G_N[j] = \vec{I}_{[-n:1|j]}^N * \Delta \vec{G}, j=K+1, \ldots, k \quad (21).$$

(b) Pre-defined Basal Insulin

Pre-defined basal insulin is determined from Basal Set and is the "would be basal insulin" value, $\vec{I}_{[-n:1|j]}$ with a no disturbance scenario. This is the basal insulin component required to maintain target glucose, $G_T$. Expected glucose drop, $\Delta G_B$ is given by the inner product defined by equation (22) as:

$$\Delta G_B[j] = \vec{I}_{[-n:1|j]} * \Delta \vec{G}, j=K+1, \ldots, k \quad (22).$$

(c) Glucose Prediction

Then given G[j] the glucose value at $j^{th}$ step then predicted glucose G[j+1] is given by equation (23) as:

$$G[j+1] = G[j] + \Delta G_B[j] - \Delta G_N[j] + \Delta G_P[j+1] \quad (23),$$

where, $\Delta G_P[i+1]$ is the estimated glucose push from a known disturbance. Glucose prediction is then carried forward from last known glucose value at time $t_K$ to current time, $t_k$. The EA 518 then proceeds on to the meal compensator module 840.

Meal Compensator

The meal compensator module 840 when called is concerned with the intake of carbohydrates. Proteins and fat are converted to an equivalent carbohydrate amount. Meal type is associated with time of day as well as size of carbohydrate intake. Definitions of various meal types are listed in Table 5.

TABLE 5

Definition of Meal Type

| Meal Type | Meal Amount | Amount Constraint | Time Constraint |
|---|---|---|---|
| Snack | $A_{Sn}^M$ | $A^M \leq A_0^M$ | $\forall t$ |
| Breakfast | $A_B^M$ | $A^M > A_0^M$ | $T_1^B \leq t < T_2^B$ |
| Lunch | $A_L^M$ | $A^M > A_0^M$ | $T_1^L \leq t < T_2^L$ |
| Supper | $A_{Su}^M$ | $A^M > A_0^M$ | $T_1^{Su} \leq t < T_2^{Su}$ |

It is acknowledged that one of the factors that affect the rate of gut glucose absorption, (i.e., the speed of the meal) is meal composition. Implicit to the meal amount selection, the speed of meal is accounted. In a control cycle if multiple meal events are triggered, then EA 518 considers only to the last meal entry. The distributed insulin boli to cover the meal is described in the implementation section. A large meal is not necessarily equivalent to the sum of several small meals. Such can be defined in a meal schema, for example, Small meal=25 gm, Regular meal=50 gm, and Large meal=75 gm. If the current basal insulin request is relative and a meal has been triggered, then the set point is adjusted using a FastCarb profile. Glucose is expected to rise quickly because of the meal push with dynamics like fast carbohydrates, not slowly like the insulin pharmacodynamics.

Meal Advisory

Next the EA 518 calls the meal advisory module 842 when appropriate to provide a pop-up dialog box informing the subject to start eating. If a meal-advisory pop-up is to be displayed, then a flag that controls the meal advisory module 842 is set by the basal controller 628.

Internal Bolus Management

Additionally, if appropriate, the EA 518 calls the internal bolus management 844 to deliver the feed forward boluses that result from a meal event.

Insulin Recommendation

Afterwards, the EA 518 calls the insulin recommendation module 846 to compute an insulin dose using the current predicted glucose value as described above. In particular, the insulin recommendation for an insulin dose is computed by projecting the effects of on board insulin, future basal input and effects of other events entered. The following steps determine the basal insulin recommendation: (a) current glucose, (b) delivered basal perturbation insulin, (c) glucose set point, (d) pre-defined basal insulin, and (e) glucose push.

(a) Current Glucose

Current glucose is determined from prediction glucose section and is given by G[k].

(b) Delivered Basal Perturbation Insulin

This $\vec{I}_{[-n:-1|k]}^N$ vector is the nullified insulin delivery. Then the estimated insulin remaining is $I_r^N[k]$ is given by equation (24) as:

$$I_r^N[k] = \vec{I}_{[-n:1|k]}^N * \Delta \vec{I}_r \quad (24).$$

(c) Glucose Set Point

This is the target glucose and given by $G_T$.

(d) Pre-Defined Basal Insulin

This is determined from basal set and is the "would be basal insulin" value, $\vec{I}_k^B$. This is the basal insulin component required to maintain target glucose, $G_T$. Expected insulin remaining, $I_r^B[k]$ is given by the inner product define by equation (25) as:

$$I_r^B[k] = \vec{I}_k^B * \Delta \vec{I}_r \quad (25).$$

(e) Glucose Push

Glucose push is given by $\Delta G_P$. Accordingly, the insulin recommendation is then given by $I_{req}$ as defined by equation (26) as:

$$I_{req} = \frac{(G_{estimate} - G_T)}{K_I}, \quad (26)$$

where $G_{estimate}$ is given by equation (27) as:

$$G_{estimate} = G[k] + [-K_I(I_r^N[k] - I_r^B[k])] + \Delta G_P \quad (27),$$

and is determined by taking into account the steps (a) through (e).

The following cases modifying the insulin recommendation are glucose satisfying the target zone, and a minimum basal requirement. As mentioned above in a previous section, the target zone (i.e., target 601) is defined as a set region having a lower and upper set point range rather than just a single point, e.g., let $G_T^{Hi}$ and $G_T^{Lo}$ define the upper and lower set points respectively. If the estimated glucose $G_{estimate}$ is within the target zone then $I_{req}$ is simply basal insulin. For the minimum basal requirement case, when $I_{req}$ is negative, the EA 518 has predicted that the subject is currently in a state of insulin over-delivery. A minimum basal rate (typically half the basal rate) is implemented by the ALGO 510 during such over delivery circumstances. It is important that circulating insulin concentrations never decline below a threshold value to avoid counter regulation. Enforcing minimum basal ensures minimum circulating insulin levels.

Insulin Bucket

When the EA 518 calls the insulin bucket module 848, a final insulin recommendation is made from combination of basal control and open loop insulin requirements due to various events triggered. Additionally, there are constraints imposed on final insulin recommendations such as, for example, a cap on the insulin amount for each control cycle, which is called the delivery ceiling constraint. Finally, the insulin recommendation may not get implemented. For example, the healthcare professional is the final authority of accepting or rejecting a recommendation. The final insulin delivery is the actual delivery. Therefore, the insulin record-keeping components, which are maintained in the various insulin buckets, must conform to recommendation constraints. If the final insulin recommendation differs from the final insulin delivery, then ALGO 510 re-assesses and re-accounts the components to the revised final insulin delivery accordingly.

At process point 850, the EA 518 determines whether open loop Pure control 600 is enabled, whether the not enough bG measurement flag is set (which is the reenter point from process point 816), or whether the bG outdate flag is set. If any such conditions are false, then the EA 518 calls the update storage module 854 to save the value and conditions from this control cycle. If any of the conditions are true, then the EA 518 will call the discrepancy management module 818, the command bolus model 830, the High bG intervention module 832, and a delivery ceiling constraint module 852 which imposes constraints on final insulin recommendations. At the completion of these calls, the EA 518 will then call the update storage module 854 to save the value and conditions from this control cycle. The EA 518 then waits until the start of the next control cycle of the ALGO 510 before restarting the process flow shown by FIGS. 8 and 9 and described above.

Algoshell

Figure 33:
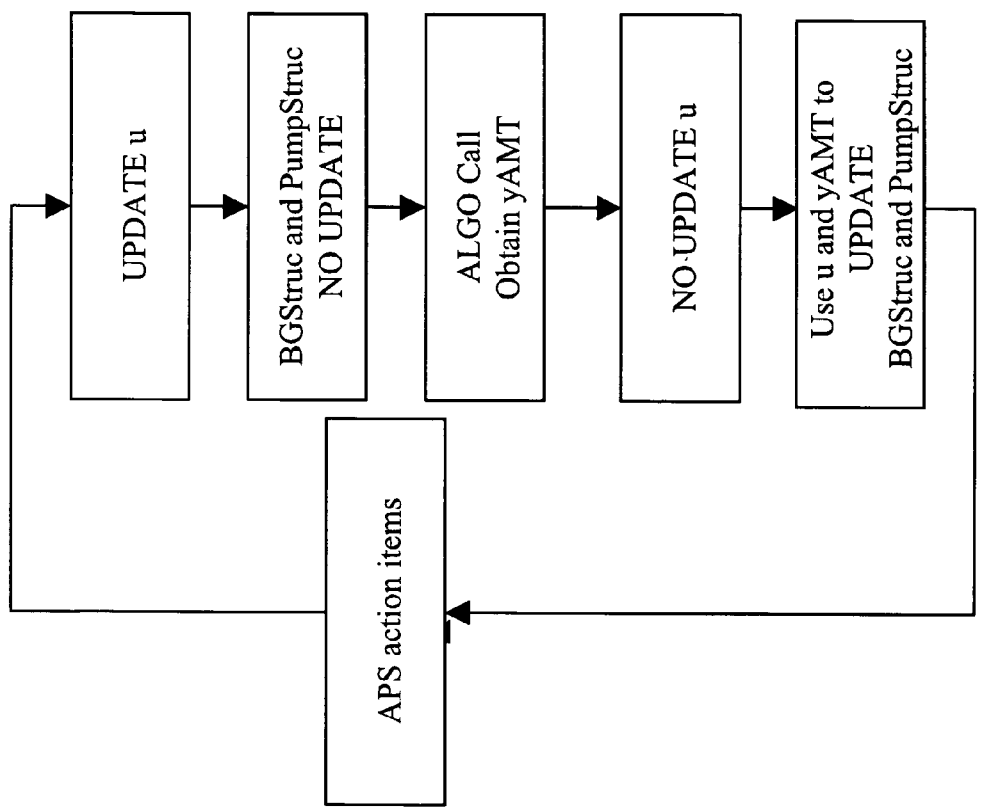
FIG. 33 is a process flow showing a run sequence of software components according to an embodiment of the present invention.

ALGOSHELL 506 provides data structure management and related macros which is located in a system folder. In particular, ALGOSHELL 506 is a function that generates output to given inputs called from APS 500. The ALGOSHELL 506 function also works with the APSe that runs in the simulation (Simulink) environment. As mentioned above, the APS test-stand environment is a non-Simulink environment, where APSe is a wrapper function that simulates the APS test-stand environment. ALGOSHELL 506 interfaces with APS, the real-time test-stand and APSe in a simulated environment. The standardized ALGOSHELL 506 call is as follows: [yAMT, yAdvice, yTrace, xk']=AL-GOSHELL_xxx (t, xk u, EventStruc, ExperimentStruc, PumpStruc, BGStruc, PatientIniStruc). FIG. 33 shows when the variables will be updated with respect to ALGO 510. The input variables t, xk u, EventStruc, ExperimentStruc, PumpStruc, BGStruc, PatientIniStruc of the ALGOSHELL 506 call is discussed first hereafter followed by the output variables yAMT, yAdvice, yTrace, and xk'.

Input Variables

The term t is a time scalar for the elapsed or simulation time. Time t is expected to be a multiple of TControl +/− delta time for Sync1 call and is defined as the current control-cycle edge. Sync2 call will follow Sync 1 and will occur before the next control-cycle edge. The term xk is a state vector which contains a set of variables required by ALGOSHELL referred to as states. In APSe, these are the discrete states maintained by controls that update of the discrete states. When APSe is called, xk is available as states. On the other hand, the APS is always in control and is responsible for maintaining xk. The length and specifics of vector xk are ALGO-dependent. The APS does not need to know the length or the specifics of xk. Variable xk should be initialized to empty matrix [ ] by the APS. ALGOSHELL 506 will then determine its correct length the first time it is called. From then on the experiment should maintain the length of xk. APS/APSe should not modify the values or the length of xk. The term u is the input vector and consists of information output by field devices, i.e., pump and sensors. Both APS and APSe need to know the details of the input vector, u. See Table 6 for details. Note, "Net Dispensed Insulin" is a cumulative counter for the total amount of insulin dispensed by a pump.

TABLE 6

| Vector Element | Input vector, u | |
|---|---|---|
| | Sync1 Call | Sync2 Call |
| u(1) | bg-1 measurement from APSIO (last received value) | |
| u(2) | Timestamp, min (last received value) | |
| u(3) | Flag (N/A for APS) | |
| u(4) | bg-2 measurement from APSIO (N/A for APS) | |
| u(5) | Time stamp, min (N/A for APS) | |
| u(6) | Flag (N/A for APS) | |
| u(7) | Net Insulin Dispensed by Pump 1 from APSIO, U | Commanded bolus value @ end of synchronous call or asynchronous call, U |
| u(8) | Time stamp associated with Pump 1, min | Timestamp associated @ ALGO (time at which APS makes Sync2 call), min |
| u(9) | Flag values: 10-19 recommendation mode (device status) (N/A for APS) | Flag values: 0-9 Conversion mode (device status) (N/A for APS) |
| u(10) | Net Insulin Dispensed by Pump 2 from APSIO (N/A for APS) | (N/A for APS) |

TABLE 6-continued

Input vector, u

| Vector Element | Sync1 Call | Sync2 Call |
|---|---|---|
| u(11) | Time stamp (N/A for APS) | (N/A for APS) |
| u(12) | Flag (N/A for APS) | (N/A for APS) |

NOTE:
Just before the ALGOSHELL Sync1 call, the u vector is filled with the latest values obtained from the devices (stored in the database.
Async call: APS calls the ALGO 510 at the end of an Async call the user requests bolus, it is passed through u(7). For APS-3 Async calls are not available.

EventStruc—Event structure

This is a structure that contains the predefined trigger schedule. It is available to APSe as one of the parameters. APS, on the other hand, obtains the schedule and updates EventStruc from events triggered from the APS main window 902. See Table 7 for event structure fields.

TABLE 7

EventStruc fields

| Field | Definition | Notes |
|---|---|---|
| trigger_time | Time at which an event takes place, lapse time, min | n by 1 array<br>Append new entry.<br>Entry is needed for ALGO 510 to take any action. |
| rxn_time | Time at which the controller should respond to the event, lapse time, min | n by 1 array<br>Append new entry.<br>Default is NaN. |
| event_type | Type of event identified by the row number of the event defined in PatientIniStruc.events.type. The unit type of event strength is defined in PatientIniStruc.events.units. | n by 1 array<br>Append new entry.<br>Default is NaN.<br>event_type is indexed per event in PatientIniStruc.events.type. |
| duration | Duration of the impact of an event (physiological), min | n by 1 array<br>Append new entry.<br>Default is NaN |
| amount | Event quantified, units as defined in type of events<br>Meal, gm<br>Exercise<br>Bolus, U<br>Blood glucose, mg/dL | n by 1 array<br>Append new entry.<br>Default is NaN. |

The field PatientIniStruc.events.units provided in Table 7 is an array of event units that is displayed by the APS GUI. Each of the fields in EventStruc is a column array. All of the column arrays will be of same length. If a particular row does not have information, NaN will be entered and the lengths of the rows will be maintained. In APS, EventStruc is updated when an event is logged. In APSe, EventStruc is pre-existing. All the events are scheduled prior to run. In essence, there is no difference in the implementation. ALGOSHELL 506 sees only registered events that are less than or equal to current simulation time. At least one of trigger time or controller response time has to be nonzero for the ALGO 510 to accept the event as a meaningful event. If neither of the times is entered, the ALGO 510 cannot judge when that particular event occurred and will ignore it. Event-type entries are those listed by "patientini.events" structure and have the fields of type, units and InternalName. They can vary from experiment to experiment. Events are of two kinds: events that are used only for logging purposes only for, e.g., Blood Draw event; and events that inform ALGO 510 to take into consideration and react appropriately to an event, e.g., breakfast.

ExperimentStruc—Experiment structure

This is a structure that is predefined and available to APSe via APSe parameters. APS loads Experiment Structure for an experiment run. See Table 8 for experiment structure fields.

TABLE 8

Experiment Structure fields

| Field | Definition | Notes |
|---|---|---|
| operator | Login ID | |
| timestamp | Timestamp, min | |
| algo_used | Name of algo used | Obtained from PatientIniStruc.<br>Does not change for an experiment. |
| title | Experiment title | Obtained from PatientIniStruc |
| time_int | Length of control cycle, sec (TControl, i.e. time between consecutive 1$^{st}$ ALGO call | Obtained from PatientIniStruc |
| t_zero | [year month day hour minute sec]<br>MATLAB format time | Start of experiment in absolute time. APS time stamps the start of the experiment |
| confirm_int | Confirmation time limit, sec | Default mat file |
| confirm_offset | Confirmation offset, sec | Default mat file |
| offset_int [revised fieldname] | | |
| Site | "01", "02", or "RD" | Obtained from PatientIniStruc |
| Version | Patient ini version | |
| algo_used | | Obtained from PatientIniStruc |
| AlgoShell | Name of ALGOSHELL | Obtained from PatientIniStruc |
| Algoshell_version | | Query Algoshell and assign |
| Algo_version | | Queried and stored by APS |

TABLE 8-continued

Experiment Structure fields

| Field | Definition | Notes |
|---|---|---|
| ExpDate | Expiration Date | Obtained from PatientIniStruc |
| Mode | 1 - pure observation<br>2 - pre-recommendation<br>3 - pure control<br>4 - $2^{nd}$ call/async call<br>5 - post-recommendation | APS sets the mode. For APS3 the entire run is Mode 3 followed by Mode 4: Pure-controlcall followed by $2^{nd}$ call |
| ControlObs | Flag:<br>1 - controlled observation<br>2 - pure control | Applicable to APS3 and higher. APS sets this flag and is function of Control button on the main GUI |
| DataPath | Location to store Rundat mat file | When ALGO fails, the local variables are saved in a mat file. |
| num_timeouts | Confirmations missed/timed out | |
| num_asyncs | Number of async commanded boli | |
| num_recos | Number of algo-recommendations | |
| num_ovrs | Number of user over rides | |
| patientini(i, 1) | Array of structures | Obtained from patient ini mat files. |
| PatientIni_LoadTime | Array of times | |
| single_dose_lim | Dose ceiling imposed by APS, U | |

PumpStruc—Pump Structure

Except for data fields, all fields of this structure are predefined and obtained from user interfaces of APCATS 900. This structure is initially passed as a parameter. In the initialization stage, PumpStruc becomes a mat file. APS has a similar setup. As used herein in Table 9, "Offline" means the condition which occurs when the pump is not available as per last status information from APSCOM 504. See Table 9 for pump structure fields.

TABLE 9

PumpStruc fields

| Field | Definition | Notes |
|---|---|---|
| fluid1cmdtimestamp | Time at the end of Sync call and Async call (i.e., time at which the ALGO generated pump commands are sent to APSIO,), min | n by 1 array |
| fluid1chan | Channel number | |
| fluid1cmdindx | Used to indicate the source of the respective pump command.<br>0 - No response<br>1 - ALGO<br>2 - Sync<br>3 - Async | n by 1 array |
| fluid1cmdrate | Amt/time, commanded rate, to pump | n + 1 by 1 array, yAMT(2) |
| fluid1conc | Insulin concentration, U/ml | 100 for 100U, 40 for 40U |
| fluid1vol | Reservoir volume, ml | |
| fluid1units | Unit of input quantity to the pump device - "U/cycle", "U/min", "U/hr", or "mU/min" | |
| fluid1cmdtype | 0 - continuous<br>1 - bolus<br>2 - Set no command | |
| fluid1type | "Regular", "NPH", "Lispro" | |
| fluid1device | Pump type | "507c", "D-TRON" |
| fluid1device_sn | Device serial number | |
| amt1recco | U | n by 1 array, yAMT(4), algo recco |
| amt1decided | U | n by 1 array, yAMT(4), final decided |
| amt1delivered | amount delivered previous cycles, U | n by 1 array, yAMT(5), |

TABLE 9-continued

| PumpStruc fields | | |
|---|---|---|
| Field | Definition | Notes |
| amt1deliveredtimestamp | Time at which the net insulin dispensed by the pump is noted by APSIO, min | n + 1 by 1 array, u(8) |
| Pump1frequency | clicks/min | Number of clicks/min = 25 (suggested) |
| Pump1volresolution | ml/click | .001 ml/click |
| max1rate | U/Hr | |
| min1rate | U/Hr | |
| online1 | 1 or 0 | If existing then online or offline |
| available1 | Existence of pump, 1 or 0 | |
| BasalProfileA | Multiples of 0.1U | Obtained from Disetronic pump 24 by 1 array $1^{st}$ 24 values hold values from 0 hr, 1 hr, 2 hr . . . 23 hr. |
| BasalProfileB | Multiples of 0.1U | Obtained from Disetronic pump 24 by 1 array $1^{st}$ 24 values hold values from 0 hr, 1 hr, 2 hr . . . 23 hr. |
| fluid2cmdtimestamp | min | n by 1 array, u(11) |
| fluid2chan | Channel number | |
| fluid2cmdindx | Not used | |
| fluid2cmdrate | Amt/time, commanded rate to pump | n + 1 by 1 array, yAMT(6) |
| fluid2conc | Insulin concentration | |
| fluid2vol | Reservoir volume | |
| fluid2units | | |
| fluid2cmdtype | | |
| fluid2device | Pump type | |
| fluid2device_sn | Device serial number | |
| amt2recco | Commanded rate, disp, U/hr | n by 1 array, yAMT(8) |
| amt2decided | Amount delivered previous cycles, U | n by 1 array, yAMT(9) |
| amt2delivered | Commanded type to pump, unitless | n + 1 by 1 array, yAMT(7) |
| amt2deliveredtimestamp | | |
| max2rate | | |
| min2rate | If existing then online or offline | |
| online2 | Existence of pump | |
| available2 | | |
| total_insulin | Net insulin delivered by all pumps (2 in this case), U | 1 by 1 array, yAMT(1) |

NOTE:
APS/APSe updates the PumpStruc just after ALGO call.
APS/APSe saves all of ALGOSHELL 506 input arguments after completion of Sync1 and Sync2 calls.
Input to the pump is in U/control cycle, so the final answer should be converted accordingly.
"507c", "D-TRON" are pump brands useable with the APCATS 900.

BGStruc—Blood-Glucose Structure

Except for the data fields: bg1data and bg1timestamp, all fields of this structure are predefined and obtained from the user interface of APCATS 900. This structure is initially passed as a parameter. Sensors are numbered as 0, 1, 2, 3 . . . with Sensor 1 considered to be the virtual sensor. Table 10 gives the sensor structure fields for Sensor 1. For other sensor numbers, the "1" in each of the fields is replaced by the sensor number. Up to 4 sensors are supported: 2 SU's, 1 External and 1 virtual sensor. However, for APS-3, we have the following mapping for sensors: 0 to "EXT"; 1 to "SU 1"; and 2 to "SU 2".

TABLE 10

| Sensor structure fields | | |
|---|---|---|
| Field | Definition | Notes |
| bg1timestamp | Lapse time, min | n by 1 array, u(2), just after ALGO is called |
| bg1chan | | |
| bg1data | Glucose concentration | n by 1 array, u(1), just after ALGO is called Units specified by bg1units |
| bg1indx | Last dataset index | |

TABLE 10-continued

Sensor structure fields

| Field | Definition | Notes |
|---|---|---|
| bg1units | Units of the bg1data information (units of reported blood-glucose measurement), "MG/DL", or "MMOL/L" | Internal standard for glucose concentration is mg/dL. |
| bg1device | "Via", "PR 1", "SU 1", "SU 2", or "EXT" | |
| bg1device_sn | Serial number | |
| bg1sensor_lot | Lot number | |
| bg1dispo_lot | Disposable number | |
| online1 | If existing then online or offline, 0/1 | |
| available1 | Existence of sensor, 0 or 1 | |
| bg1res | Specified precision of sensor, mg/D1 | |
| bg1PrimeStat | Indicates which sensor is currently the primary | |
| bg1lagtime | Lag time, mts | |
| bg1lagtimeindx | Index of the current lag time | |
| bg1rectime | Time at which block of BG data was received, mts | |

Just following the ALGO call, and APS/APSe updates the BGStruc fields.

PatientIniStruc—Patient Initialization Structure

This structure is defined in an initialization file (INI-file) and includes patient-specific response vectors to meal intake and insulin degradation. The INI-file provides study-specific and subject specific parameters to the APTS 500 and ALGO 510. Subject INI file loaded when APS is launched that contains subject-specific data, including algorithm parameters, single dose auto-confirm and three dose confirmation thresholds and Event Types. Event Types as explained above are activities that can be manually selected during the experiment by the healthcare professional through a dropdown list. Common Event Types include meals and external blood glucose (bG) meter readings. Dropdown list values are determined by Subject INI file. Consecutive-Dose Threshold, as designated in the Subject INI file, is the maximum amount of insulin to be delivered in three successive cycles without healthcare professional approval. Auto-confirm threshold, as designated in the Subject INI file, is the maximum amount of insulin to be delivered in a single cycle without healthcare professional approval. Experiment is the data collected from start to end of the APTS, including any intermediate restarts and changes in INI-Files. See Table 11 for field descriptions of the field provided in the subject INI file.

TABLE 11

PatientIniStruc fields

| Field | Definition | Notes |
|---|---|---|
| title | Title | 15 characters<br>Displayed as Study ID on APS window |
| pat_id | Patient ID | 11 characters<br>Displayed as PATIENT ID on APS window |
| time_int | sec | TControl |
| gender | Gender, "M" or "F" | 1 character |
| ht | Height, in | |
| wt | Weight, lb | |
| Site | "RD", "01", or "02" | |
| Version | | |
| ControlNos | | |
| AlgoShell | AlgoShell_A2M | |
| IniFilename | | 13 characters<br>Displayed as PATIENT INI on APS window |
| StartDate | | |
| ExpDate | | |
| IniCreationDate | | |
| LockoutMode | 0 - Purely controlled obs<br>1 - Allow user to switch between controlled obs and pure control | |
| PlaceOfBirth | N/A | N/A |
| ExpParam | A structure unique to each ALGO and for internal ALGO use. Groups all the additional ALGO related variables. Check for two fields:<br>algo_used<br>algodir | "algo_used": Displayed as ALGO NAME on APS window<br>"algodir" is the directory containing the mfile described by: algo_used<br>MatlabPath setting should include two paths:<br>C:\apsv3_0\algos and C:\apsv3_0\algos\algodir (where algodir is the stored string)<br>There should not be any other algos subfolder listed. |

TABLE 11-continued

PatientIniStruc fields

| Field | Definition | Notes |
|---|---|---|
| | | "USER_ENTRY_INSU_CEILING" |
| | | "SimuALGOPARAM" |
| | | "DispALGOPARAM" |
| | | "LOGFILEMSG_DEBUG" |
| | | "MildHypo" |
| | | "SevereHypo" |
| dose_confirm_thresh | Current dose ceiling, U | |
| three_dose_confirm_thresh | Last three dose ceilings, U | |
| events | | Event mapping and has following fields: type: Displayed in dropdown list of event types. Descriptor used for the user. units: Units for the selected InternalName: Internal to ALGO |

Output Variables

The term yAMT is a pump and display command vector, and contains commands for the pump. Table 12 provides details on the commends contained in the command vector yAMT.

TABLE 12 yAMT vector

| Vector Element | Definition | | |
|---|---|---|---|
| yAMT(1) | Cumulative amount dispensed, U | u(7) + u(10) | Convert to U |
| yAMT(2) | Commanded rate, U per control cycle | ALGO computes | Pass to APSIO, as is |
| yAMT(3) | Commanded type complement yAMT(2) 0 - continuous 1 - bolus 2 - Set no command | ALGO computes | Pass to APSIO, as is |
| yAMT(4) | U | 0 for pure observation 0 for pre-reco recco-calcu value for Sync1 user-value for Sync2 | Sync 1 - algo-recommended amount Sync2 - user-approved amount Async - Additional user-requested amt |
| yAMT(5) | Amount dispensed per control cycle, U | During Async call this is NaN | APSIO provides net amount dispensed, u(7), which is converted to U. The amount dispensed in the previous cycle by pump 1 is then obtained by subtracting sum(pumpdat.amount 1delivered) from u(7) |

The term yAdvice is an advisory string which provides warnings and other possible failsafe measures flagged by ALGO but implemented by APS. The yAdvisory string is composed of a two-digit advisory number, followed by a space, followed by a statement. The advisory numbers fall into three categories: (1) Nominal (range: 00 to 09), (2) Pop up a message window (range: 10 to 98), and (3) Exit/Quit (range 99). The term yTrace is a trace string that tracks the steps of ALGO execution. ALGO progress is recorded in a log file located in the DataPath defined in ExperimentStruc file. xk' is a state vector which is needed for the startup of ALGO at the next ALGO call.

Control-Cycle Breakup

Figure 34:
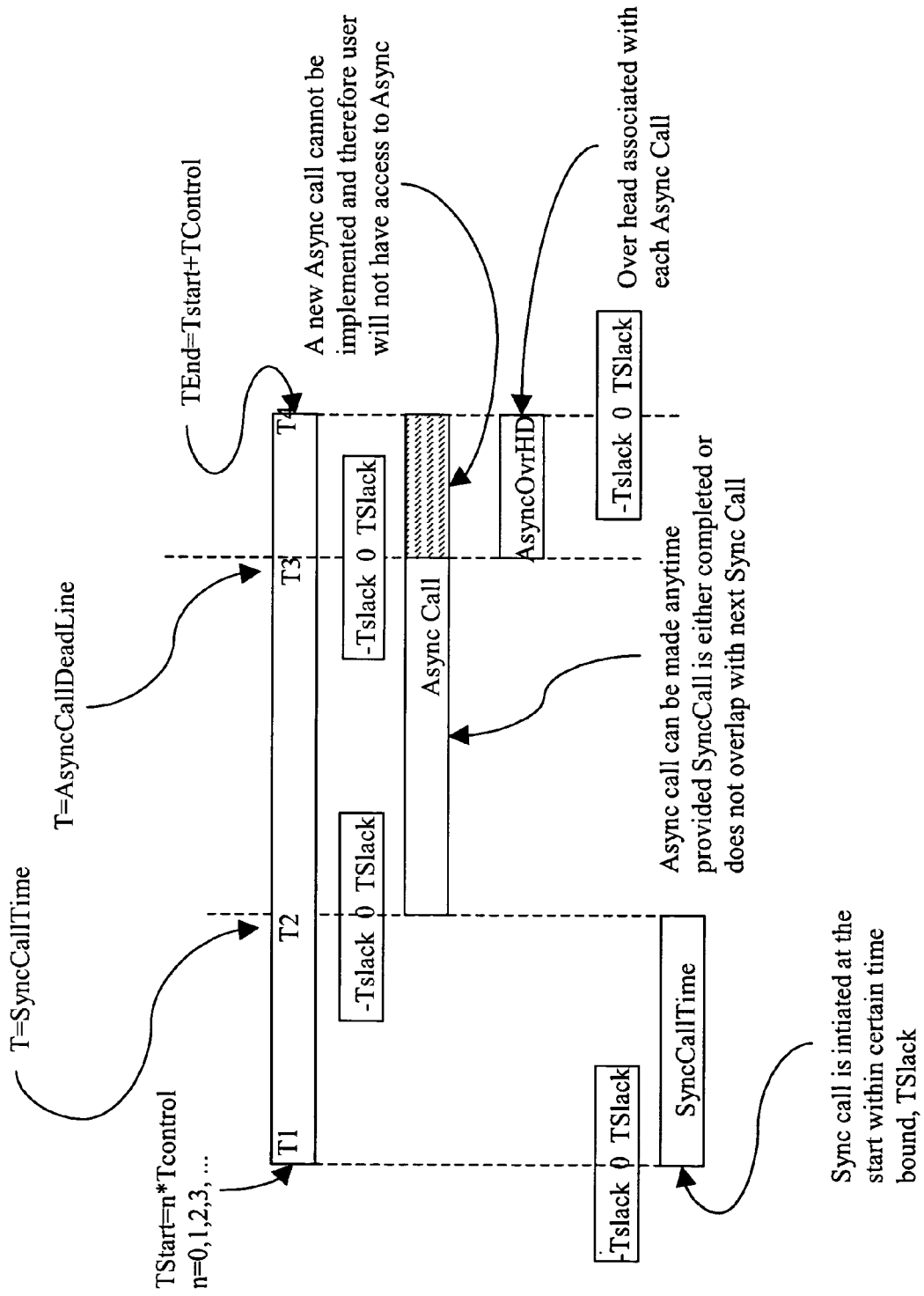
FIG. 34 is a graph showing a control period according to an embodiment of the present invention.

For the recommendation mode, which includes synchronized calls, the user confirmation window, and asynchronized calls, each commanded value is constrained to the amount the pump can dispense in the remaining portion of the control period. The confirmation Window is a dialog box that requests the final confirmation of the commanded insulin, and appears when the healthcare professional manually accepts or rejects an insulin recommendation. In an illustrated embodiment, this window times out after 45 seconds. As such, the control period is broken down into three regions as shown by FIG. 34, and the parameters in ALGOSHELL are listed in Table 13. Each control cycle in the ideal case will allow the ALGO to be called at start of the control cycle. The ALGO will process the input and recommend an amount to be dispensed in the remaining part of the control cycle. But there are hardware limitations because (1) each action takes a finite time and (2) the internal time clock is discrete. In addition, there is human intervention and, for open loop control, there is variability in the actual time left for control action. After factoring in all of these considerations, a commanded value that will allow delivery of the command in total is determined.

TABLE 13

Parameters in ALGOSHELL

| Parameter | Time, sec |
|---|---|
| TSetDev | 5 |
| TMonitor | 6 |
| TRecco | 20 |
| TSetAPS | 10 |
| TSlack | 6 |
| T2Override | 30 |
| SyncCallTime | |
| AsyncOverhead | |
| AsyncCallDeadline | |

All white blocks indicate that the enclosed variable is updated. FIG. 33 is seen from APS view point. The input data is shown before and after "Sync1" call.

Pure Recommendation Scenario

If m is the last call of ALGOSHELL 506 under control, between the $m^{th}$ and $(m+1)^{st}$ call, BGStruc is updated with the new measurements. These measurements are obtained from the database. Prior to $m+1^{st}$ ALGO 510 calls the following: (a) the latest (last) BG measurement and time as well as sensor status from BGStruc which are assigned into vector u; (b) the last net insulin dispensed information which is obtained from database and assigned to vector u; (c) time t which is set to time at which ALGOSHELL 506 is called; (d) vector xk is passed by APS as is; and (e) experiment pump Mode is set to 3. ALGO 510 is called again, n=m+1. ALGOSHELL 506 is called with Mode=3, i.e. as a Sync1 call.

Figure 35:
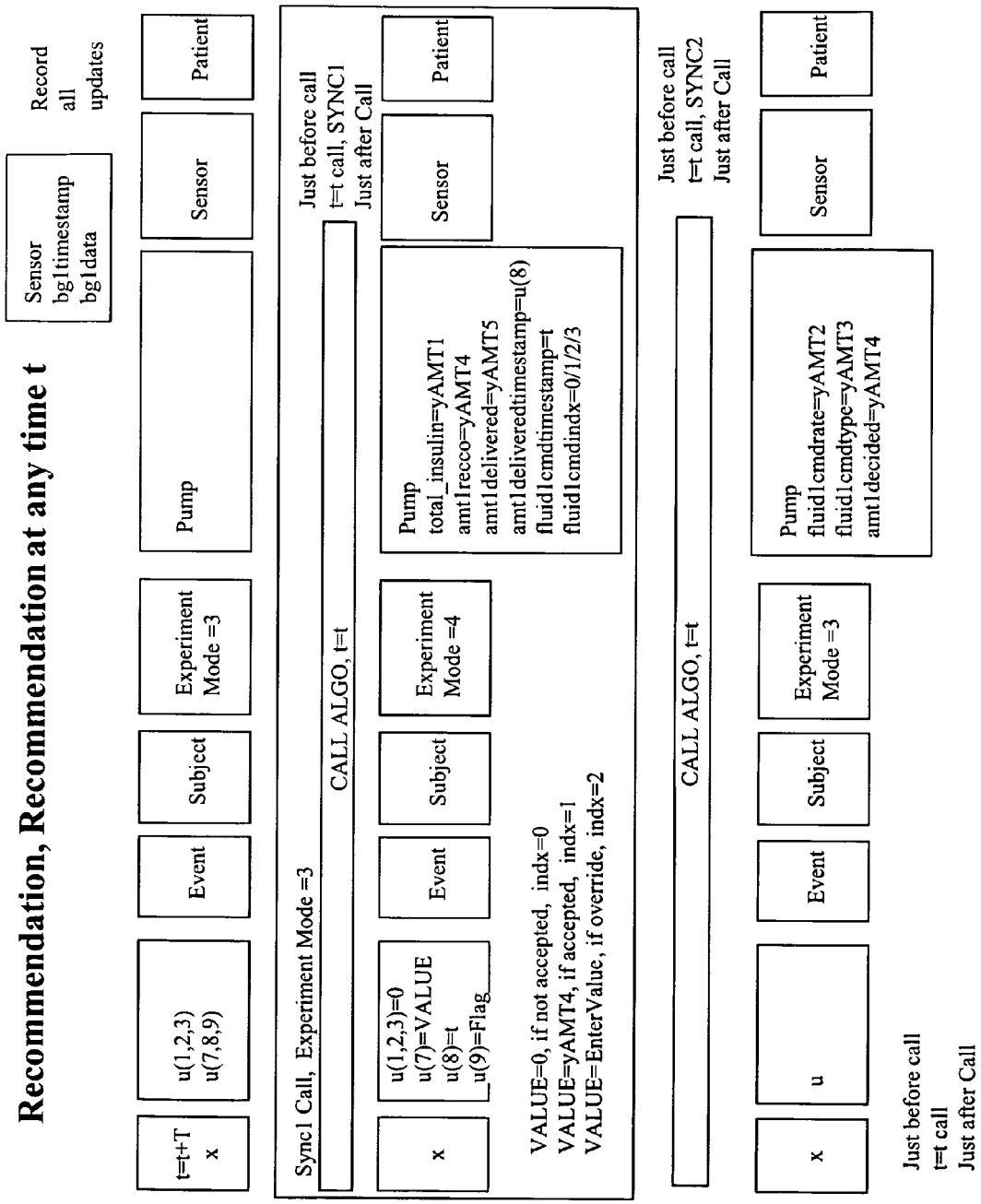
FIG. 35 is depicts an update of variables with respect to algorithm call according to an embodiment of the present invention.

For the Sync1 call, vector yAMT and other output arguments are returned. APS does an update shown in FIG. 35 using yAMT. yAdvisory is analyzed and appropriate messages are displayed (sending to log window, popping a message box, and quitting). The recommended amount yAMT(4) is displayed by APS Recommendation window 514 (FIG. 5). The Recommendation window 514 displays the recommended insulin dose for the current cycle, as determined by the ALGO 510. The Recommendation Window 514 appears at the end of a run cycle with the recommended amount of insulin to be infused. If the amount is within the single- or three-dose threshold, it does not need to be confirmed by the healthcare professional to be infused. User response is obtained which are: (a) recommendation declined, VALUE=0, indx=0; (b) Recommendation accepted (confirmation), VALUE=yAMT(4), indx=1; or (c) Override, VALUE=EnterValue, indx=2). Pumpdat vector is updated. The following assignments as show by FIG. 35 are made: for pumpdat update, u elements related to sensor are zeros; u(1) through u(6) are NaN, and u(7) is assigned VALUE; u(8) is current time t; and u(9) is the pump status flag. Experiment Mode is set to 4 (for Sync2 call). ALGO 510 is called again, n=m+2. Finally, a call is made to ALGO 510 as a Sync2 call. For Sync2, the Pumpdat vector is updated as shown by FIG. 35. The sequence is then repeated for the next control cycle.

ALGO—APS Flow

An example of ALGO—APS process flow is also provided hereafter in Table 14. It is to be noted that lapse time is the relative time t in minutes since the start of the experiment. When a restart occurs, the start time is the start time of the experiment and not the start time of the restart. Lapse time is still the relative measured with reference to "ExperimentStruc.t_zero".

TABLE 14

ALGO - APS flow

| Stage | | | |
|---|---|---|---|
| 1 | Startup | Lapse time t is >=0<br>"ExperimentStruc.t_zero" assign absolute time for t<br>xk is empty<br>u filled with latest information. If no information send NaN (or zero)<br>Event Struc (whatever events are triggered)<br>PumpStruc filled with latest data)<br>BGStruc filled with latest data<br>PatientIniStruc<br>ExperimentStruc contains PatientIniStruc<br>Lapse time t is >=0 and is the time in minutes from "ExperimentStruc.t_zero" | |
| 2 | Re-Start | "ExperimentStruc.t_zero" assigns absolute time for t is the time already stored in 1.<br>xk is whatever the last xk is<br>u filled with latest information. If no information send NaN (or zero)<br>Event Struc (whatever events are triggered)<br>PumpStruc (filled with latest data)<br>BGStruc (filled with latest data)<br>PatientIniStruc<br>ExperimentStruc contains PatientIniStruc | |
| | | BGStruc.bg1timestamp | At top of ALGO Call |
| | | BGStruc.bg1data<br>Data acquired from Database and will reflect all the sensor data collected up to time t | At top of ALGO Call |
| | | BGStruc.online1 will reflect the online status | At top of ALGO Call |
| 3a | Sync1 | BGStruc.available1 will reflect the current status | At top of ALGO Call |
| | | u(7) cumulative amount | At top of ALGO Call |
| | | u(8) time of cumulative amount<br>Just before Sync1 call APS acquires from DB and enters the cumulative amount dispensed with the timestamp | At top of ALGO Call |
| | | PumpStruc.online1 will reflect the online status | At top of ALGO Call |
| | | PumpStruc.available1 will reflect the current status | At top of ALGO Call |
| | | ExperimentStruc.mode = 3 | At top of ALGO Call |
| | | yAMT(1) = total insulin which is u(7) | At end of ALGO call |
| | | yAMT(2) ignore | At end of ALGO call |
| 3b | Sync1 | yAMT(3) ignore | At end of ALGO call |
| | | yAMT(4) = recommended value from algo | At end of ALGO call |
| | | yAMT(5) = amount delivered last cycle | At end of ALGO call |
| | | yAdvice $1^{st}$ two characters represent code | At end of ALGO call |
| | | yTrace string of characters | At end of ALGO call |
| | | Append the array with following new information<br>PumpStruc fields:<br>total_insulin = yAMT(1)<br>amt1recco = yAMT(4)<br>amt1delivered = yAMT(5)<br>amt1deliveredtimestamp = u(8) | BY APS |
| | | yAdvice APS will analyze and appropriate action like pop up message. YAdvice will be displayed in log window.<br>yTrace is sent to log file | BY APS |

TABLE 14-continued

ALGO - APS flow

| Stage | | | |
|---|---|---|---|
| 3c | Sync1 | Recommended value yAMT(4) will be displayed to user through Recommendation window | BY APS |
| | | User acceptance is stored in:<br>fluid1cmdindx set to:<br>0 if not accepted<br>1 if accepted<br>2 if override<br>fluid1cmdtimestamp = t (when the recco-confirm window is completed)<br>u(7) = Decided amount from recco-confirm window. | BY APS |
| | | ExperimentStruc.mode = 4<br>BGStruc.bg1timestamp<br>BGStruc.bg1data<br>NO CHANGE NO UPDATE, IGNORE | BY APS |
| | | BGStruc.online1 will reflect the online status<br>ignore | At top of ALGO Call |
| 4a | Sync2 | BGStruc.available1 will reflect the current status<br>ignore | At top of ALGO Call |
| | | Append the array with following new information<br>PumpStruc fields:<br>total_insulin = yAMT(1) Done by APS<br>amt1recco = yAMT(4) Done by APS<br>amt1delivered = yAMT(5) Done by APS<br>amt1deliveredtimestamp = u(8) Done by APS<br>fluid1cmdindx Done by APS<br>fluid1cmdtimestamp = t (when the recco-confirm window is completed) Done by APS<br>u(7) = Decided amount from recco-confirm window. Done by APS | At top of ALGO Call (Repeating the assignments for clarity) |
| | | PumpStruc.online1 will reflect the online status (ignore) | At top of ALGO Call |
| | | PumpStruc.available1 will reflect the current status (ignore) | At top of ALGO Call |
| | | ExperimentStruc.mode = 4 | At top of ALGO Call |
| | | yAMT(1) ignore | At end of ALGO call |
| | | yAMT(2) = commanded rate | At end of ALGO call |
| 4b | Sync2 | yAMT(3) = commanded type | At end of ALGO call |
| | | yAMT(4) = decided amount | At end of ALGO call |
| | | yAMT(5) ignore | At end of ALGO call |
| | | yAdvice 1$^{st}$ two characters represent code | At end of ALGO call |
| | | yTrace string of characters | At end of ALGO call |
| | | APS will analyze yAdvice and appropriate action like pop up message is done.<br>lyAdvice will be displayed in log window.<br>yTrace is sent to log file | BY APS |
| | | Assignments to PumpStruc fields:<br>fluid1cmdrate = yAMT(2)<br>fluid1cmdtype = yAMT(3)<br>amt1decided = yAMT(4) | BY APS |
| 4c | Sync2 | | |

Aspects of interest are that Sync1 follows Sync2 provided Sync2 happens before edge of ControlCyle, and restart yAMT is recorded and stored correctly by APS. It is to be noted that restart is the resumption of an unfinished experiment with the previous data collected for APTS to graph and for ALGO to use. Sensor and Pump data are assigned to BGStruc and PumStruc using Lapse time in minutes. Vector u always sends the very last available data along with time stamp. If no new data is acquired, then the last known data acquired. A discussion on the second specification implementation embodiment is now provided.

APCATS (Automated Pancreas—Control Algorithm Test Suite)

The Automated Pancreas—Control Algorithm Test Suite (APCATS) is a software program that serves as a standardized simulation tool, an AP Test-Stand emulator, a verification tool, and as an evaluation tool. As a standardized simulation tool, APCATS provides the basic functionality needed to simulate a generic closed-loop system. As such, this functionality allows someone designing mathematical models to focus on the modeling itself rather than on details of connections and verification of the basic setup and connections. As an AP Test-Stand Emulator the program can shorten the time required to evaluate and verify algorithm changes from what would be required by the APTS 500. To achieve this, it uses "simulated" time (as opposed to real-time) while providing the same simulated environment for the ALGO 510. Also, by allowing simulation over range of parametric values, APCATS can broaden the scope of an evaluation without endangering the patient. In addition, APCATS can be used to simulate and evaluate critical scenarios. For example, device failures can be systematically evaluated or failsafe modes can be implemented and assessed.

As a verification tool, APCATS provides the capability to emulate an APTS 500 thereby allows any revisions to the ALGO 510 to be first verified under development and pre-release scenarios. As an evaluation tool, APCATS can be used to simulate mathematical models, controllers, closed-loop responses, etc., thus allowing the (1) quality and (2) performance of the simulated item to be evaluated. In the illustrated embodiment, APCATS was developed and runs in the MAT-LAB technical computing environment. In other embodiments, other languages and computing environments such as visual basic and Windows operating system may be used. The front-end user interface provides a quick means of developing and analyzing control laws for the somewhat standardized Automated-Pancreas System. It provides a common platform for performing analysis and simulation as well as driving a real system, if hardware is connected in the control loop. As APCATS is implemented in a similar operating environment as APTS 500, such as in system 10, and implementation of a software program on hardware is well understood by those skilled in the art, the sections hereafter only focus on the software components of this second specification implementation embodiment of the present invention.

Software Components

The APCATS application comprises several distinct software components which are divided into three categories: user interfaces; initialization files; and component modules. APCATS has a central core that holds the data and forms the backbone that brings all the front ends into a unified application. The initialization files, also referred as init files, inform the APCATS core where needed modules are and what modules it needs to read and implement. Based on the information in these files, APCATS dynamically creates itself. Component modules mathematically describe how each of the components behaves. During simulation, they dynamically react to external and internal excitations. The component modules are categorized herein under the following major types: plant; actuator; sensor; controller; and external disturbance. Each of these component modules are discussed in greater details in later sections.

The user interface (UI) is the front end that allows input from the user such as: selection of options, interaction with certain features, and entry or modification of values. It also allows the user to observe the outputs. Because the core is designed to be independent of the problem itself, the problem definition sits in component modules. The flexibility of the interaction between the UI and the component modules is managed through the initialization files. The user interface covers the following core aspects: APCATS main window; user entry forms for each component; menu forms for components; simulation run setup form; generation of simulation link (Simulink) block diagrams; managing and interacting with data files; plots to display results; storage and retrieval of APCATS setup; and connection interface.

Figure 22:
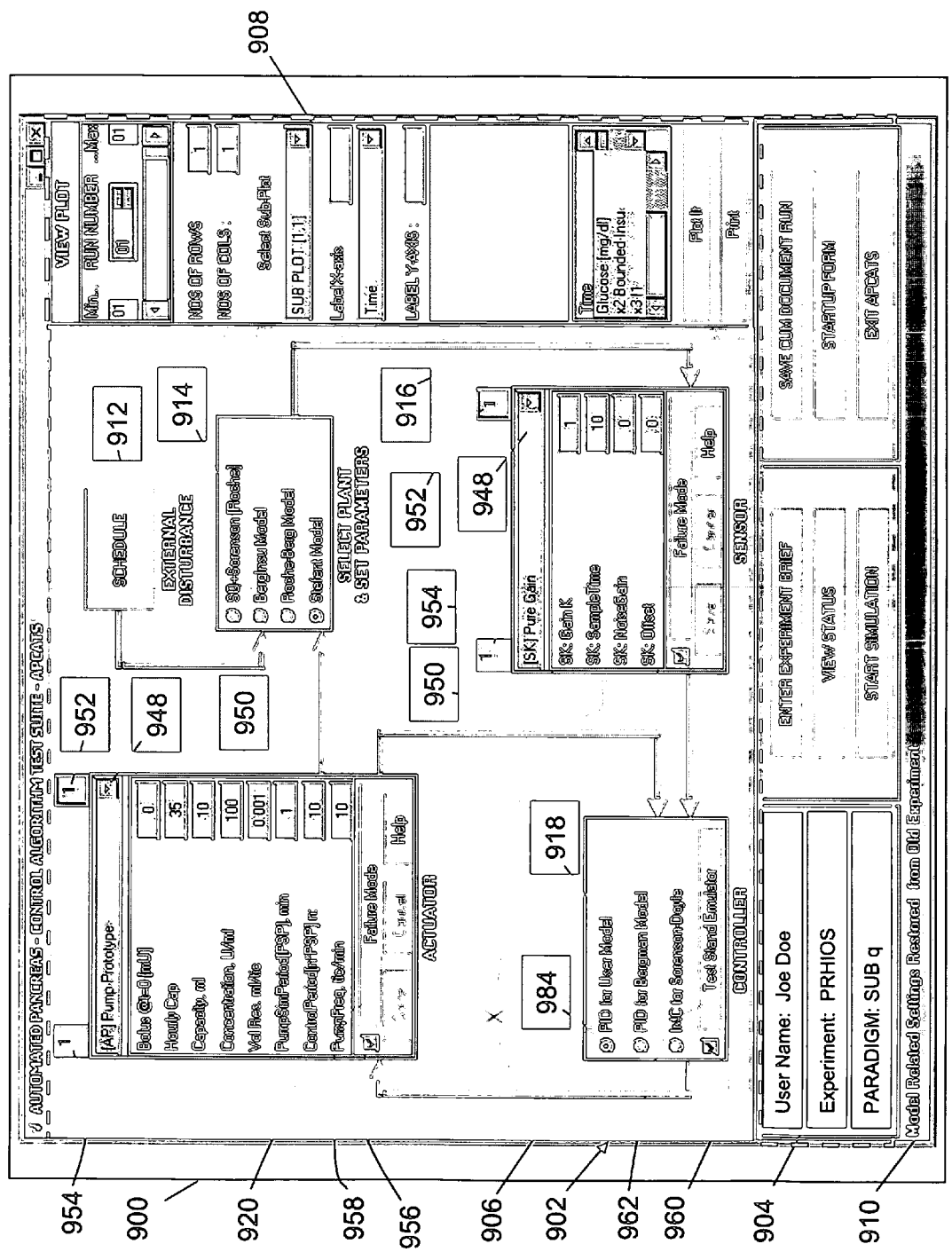
FIG. 22 is a depiction of a graphical user interface for an Automated-Pancreas Control Algorithm Test Suite (AP- CATS) software according to the present invention and implement on the system of FIG. 2 for developing patient-specific therapies.

With reference to FIG. 22, APCATS, generally indicated by symbol 900 provides a user interface as a main window 902. The main window 902 provides three panes: a run/store pane 904; algorithm pane 906; and plot pane 908. In addition, a status bar 910 at the bottom relays messages of APCATS 900 activity.

The algorithm pane 906 is a control algorithm that is central to regulating blood-glucose level within a model patient. The algorithm pane 906 displays the automated-pancreas control algorithm, which consists of several blocks connected with input/output connection lines X. The algorithm pane 906 is used to set up the overall closed-loop system. It allows models to be selected, parameter values to be edited, and connections to be modified. Each of the blocks and connections may be selected to display and set their parameters. The available blocks are: external disturbance block 912; plant block 914; sensor block 916; controller block 918; and actuator block 920. As shown, the block connections are: external disturbance block/plant block connection; plant block/sensor block connection; sensor block/controller block connection; controller block/actuator block connection; actuator block/plant block connection; and actuator block/controller block connection.

Figure 23:
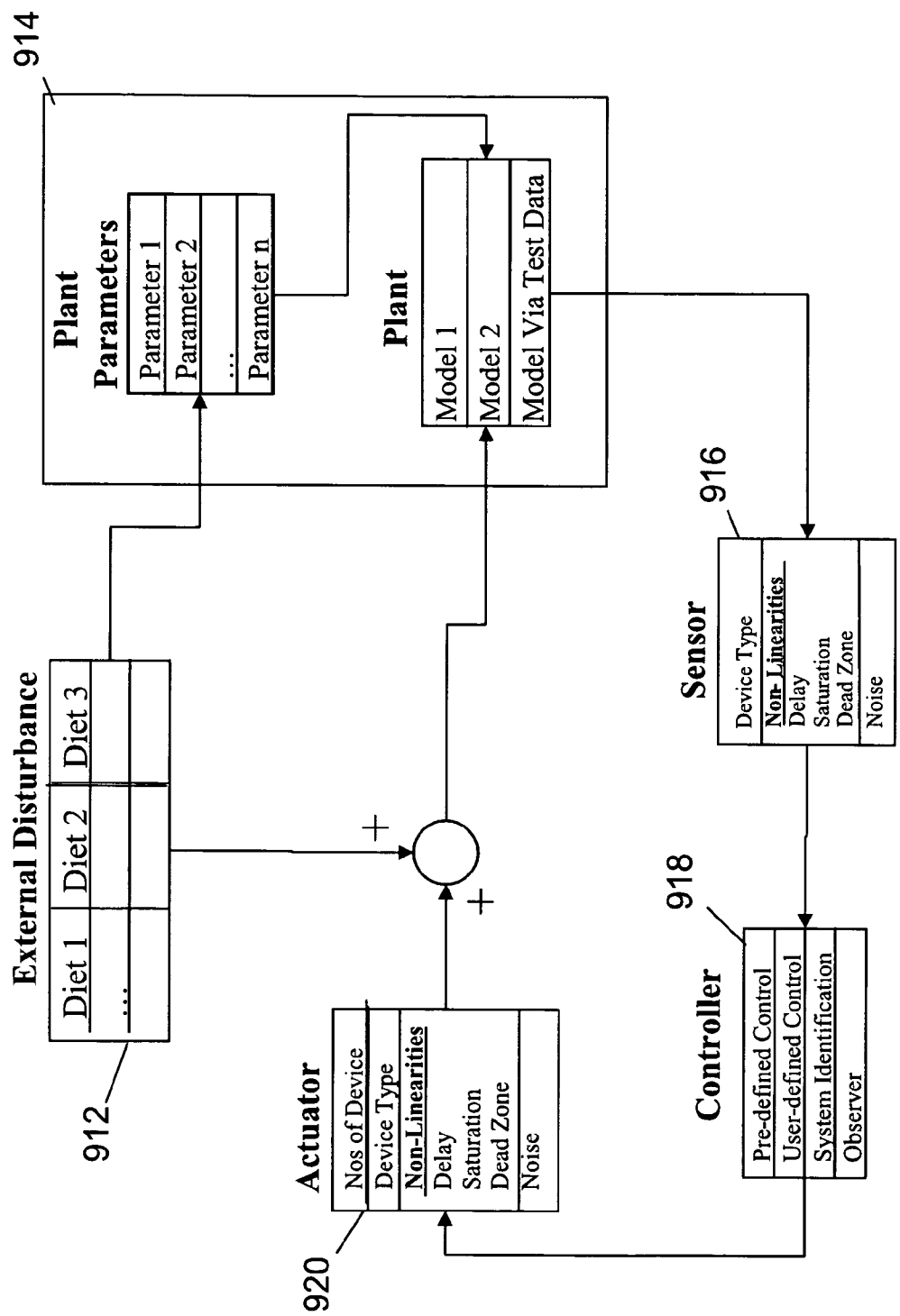
FIG. 23 is a block diagram showing connections between module blocks of the APCATS software, and the flow of information between the blocks; according to the present invention.

FIG. 23 is a block diagram showing the generic closed-loop structure in which the interconnecting arrows in the diagram represent the interfaces between the blocks of the algorithm pane 906. The interconnecting arrows also represent the flow of information between the blocks. Each of the blocks of the algorithm pane 906 provides, at the topmost layer, several options to the user. Further options, if any, associated with a selection are laid out as hidden sub-layers. These layers open up to the user and are activated as the user proceeds from the topmost visible layer to lower ones. Through the various blocks 912-920 and connections on the algorithm pane 906, it is possible to modify the parameters needed for simulation. They allow the user to select from several possible models; set the parameters corresponding to the selected models; and set the information passed through the input/output connections. The various blocks of the algorithm pane 906 are described in more detail hereafter, with reference made first to the plant block.

Plant Block

The plant block 914 provides list a number of selectable patient models (e.g., patient models 73 in FIG. 3) which reflects the current knowledge of relevant physiology and metabolic interactions. New patient models with varying degrees of complexity and detail can be modeled and provided (added) for use in plant block 914. By adjusting the parameter bounds, the plant block 914 can be used to study and model a wide range of behaviors. The plant block 914 receives input from actuators and disturbances created by various dietary intakes. The sensors are used to measure the outputs from the patient model selected in the plant block 914.

Plant Selection and Parameter Setting

Figure 24:
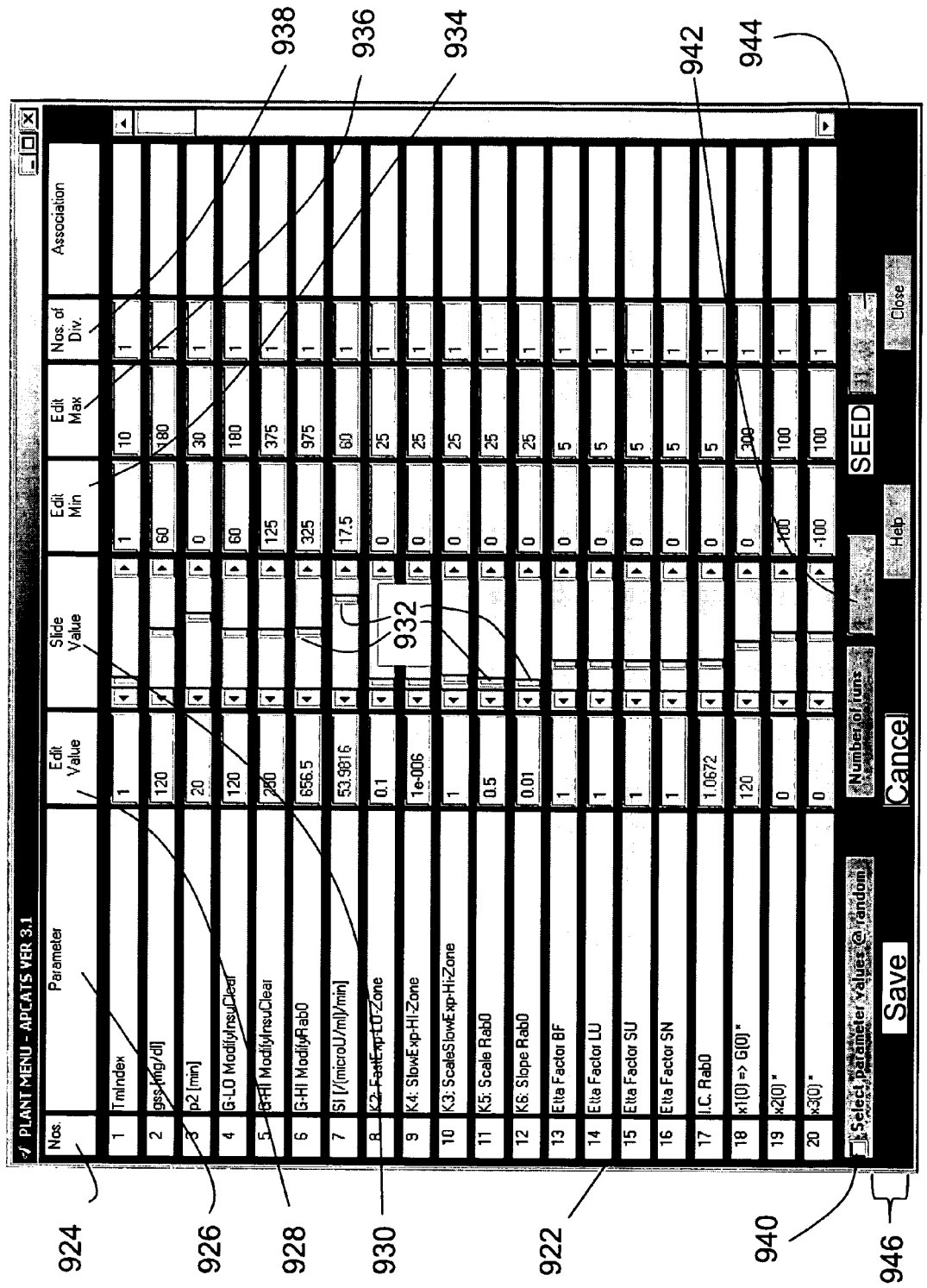
FIG. 24 is a depiction of a graphical user interface providing a plant menu window used to change patient model parameters for a simulation environment according to the present invention.

The patient model is selected through the plant block 914 by clicking on one of the corresponding radio button. Only one patient model can be selected at any time. The corresponding radio button becomes highlighted and a plant menu window 922 is brought up as shown by FIG. 24. Clicking on an already selected patient model will also bring up the plant menu window 922. If the plant menu window 922 is already open when a new plant is selected, APCATS 900 will check to see if the parameters entered into it have been saved. If they have, the current plant menu window 922 will be closed and a new plant menu window for the newly selected model is opened. If the parameters have not been saved, a message to that effect will be displayed in the message bar at the bottom of the main window 902 and the already active plant menu window 922 will not be closed. Parameters corresponding to the selected patient model are displayed in the window and loaded with saved values stored in memory. The parameter values can be edited and will be displayed in the following colors indicating their editing state: black—default or unedited value; red—edited value; blue—frozen, non-editable value.

If the patient model selection is changed, previously existing connections between the blocks linked with the plant block 914 will be broken and the user will need to reconnect them. (See the Connections section provided below.) The inputs and outputs associated with the plant block 914 are updated. Also, selecting a new patient model will result in an updated lists of independent and dependent variables in the plot setup. (See Section 6.) Each parameter in the plant menu window 922 is listed in its own row. The columns in the plant menu window 922 are: a "Nos." column 924 for each row, a "Parameter" column 926 for parameter names, and an "Edit Value" column 928 for entering in a parameter value. The entered value must be between the specified minimum and maximum values for the parameter in the two columns provided after a "Slide Value" column 930, were changes to the value will also be reflected in the adjacent slider 932.

The "Slide Value" column 930 provides an alternative method of setting the parameter's value, with the left and right ends of the slider 932 corresponding respectively to the minimum and maximum values for the parameter. When the slider 932 is moved, the numeric value of the parameter will be updated in the column to the left of the slider in the Edit Value column. An "Edit Min." column 934 provides the minimum allowable parameter value. This value may be edited, where changes will also be reflected on the slider 932. An "Edit Max" column 936 provides the upper limit on the parameter value. A large value should be used for parameters that do not have an upper limit. This value may be edited, where changes will also be reflected on the slider 932.

The "No. of Div" column 938 is used to indicate the number of values of the parameter over which simulations (e.g., parametric studies) are performed. A non-zero positive integer must be entered. Non-integer values are rounded to the nearest valid integer. For the following values of Div, the parameter values that will be used in the experimental simulation are: 0 or 1 means use the entered parameter value; 2 means use the minimum and maximum values; 3 means use the minimum, average, and maximum values; n (where n is a positive integer) means use the minimum, maximum, and n-2 equally spaced intermediate values. Note, parametric studies will include every combination of parameter values and may lead to an excessive number of runs if multiple values of several parameters are used. To determine the number of combinations, multiply the numbers of divisions selected for all parameters. With APCATS 900, two different types of parametric studies can be performed: (a) systematic spanning of parameter range; and (b) random spanning of parameter range.

(a) Parametric Studies (Systematic)

To perform a parametric study on a given parameter, the user sets the number of divisions for the parameter to the number of values to be studied. The values of a parameter for which runs will be made will be the entered minimum and maximum and a number of evenly spaced intermediate values sufficient to give the stated number of values. For example, if the number of divisions for a parameter is set to 5, runs will be made for the minimum and maximum values and three other values, at ¼, ½, and ¾ of the distance between the minimum and maximum. If more than one parameter is set to use multiple values, a run will be made for each possible combination of the values of all parameters. Caution should be taken in setting "Nos. of Div.", as it can easily create an excessive number of combinations/runs.

(b) Parametric Studies (Random)

To use random parameter selection, the user checks the "Select parameter value @ random" checkbox 940. The "Number of runs" and "SEED" fields 942 and 944, respectively, will become enabled. In the "Number of runs" field 942, the user enters the number of simulations to be run during the simulation of the experiment. In the "SEED" field 944, the user enters a positive integer as the seed for the random number generator. The SEED value is used to recreating the random number sequence and is stored in the experiment's documentation to allow the random values to be regenerated. The random number generation assumes a uniform distribution over the parameter range. For each run, the random values used for the parameters are stored in the documentation file. A command line menu 946 at the bottom of the plant menu window 922 provides the following functionality: save, cancel, help, and close. "Save" saves any parameter changes and is active only if at least one value has changed since the last time they were saved. "Cancel" restores the last saved values. This button is active only if at least one value has changed since the last time they were saved. "Help" opens up a help window, and "Close" saves changes, if any, and closes the window 922.

Sensors and Actuators

Because the formulations of the sensor and actuator blocks 916 and 920, respectively, are similar, as are their user interfaces in the algorithm pane 906, they are herein discussed together and collectively referred to as device blocks. The actuator block 920 (FIG. 22) simulates a pump unit that receives commands from the controller block 918. This activates the actuator block 920. The output(s) from the actuator block 920 are sent to the plant block 914. The sensor block 916, on the other hand, measures signals from the patient model selected in the plant block 915 and sends information to the controller block 918. The device blocks 916 and 920 have following characteristics: device dynamics which is described by mathematical relations, device parameters, input(s); and output(s). Each of the sensor and actuator blocks 916 and 920 provides the following setup selections: number of devices; type of device/device model; and device coefficients. Note, as noise and nonlinearity are built into the functions, their parameters can be listed along with other device coefficients.

Devices are selected from a pull down list 948 in the device blocks 916 and 920 in the algorithm pane 906. On selection of the device, the parameters specific to the device, also referred to as coefficients 950, are listed in the respective device block. Default values are normally listed next to the coefficient description. The coefficient values are editable. If any of the values are edited, the Save and Cancel buttons become enabled. To revert to the last saved values, click the Cancel button. To save the entered values, click the Save button. Either of these actions disables the buttons until the next edit is made. Note, new simulations will not be executed if the Save and Cancel buttons are active, i.e., if there are any unsaved coefficients in the respective device block. APCATS 900' ability to allow several device units to run in parallel allows multiple sensors or pumps to be simulated simultaneously.

To implement multiple simultaneous units, the user has to enter the desired number of units in the top-right number tab 952 on the device menu, which indicates how many control channels are in operation. Each unit will have its own device form, selectable by a numbered tab 954 on the top-left side. The numbered tab 954 of the currently selected device will be highlighted. The user can edit the coefficients 950 on each of these forms. An increase in the number of devices will add new devices to the end of the drop down list 948. Likewise, a decrease will remove devices from the end of the list 948 (i.e., the higher numbered devices). If the user decides to switch to another tab before saving the form, he will be prompted to save the form and must save or cancel the modifications before proceeding. The user can change the number of tabs and devices at any time. If he enters a number that exceeds a predefined maximum number of devices, the number will revert to the prior value. Any time a device is altered, the previously existing input and output connections for that device are broken. Prior to running a simulation, the user must make new connections between the device and the modules supplying its input and accepting its output. Similarly, connections must be made for any newly added device as well. Note the ability to switch a device without checking if parameters need to be saved or discarded has not yet been completed. Currently, APCATS 900 discards any changes made since the last save.

Device blocks 916 and 920 can operate in two modes: (1) non-failure mode, which is normal uninterrupted device operation, and (2) failure mode. Failure mode allows the simulation of device interruption, i.e., the freezing of device output to the broken state while the other sub-blocks continue normal operation. At the end of failure, the device comes back on by reinitializing itself. Failures can be scheduled by specifying which device has failed, the type of failure it experienced, and the duration of the failure. To enable the failsafe/failure mode and allow failures to be scheduled, the user checks a checkbox 956 to the left of a Failure Mode button 958. If a checkbox 960 for a Test-Stand Emulator (APSe) button 962 on the controller block 918 has been checked, the Failure Mode checkbox 956 is automatically checked and disabled so that it cannot be altered. If the checkbox 960 for the Test-Stand Emulator button 962, which is an emulated (simulated) APS, is not checked on the controller block 918, the user may use the failure mode checkbox 956 to select failsafe/failure mode. If failure mode is enabled, additional output indicating the failure type is created. By default, a value of 0 (zero) indicates normal device operation.

Figure 25:
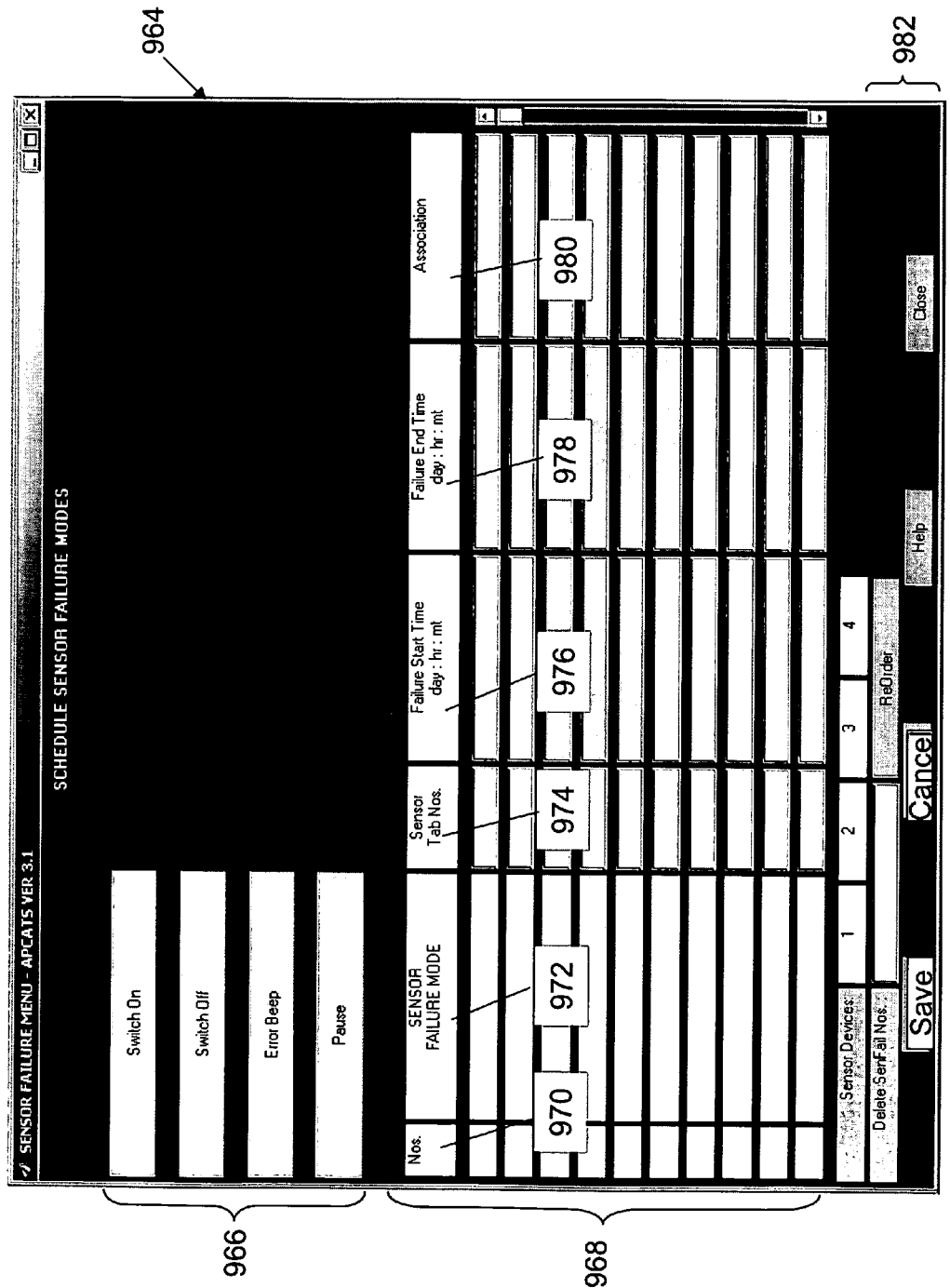
FIG. 25 is a depiction of a graphical user interface providing a failure menu window for a simulation environment according to the present invention.

To schedule failures, the user clicks the failure mode button 958 (if failure mode has been enabled) on the respective device block 916 or 920. A respective device failure menu 964 window will open which in FIG. 25 is a sensor failure menu window. As the actuator failure menu window is similar, only failure menu window 964 is discussed. The failure menu windows 964 contain buttons 966 for different predefined failures. Click on these buttons 966 to enter the failures into a failure schedule 968. The schedule lists various parameters for the selected failure modes, some of which are editable. The parameters are: "Nos." 970, "Failure Mode" 972, "Tab Nos." 974, "Failure Start Time" 976, "Failure End Time" 978, and "Association" 980. The "Nos." parameter 970 is the serial number of the failure entry. The "Failure Mode" parameter 972 is the name of the failure, and the "Tab Nos." parameter 974 is the tab number of the device to which to assign the failure. The device must exist for the failure to take effect). The "Failure Start Time" parameter 976 is the start time in days, hours, and minutes. Any non-numeric character may be used to separate the numbers. If only a single number is entered, it is assumed to represent minutes. If two numbers are entered, they are assumed to represent hours and minutes. The "Failure End Time" parameter 978 is the end time in days, hours, and minutes. The interpretation of the entered numbers follows the same pattern used for start time.

The "Association" parameter 980 is used to capture comments. The failure number and name are entered when a failure button is clicked. These fields are not editable. If no start time is entered, the failure is never initiated. If the entered start time proceeds the end time, the failure begins at the start time and cuts off at the end time. If the start time is greater than or equal to the end time, the failure begins at the start time and stays on until the end of the simulation time. The failure menu window 964 also has command line buttons 982 at the bottom, which are: "Reorder" which reorders the failures in order of ascending start time; "Save" which retains any changed values; "Cancel" which restores the last saved values; "Help" which opens a help window; and "Close" which saves any changes and closes the window. The Save and Cancel buttons are enabled only if any of the information on the schedule has been altered since it was last saved. The remaining items shown on the failure menu window 964 are self explanatory.

Controller

The Controller block 918 is similar to the Plant block 914. It lists all available controllers as radio button selections allowing only one to be selected at a time. To select a controller model, click on a model's radio button 984. It is to be noted that the automatic care that will stabilize the patient to the varying influences of external excitations is controlled and corrected by the controller module. This is done by correctly administering the medication in a continuous fashion. Although the APCATS 900 provides a listing of standard control algorithms to be tried out, it also has an option to introduce a user-defined controller. The basic idea is to provide a plug-in-and-run-the-controller type situation. The options may look as follows: Controller 1 (Modify Parameters); and Controller 2 (Modify Parameters) . . . ; and Controller n (Modify Parameters). After selecting a controller model, a controller parameter window will appear. As the controller parameter window is similar to the plant menu 922 (FIG. 24), the controller parameter window is not shown and no further discussion on how to adjust listed controller parameters is provided. Any time the controller is altered, the previously existing input and output connections are broken. Prior to running a simulation, the user must create new connections between the controller and the modules supplying its input and accepting its output.

Test-Stand Emulator

Checking the checkbox 960 in the controller block 918 (FIG. 22) enables the test-stand emulator pushbutton 962, which when clicked brings up a Test-Stand Emulator window 986, such as shown by FIG. 26. The Test-Stand Emulator window 986 is used to link disturbances to event types. The Test-Stand Emulator window 986 at the top half contains Event type buttons 990, grouped in four columns. The buttons 990 in a given column relate to the same specific aspect of an event and represent the event functions that can be triggered. Each button 990 is associated with a disturbance defined through the disturbance module. Clicking on one of these buttons 990 enters the corresponding event, called a triggered event, into an event schedule 992 located in the lower section of the window. The event schedule 992 is the timetable of when events (disturbances) are scheduled to occur, their durations and magnitudes. To associate a disturbance with an event in the schedule, the user first left clicks on the disturbance to select it. The row will become highlighted in yellow. Next, click on associated one of the buttons 990 for the event type to be entered in that row. The user then proceeds to enter the remaining values in that row.

When triggered, the triggered event is merely acted on the selected patient model checked in the plant block 914 (FIG. 22). The controller block 918 is made aware of a disturbance by associating with it an appropriate triggered event. A triggered event listed under the "Event List" column has several properties: trigger time, shown as "Event Start Time"; "Event type"; relative trigger time, shown as "ALGO Action Time"; duration of the event, shown as "Action Span Time"; and "Amount." The Event Type is an event code used by the algorithm. It can be entered by either clicking one of the Event Type buttons or entering the corresponding code (given in parentheses on the button). The relative trigger time is with respect to the time of the physically occurring event in which the controller block 918 (i.e., ALGO 500) becomes aware of the triggered event. The controller block 918 can be told of the occurrence: (a) before the actual event occurs (negative number); (b) simultaneously with the occurrence of the event; (c) some time after the actual event (positive number). The duration of the event is used to select the duration an event stays active after being triggered. The event amount is used to select the magnitude of the event.

The bottom of the Test-Stand Emulator window 986 contains command menu buttons 994. The buttons 994 and their functions are as follows. "Patient Ini" displays the path and name of the initialization file PatientIni. The PatientInin file contains patient parameters that are used by the controller (e.g., APS 500). "Experiment Directory" displays the location of the directory where data will reside, and "Save" saves and updates values to the current changes. "Cancel" rejects changes and reloads the last saved values, and "Help" display a help screen. "Close" saves any updated values and close the window. If desired, a refresh button may also be provided.

External Disturbances

The external disturbances block 912 (FIG. 22) provides a means to simulate responses to carbohydrate consumption, physical activity, and other activities expected from a person leading normal and healthy life. For a diabetic patient to be able to lead a normal life, his or her bodily functions must adjust to cope with such disturbances/excitations. The robustness, effectiveness, and stability of the closed-loop system are evaluated by investigating (1) changes in model parameter values over the operating range and (2) all possible scenarios of external disturbances/excitations. Clicking on the external disturbances block 912 on the APCATS main window 902 displays an External-Disturbance menu window 996 such as shown by FIG. 27. A set of excitation function buttons 998 that are predefined is provided under the title designated "SELECT DIET CUM EXERCISE OPTIONS" as shown by FIG. 27. Additional excitation functions are easily introduced into the list by writing new functions as described in a later section and modifying an initialization file DietInit. Options are available for testing various scenarios, a standard set of test-cases, or an arbitrary user case. These are built by using the disturbance functions and scheduling their occurrences.

The buttons 998 may be enabled or disabled, as the disturbances available for selection depend on the patient (plant) model selected. Thus, for a given patient model, only the disturbances defined for that patient model are enabled and available for selection. Disturbances may be entered in any order. The External-Disturbance menu window 996 also provided an external-disturbance schedule 1000 to set up for the length of the simulation. The external-disturbance schedule 1000 lists the following in column form: number of the disturbance; name of the disturbance; scale strength; start time; end time; and association. The number and name of the disturbance are not editable, but are set when the disturbance-selection buttons are used to enter the disturbances into the table. The scale strength value allows the user to scale the output value by a factor. The default scale value of 1 indicates nominal disturbance. As the remaining columns of the schedule 1000 are similar to the schedule of the Test-Stand Emulator window 986 (FIG. 26) in their use to schedule disturbances (excitations) to occur during the period of the simulation, no further discussion thereon is thus provided. In addition, as command menu buttons 1002 at the bottom of the External-Disturbance menu window 996, is also similar to those buttons provided on the failure menu 952, not further discussion is also provided.

Interlinking Disturbance Outputs with Plant Parameters

An external excitation, in general, drives the plant parameters as well as the input to the plant. In this particular case, each of the disturbance functions is considered to be a module with outputs consisting of (1) the outputs that need to be connected to the plant block 914 and (2) disturbance parameters that are in one-to-one correspondence with the plant parameters. The disturbance output(s) plus parameter outputs from disturbance are passed on to become the input and parameters of the plant model. However, there is an important consideration when multiple disturbances occur simultaneously. The effects of multiple disturbance functions are superimposed by summing the outputs from all of the disturbances to form a single vectored output, which becomes the input to the plant block 914. To be able to do this requires that, among the disturbance models, each of the disturbance outputs conforms to the other disturbance outputs in the number of outputs and their order. However, from the disturbance block 912 perspective there is no restriction on the number of outputs or their order. On the other hand, parameter-outputs have to agree in order as well as number with the selected plant. When multiple disturbances act simultaneously, unlike the outputs described above, the parameters are not added but rather the parameter set from each of the disturbances is resolved and a single set of parameter values is determined. The function managing this scenario is a filter function.

After entering an external disturbance in the External-Disturbance menu window 996, the filter function gets the number of parameters from the selected patient model. The operating statuses of all diets (operating=1; non-operating=0) are multiplexed with the parameter values coming from the diets. The number of diets is computed by using following logic: Number of diets=length of input vector/(1+length of parameters). The entered start and end times of the external disturbance become the times at which the function is activated and at which it stops. The mathematical function describing the diet is independent of start time. In regard to end time, the function may have a set time course and, in such a situation, there are a couple of ways to treat end time. The function, in general, is a differential equation, with all of its initial conditions and parameters being described within the function. The function behavior is the normalized response. The output is scaled by the entered scale value provided in the event schedule 1000 under the "Scale Strength" column. Although a positive scale value is normally expected, a negative value may be entered to simulate a negative effect.

Connect Ports Form

Clicking on a connection line shown in the APCATS main window 902 brings up a connect ports form 1004 which is shown by FIG. 28. On its left side, the Connect Ports form 1004 lists and numbers the available outputs 1006. The outputs 1006 are generated by the block sending the information. The right side displays the inputs 1008 of the block receiving the information, along with empty edit boxes. To create a connection between a specific output 1006 and a specific input 1008, the user types the number corresponding to the output into the edit box adjacent to the input field that is to receive the output. Any input 1008 that is not connected to an output 1006, i.e., has a blank edit box, is set to zero. Also note that an input 1008 cannot be connected to more than one output 1006. It is not necessary for every output to be connected to an input. The simulation will generate data for all listed outputs, but those left unconnected will simply not be used as input to the next module. Outputs can be connected to more than one input. On completing all desired connections, click the "X" (Close Window) button in the upper right-hand corner to save the connections and close the form.

Run/Store Pane

The Run/Store pane 904 of the APCATS main window 902, which is enlarged by FIG. 29, provides the basic functionality for loading data, saving data, and running simulations. In addition, it displays experimental settings, allows the user to enter an experimental brief, and, lastly, allows the user to exit from APCATS 900. The leftmost column of the Run/Store pane 904 displays entries made and modified in a Startup Entry form 1010 (FIG. 32). The three pieces of information it displays, from top to bottom, are: user name; the experiment group and experiment identification number; and the paradigm in use (intravenous-intravenous, subcutaneous-subcutaneous, intravenous-subcutaneous). To enter details and comments about the experiment, click an Enter Experiment Brief button 1012. Doing so will bring up the "APCATS 900—Add Particulars about the Current Experiment" window (not shown). The information entered in this window is stored in the experiment's documentation (doc) file. This information can be updated any number of times.

To compile the current APCATS 900 settings and save them, the users clicks on a View Status button 1014. On doing so, the status information is written to a temporary location (work area) and displayed in an editor. To save the current settings of the input variables to a file, the user clicks on a Save Cum Document Run button 1016. The setup documentation displayed when the View Status button 1014 is clicked is also saved. The current initialization settings needed to recreate the experiment are written to a temporary file in the work area. Should APCATS 900 fail, then the settings saved in this file can be restored by clicking on an Old button 1015 on the Startup Entry form (FIG. 32), and searching for the temporary filing in the listed file directory. To bring up the Startup Entry form 1010 at any time, click on the STARTUP FORM button 1018. The Startup Entry form 1010 (FIG. 32) is used to edit the details needed to define the scope of the experiment and maintain proper records. To exit APCATS 900, click the "EXIT APCATS" button 120. The "Exit from APCATS" dialog box comes up (not shown) which allows the user to return to APCATS 900 and cancel the exit command. Clicking the Continue button will proceed with closing the application. It will close all APCATS-generated windows before closing the main APCATS window 900.

To start a simulation, the user clicks on a Start Simulation button 1022. Doing so will bring up the Simulation Parameters window 1024 shown by FIG. 30. The Simulation Parameters window 1024 allows the user to set the start and stop times for a simulation, select an integration routine and step size, and run the simulation. A majority of the field are self explanatory. By default, simulation runs start at time 0. Entering a non-zero value provides an offset to the start time. To set the end time for the runs of the simulation, the user enters a value in a Stop Time textbox. The stop time must be greater than the start time for a simulation to execute. To set the integration routine to be used in the simulation, the user selects it from a solver dropdown menu 1026. To set the integration step size, the user selects it from a step size dropdown menu 1028. For time Period for save data, the user enters the period between data saves. Relative tolerance is an integration convergence criterion. Absolute Tolerance is also an integration convergence criterion. The user selects a value from a dropdown box 1030 to set the time window to be displayed during simulation. Available selections are hourly, quarter day, half day or daily, and the entire simulation. For Simulink Model File Name, a flag defined in the init file controls whether or not a user can rename a simulation-model file. If authorized, the user may enter the name of a Simulink file in the Simulink Model Name edit box. For Build Model Only, a flag defined in the init file controls whether or not a user can build and view a model. If authorized, the user may click the Build Model button 1032 to build the Simulink model for which a file name was entered into the Simulink Model Name text box. The user may then look at the model by opening the a model (mdl) file.

Simulation Run

To begin the simulation, the user clicks on a Start button 1034. Clicking this button will trigger the following actions: documentation and initialization files are created and saved; the parametric study loop is set; a Simulink block diagram is created and simulated, and the resulting data is saved. For systematic (S) or exploratory (E) experiments, an experiment identification number is generated and the appropriately named data files are saved to a system directory. If there a problem in saving the files here, they are instead moved to a parked data directory, normally located on the user's local hard drive. For experiments in the play (P) group, the user is asked to supply an experiment identification number. For systematic (S) or exploratory (E) experiments, logging information is added to log files maintained on a network drive. Clicking on a continue button 1036 will continue a simulation from an already finished state, extending the simulation. Clicking on a pause/resume button 1038 will either pause a running simulation or resume a paused simulation. To stop the simulation in progress, the user clicks on a Stop button 1040. If a simulation is stopped by the user, no data from the partial simulation will be saved. This prevents the creation of incomplete data sets. The Simulation Clock displays the simulation-clock time. This allows the user to monitor the progress of a simulation. The Current/Total Run Nos. displays, in hexadecimal notation, the current run number and the total runs of the experiment.

After a simulation run, APCATS 900 will generate output. The following options are available to the user: generate performance measures; decide, before simulation, what outputs are to be generated and saved; generate all possible outputs and later decide what outputs are to be saved; generate and save all output; visualize outputs; and save outputs to files in ASCII, binary format, or any other number of suitable electronic formats. Saving data in binary form has the advantage of being concise, but transportation of the data becomes limited. Maintaining ASCII data files, on other hand, puts it in readable form and also makes it easily transportable to other software for further data analysis.

The Plot Pane

Figures 30, 31:
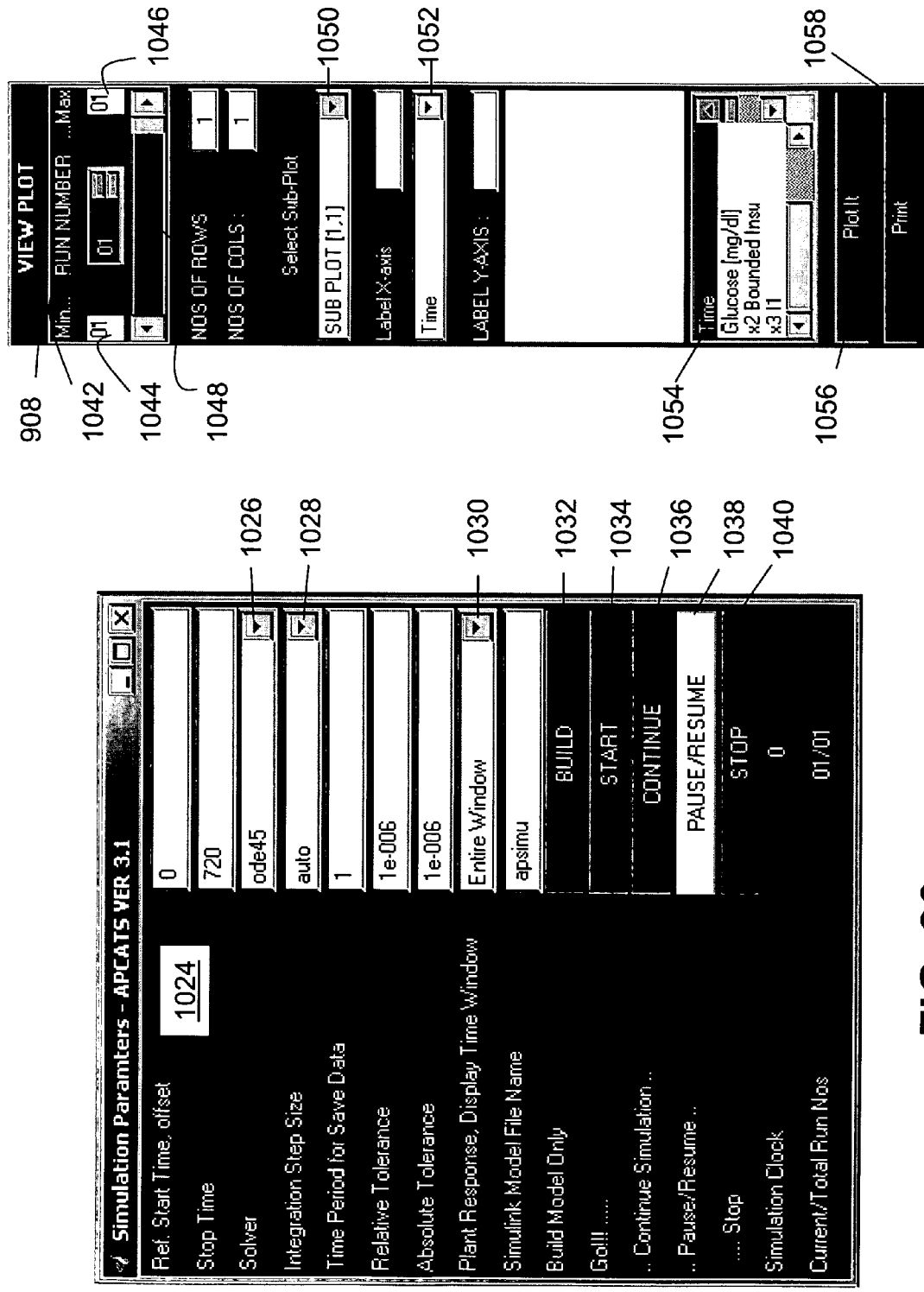
FIG. 30 is a depiction of a graphical user interface providing a Simulation Parameters form for a simulation environment according to the present invention which permits the user to set the start and stop times for a simulation, select an integration routine and step size, and run the simulation.
FIG. 31 is a depiction of a Plot pane portion of the graphical user interface of FIG. 22 which allows a user to graph experimental data on a screen or as a hard copy.

The plot pane 908 of the APCATS main window 902 allows the user to graph experimental data on the screen or as a hard copy, and is enlarged by FIG. 31. A Run Number control 1042 has two purposes: (a) during simulation it displays the number of the experimental run currently being simulated, and (b) outside of simulation it is used to select the run number(s) for which data will be plotted. The run number is displayed in hexadecimal form. To select multiple contiguous runs when selecting data to be plotted, the user holds the shift key down while using the left mouse button to select the first and last numbers of the range of runs to be plotted. To select multiple discrete runs, hold the Ctrl key down while using the left mouse button to click on the individual numbers of the runs to be plotted. Min and Max controls 1044 and 1046, respectively display the minimum and maximum run numbers in hexadecimal form. A slider 1048 provides an alternate method of selecting the run number to be plotted. The left and right ends of the slider respectively represent the minimum and maximum run numbers.

The plot plane 908 can be broken up into smaller subplots aligned in rows and columns. To select the number of rows or number of columns, the user enter the desired values into the Nos. of Rows and Nos. of Columns text boxes. For example, entering 2 as the number of rows and 3 as the number of columns will create six subplots, three each in two rows. Once the number of subplots has been established, the user selects the information to be displayed on each subplot. To set up a given subplot, the user selects the subplot from a Select Sub-Plot dropdown box 1050. The subplots are listed using matrix notation, with the first number in parentheses representing the row of the subplot and the second number representing the column. For each subplot, enter the needed information into the controls below the Select Sub-Plot dropdown box.

To set the label for the x axis, the user enters the label in the Label X-Axis textbox. If the textbox is left empty, the name of the selected independent (x) variable will be used as the label. The user selects the independent variable against which data is to be plotted from a dropdown menu 1052 located below the Label X-Axis control. Different independent variables may be selected for each of the subplots. The default selection is time.

To set the label for the y axis, the user enters the label in a Label Y-Axis textbox. If the textbox is left empty and only one independent (y) variable is selected, the name of the selected variable will be used as the label. If the textbox is left empty and more than one independent variable is selected, the y-axis label will be "* * *". The user selects the dependent variables to plot from a list box 1054 located just above the Plot It button. To select multiple contiguous variables, the user holds the shift key down while using the left mouse button to select the first and last variables in the range. To select multiple discrete variables, the user holds the Ctrl key down while using the left mouse button to click on the individual variables. Up to five dependent variables may be selected for each subplot. The selected variables will be listed in the text box above the selection list.

Once the parameters for each of the subplots have been entered, the plots can be displayed and printed. Plots cannot be created until a simulation has finished running. It is, however, possible to plot data from the previous simulation. To display the plot(s) on the screen, the user clicks a Plot It button

1056. The Plot window will come up, displaying the graphs. To create a printed (hard) copy of the plots, the user clicks a Print button 1058. A dialog box appears (not shown), allowing the user to select various printing options.

Modifying Initialization Files

When APCATS 900 is initialized, all available models are loaded with their default values. Subsequent alterations to the values will be maintained by these objects. The default values are held by the various graphical objects of the APCATS main window 902. Each graphical object has various properties, the two most important for each being UserData and Value. Subsequent subsections detail the information managed by the properties for each of the blocks. The following subsections display the contents of the various initialization files prior to any user modification.

ModelInit.m

```
function [MODEL_TYPE,MODEL_FUN] = ModelInit
% List Descriptive Titles and then function names
% First Descriptors
MODEL_TYPE = {'Model 42',
'Bergman Model',
'User Defined'} ;
% Location of the corresponding function files
MODEL_FUN = {'model42'
'berg'
'usermodel'} ;
```

DietInit.m

```
function [DIET_TYPE,DIET_FUN] = DietInit
% List Descriptive Titles and then function names
% First all Diet Descriptors
DIET_TYPE= { ...
'Balanced Diet'            % 1
'Sweet Diet'               % 2
'Carbohydrates'            % 3
'Beverage'                 % 4
'Alcoholic Drink'          % 5
'Cardio Exercise - Steady' % 6
'Cardio Exercise - Ramp'   % 7
'Cardio Exercise - Hectic' % 8
'Heavy Weight'             % 9
'Mental Stress'} ;         % 10
% Location of the corresponding diet function files
% Each column corresponds to a particular model type
% The order is col #1 corresponds to model #1 listed in ModelInit file
%       col #2 corresponds to model #2 listed in ModelInit file
%       ... and so on
% If a row has quotes with no character within, it signifies that
% corresponding DIET_TYPE row is not available
DIET_FUN= { ...
'diet1m1', 'diet1m2', 'diet1m3'      % 1
'diet2m1', 'diet2m2', 'diet2m3'      % 2
'diet3m1', 'diet1m2', 'diet1m3'      % 3
'diet4m1', '', 'diet1m3'             % 4
'diet5m1', 'diet1m2', ''             % 5
'', 'diet1m2', 'diet1m3'             % 6
'diet7m1', '', 'diet1m3'             % 7
'diet3m1', 'diet1m2', 'diet1m3'      % 8
'diet6m1', 'diet1m2', ''             % 9
'diet7m1', 'diet1m2', 'diet1m3'} ;   % 10
```

SensorInit.m

```
function [SENSOR_TYPE,SENSOR_FUN]=SensorInit
% List Descriptive Titles of Types of Actuators available
% Default = First Type
% Descriptors
SENSOR_TYPE = {'Sensor 1',
'Sensor 2',
'Sensor 3'} ;
% Location of the corresponding function files
SENSOR_FUN = {'sensor1'
'sensor2'
'sensor3'} ;
```

ActuatorInit.m

```
function [ACTUATOR_TYPE,ACTUATOR_FUN]=ActuatorInit
% List Descriptive Titles of Types of Actuators available
% Default = First Type
% Descriptors
ACTUATOR_TYPE = {'Motor 1'
'Motor 2'
'Motor 3'} ;
% Location of the corresponding function files
ACTUATOR_FUN = {'motor1'
'motor2'
'motor3'} ;
```

ControlInit.m

```
function [CONTROLLER_TYPE,CONTROLLER_FUN] =
ControllerInit
% List Descriptive Titles of Types of Controller available
% Default = First Type
CONTROLLER_TYPE = {'PID Controller',
'Adaptive Controller',
'GMS Controller',
'User Defined'} ;
% Location of the corresponding function files
CONTROLLER_FUN = {'pid'
'adap'
'gms'
'usercontrol'} ;
```

SenFailInit.m

```
function [SENFAIL_TYPE,SENFAIL_FLAG]=SenFailInit
% Sensor Fail Init
% Initialization File
% List Descriptive Titles for Failure Modes
% Default = First Type
% Descriptors
SENFAIL_TYPE{1,1} = 'Switch On';
SENFAIL_TYPE{2,1} = 'Switch Off';
SENFAIL_TYPE{3,1} = 'Error Beep';
SENFAIL_TYPE{4,1} = 'Pause';
% Use Flag Definition File (C:\testbed\FlagDefFile) to map
% above descriptors
SENFAIL_FLAG{1,1} = 'NORMAL';
SENFAIL_FLAG{2,1} = 'NO SIGNAL';
SENFAIL_FLAG{3,1} = 'N0 SIGNAL';
SENFAIL_FLAG{4,1} = 'SUSPEND/PAUSE';
```

ActFailInit.m

```
function [ACTFAIL_TYPE,ACTFAIL_FUN]=ActFailInit
% ACTUATOR FAIL INIT
% Initialization File
% List Descriptive Titles of Types of Sensors available
% Default = First Type
% Descriptors
ACTFAIL_TYPE{1,1} = 'Switch On';
ACTFAIL_TYPE{2,1} = 'Switch Off';
ACTFAIL_TYPE{3,1} = 'Error Beep';
ACTFAIL_TYPE{4,1} = 'Battery Low';
ACTFAIL_TYPE{5,1} = 'Pause';
% Use Flag Definition File (C:\testbed\FlagDefFile) to map
% above descriptors
```

```
ACTFAIL_FUN{1,1} = 'NORMAL' ;
ACTFAIL_FUN{2,1} = 'NO SIGNAL' ;
ACTFAIL_FUN{3,1} = 'NO SIGNAL' ;
ACTFAIL_FUN{4,1} = 'SUSPEND/PAUSE' ;
ACTFAIL_FUN{5,1} = 'SUSPEND/PAUSE' ;
```

Defining Disturbance Models

The following is partial code for external disturbances which can be used as a template to create additional disturbances.

| S-function based | Block-diagram based |
|---|---|
| FuncName.m ← Name of the mfile<br>function sys =<br>funcName(t,x,u,flag,param,Scale,t_duration)<br>switch flag<br>case 'IS SIMULINK BLOCK'<br>sys = 0 ;<br>case 'STATE VARIABLES'<br>case 'OUTPUT VARIABLES'<br>case 'PARAMETER VARIABLES'<br>% Redundant case for disturbance function<br>case 'INPUT VARIABLES'<br>case 'EVALUATE DERIVATIVES'<br>case 'EVALUATE OUTPUT'<br>case 'EVALUATE PARAMETERS'<br>case 'EVALUATE MASK PARAMETERS'<br>% Redundant case for non-blk diagram<br>end | FuncName.m ← Name of the mfile<br>function sys =<br>funcName(t,x,u,flag,param,Scale,t_start,t_end,DestBlk)<br>switch flag<br>case 'IS SIMULINK BLOCK'<br>sys = 1 ;<br>case 'STATE VARIABLES'<br>case 'OUTPUT VARIABLES'<br>case 'PARAMETER VARIABLES'<br>% Redundant case for disturbance function<br>case 'INPUT VARIABLES'<br>case 'EVALUATE DERIVATIVES'<br>% Redundant case for disturbance function<br>case 'EVALUATE OUTPUT'<br>% Redundant case for disturbance function<br>case 'EVALUATE PARAMETERS'<br>% Redundant case for disturbance function<br>case 'EVALUATE MASK PARAMETERS'<br>% Define block location<br>SrcBlkPath =<br>SrcBlkFileName =<br>SrcBlkName =<br>% Define List of Variables to be masked<br>% Following Code is not to be modified<br>% Code to obtain the block diagram, copying<br>and assignment of Mask Variables<br>end |

Defining Patient Models

The following is an example of the code for a plant model which also can be used as a temple for developing additional patient models.

```
function sys = model42(t,x,u,flag,para1)
This is a template. You may add sub functions or functions
to implement pieces of the switches. The string names use
cell type structure. Each of the names are string characters
and on separate row switch flag,
case 'STATE VARIABLES',
% EDIT state descriptor.
xN = {...
'Glucose (G)'
'Glucose Rate (GDOT)'
'Insulin (I)'
'Insulin Rate (IDOT)' } ;
% Default Values, Initial Conditions
x0 = [0
0
3
0 ];
sys = {xN, x0} ;
case 'OUTPUT VARIABLES',
% EDIT output descriptor
sys = {...
'Glucose (G)'
'Insulin (I)' } ;
case 'PARAMETER VARIABLES',
% EDIT Parameter Descriptors
pN = {...
'Glucose Coeff [unit]'
'Insulin Coeff [unit]'
'Glucose Constant, KG'
'Insulin Constant, KI' } ;
% Default Parameter Values
p0 = [2 5
NaN
0.12];
% Default Minimum Value
pMin=[NaN
-20
NaN
-1];
% Default Maximum Value
pMax=[NaN
10
NaN
1] ;
sys = {pN, p0, pMin, pMax} ;
case 'INPUT VARIABLES',
% EDIT Input Descriptors
sys = {...
'Glucose Dosage [ml/min]'
'Insulin Dosage [ml/min]'} ;
case 'EVALUATE DERIVATIVES',
% EDIT System dynamics given by appropriate equations
% para1 are the parameter values entering and set by external
functions in general. If constant they should still be visualized
as externally set values.
k1=para1(1); k2=para1(2) ; k3=para1(3) ; k4 = para1(4) ;
xdot(1) = x(2) ;
xdot(2) = -k1*x(1) - k2*x(2) + u(1) ;
xdot(3) = 0 ;
xdot(4) = 0 ;
sys = xdot ;
case 'EVALUATE OUTPUT',
% EDIT Output Equations
y(1) = x(1) ;
y(2) = x(3) ;
sys = y ;
```

```
       otherwise,
       % Display Error
       msg2disp('Error: None of the switch options selected') ;
       end % end of switch
```

Defining Device Models

The following gives partial code for devices which also may be used to develop additional device models.

| S-function based | Block-diagram based |
|---|---|
| function sys = funcName(t,x,u,flag,param,DestBlk)<br>switch flag<br>case 'IS SIMULINK BLOCK'<br>sys = 0 ;<br>case 'STATE VARIABLES'<br>case 'OUTPUT VARIABLES'<br>case 'PARAMETER VARIABLES'<br>case 'INPUT VARIABLES'<br>case 'EVALUATE DERIVATIVES'<br>case 'EVALUATE OUTPUT'<br>case 'EVALUATE PARAMETERS'<br>case 'EVALUATE MASK PARAMETERS'<br>% Redundant case for non-blk diagram<br>end | function sys = funcName(t,x,u,flag,param,DestBlk)<br>switch flag<br>case 'IS SIMULINK BLOCK'<br>sys = 1 ;<br>case 'STATE VARIABLES'<br>case 'OUTPUT VARIABLES'<br>case 'PARAMETER VARIABLES'<br>case 'INPUT VARIABLES'<br>case 'EVALUATE DERIVATIVES'<br>% Redundant case for disturbance function<br>case 'EVALUATE OUTPUT'<br>% Redundant case for disturbance function<br>case 'EVALUATE PARAMETERS'<br>% Redundant case for plant function<br>case 'EVALUATE MASK PARAMETERS'<br>% Define block location<br>SrcBlkPath =<br>SrcBlkFileName =<br>SrcBlkName =<br>% Define List of Variables to be masked<br>% Following Code is not to be modified<br>% Code to obtain the block diagram, copying and assignment of Mask Variables<br>end |

Defining Control Models

The following gives partial code for controller models which can be used as a template to develop additional controller models.

| S-function based | Block-diagram based |
|---|---|
| function sys = funcName(t,x,u,flag,param,DestBlk)<br>switch flag<br>case 'IS SIMULINK BLOCK'<br>sys = 0 ;<br>case 'STATE VARIABLES'<br>case 'OUTPUT VARIABLES'<br>case 'PARAMETER VARIABLES'<br>case 'INPUT VARIABLES'<br>case 'EVALUATE DERIVATIVES'<br>case 'EVALUATE OUTPUT'<br>case 'EVALUATE PARAMETERS'<br>case 'EVALUATE MASK PARAMETERS'<br>% Redundant case for non-blk diagram<br>end | function sys = funcName(t,x,u,flag,param,DestBlk)<br>switch flag<br>case 'IS SIMULINK BLOCK'<br>sys = 1 ;<br>case 'STATE VARIABLES'<br>case 'OUTPUT VARIABLES'<br>case 'PARAMETER VARIABLES'<br>case 'INPUT VARIABLES'<br>case 'EVALUATE DERIVATIVES'<br>% Redundant case for disturbance function<br>case 'EVALUATE OUTPUT'<br>% Redundant case for disturbance function<br>case 'EVALUATE PARAMETERS'<br>% Redundant case for plant function<br>case 'EVALUATE MASK PARAMETERS'<br>% Define block location<br>SrcBlkPath =<br>SrcBlkFileName =<br>SrcBlkName =<br>% Define List of Variables to be masked<br>% Following Code is not to be modified<br>% Code to obtain the block diagram, copying and assignment of Mask Variables<br>end |

Simulation (mdl) File

The below example shown a simulation (mdl) file which as mentioned above may be modified as desired by the user.

```
function [sys,x0,str,ts] = modelname(t,x,u,flag,para1,para2,....)
switch flag
case 'STATE VARIABLES'
...
```

```
...
case 'OUTPUT VARIABLES'
```

```
...
...
case 'PARAMETER VARIABLES'
...
...
case 'INPUT VARIABLES'
...
...
case 'EVALUATE DERIVATIVE'
...
...
case 'EVALUATE OUTPUT'
...
...
end
% By convention, a cell structure format is maintained
var = {'Descriptor field', Value1, Value2, ...} ;
```

The foregoing description of the invention has been presented for purposes of illustration and description. It is not intended to be exhaustive or to limit the invention to the precise form disclosed, and other modifications and variations may be possible in light of the above teachings. The above embodiments disclosed were chosen and described to explain the principles of the invention and its practical application to thereby enable others skilled in the art to best utilize the invention. It is intended that the appended claims be construed to include other alternative embodiments of the invention except insofar as limited by the prior art.

What is claimed is:

1. A computerized system used by a user(s) to developing patient specific therapies for chronic disease management of a patient(s) with a known disease, the system comprising:
 a collection device;
 a server computer having a database; and
 a client computer operably connected to the collection device and the server computer, the client computer having a monitor, memory, and an input device operably connect to a processor, said processor running:
  a data collection protocols module which collects patient specific data via the monitor, the input device, or the collection device according to a data collection protocol specialized to identify or determine a particular aspect of the known disease of the patient, stores collected patient specific data in the database or the memory performs integrity and quality checks on the collected patient specific data stored in the database or the memory and provides to the user for selection therapy assessments/recommendations each with a relevance rating that is based on the integrity and quality of the collected patient specific data,
  a patient models module which enables the user to select via a user interface a patient model from a plurality of patient models provided by at least one of the server computer and the client computer and provides to the user for selection options each with a relevance rating indicating relevance of therapy parameters based on a selected one of the therapy assessments/recommendations so that the relevance rating makes clear if the collected data is not good enough to generate a new therapy,
  a model validation module which validates the selected patient model and provides results to the user for review and acceptance of the selected patient model, an analyses module which applies the patient specific data to the selected,
  accepted patient model to extract patient specific physiological information, and to use the extracted patient specific physiological information to develop one or more patient specific therapies for treating the chronic disease of the patient based on parameters generated from the selected model, and
  a result validation and presentation module which validates the one or more patient specific therapies and presents validated ones of the one or more patient specific therapies each with the confidence interval on the monitor for approval by the user.

2. The computerized system according to claim 1 wherein the data collection protocol dictates specific data to be collected, manner to be collected, and compliancy procedure.

3. The computerized system according to claim 1 wherein for the integrity and quality checks the data collection module enables the system to check for inconsistencies between collected patient specific data and the data collection protocol and time stamps, to determine whether collection performed over a required time period, and to determine for the collected patient data whether data values are in predefined ranges and provide a predetermined number of samples within a certain time window.

4. The computerized system according to claim 1 wherein the system provides the plurality of patient models from at least one of a client computer, a computer server, a portable memory device, computer storage, and a computer readable medium.

5. The computerized system according to claim 1 wherein the plurality of patient models each mathematically represents at least one aspect of human physiology, and provides mapping to different physiological states, conditions or parameters.

6. The computerized system according to claim 1 wherein the module validation module enables the system to perform on the selected patient model at least one of a Bayesian analysis, a cost function analysis, parameter estimation, statistical analysis, numeric analysis, range analysis, gain values analysis, test scenarios analysis, simulations, and modeling.

7. The computerized system according to claim 1 wherein the model validation module enables the system to determine model parameters which are then used to validate the selected patient model.

8. The computerized system according to claim 1 wherein the analyses module provides analysis tools which enables the system to perform at least one of simulations, statistical analysis, sensitivity analysis, visualizations, information extraction, optimizations, and to provide recommendations which include at least one of type, amount, and timing for dosing, exercise, and meals.

9. The computerized system according to claim 1 further comprising a rule/guideline sets module which governs the system in collection of the patient specific data according to the data collection protocol.

10. The computerized system according to claim 1 wherein the result validation and presentation module provides simulation tools which enable the system to test the one or more patient specific therapies for at least one of robustness, stability, sensitivity to parameter variation, and effectiveness, and to generate confidence intervals.

* * * * *